US010426768B2

(12) United States Patent
Moreadith et al.

(10) Patent No.: US 10,426,768 B2
(45) Date of Patent: *Oct. 1, 2019

(54) SUBCUTANEOUS DELIVERY OF POLYMER CONJUGATES OF THERAPEUTIC AGENTS

(71) Applicant: Serina Therapeutics, Inc., Huntsville, AL (US)

(72) Inventors: Randall Moreadith, Huntsville, AL (US); Kunsang Yoon, Madison, AL (US); Zhihao Fang, Madison, AL (US); Rebecca Weimer, Huntsville, AL (US); Bekir Dizman, Huntsville, AL (US); Tacey Viegas, Madison, AL (US); Michael David Bentley, Huntsville, AL (US)

(73) Assignee: Sarina Therapeutics, Inc., Huntsville, AL (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/480,122

(22) Filed: Apr. 5, 2017

(65) Prior Publication Data

US 2017/0202972 A1    Jul. 20, 2017

Related U.S. Application Data

(63) Continuation of application No. 14/355,515, filed as application No. PCT/US2012/063088 on Nov. 1, 2012, now abandoned, which is a continuation-in-part of application No. 13/524,994, filed on Jun. 15, 2012, now Pat. No. 8,383,093.

(60) Provisional application No. 61/554,336, filed on Nov. 1, 2011.

(51) Int. Cl.
| *A61K 31/4745* | (2006.01) |
| *A61K 31/381* | (2006.01) |
| *A61K 31/4045* | (2006.01) |
| *A61K 9/00* | (2006.01) |
| *A61K 31/4462* | (2006.01) |
| *A61K 31/4535* | (2006.01) |
| *A61K 31/7048* | (2006.01) |
| *A61K 47/60* | (2017.01) |
| *A61K 47/54* | (2017.01) |
| *A61K 47/61* | (2017.01) |

(52) U.S. Cl.
CPC ........ *A61K 31/4745* (2013.01); *A61K 9/0019* (2013.01); *A61K 31/381* (2013.01); *A61K 31/4045* (2013.01); *A61K 31/4462* (2013.01); *A61K 31/4535* (2013.01); *A61K 31/7048* (2013.01); *A61K 47/542* (2017.08); *A61K 47/60* (2017.08); *A61K 47/61* (2017.08)

(58) Field of Classification Search
CPC .................................................. A61K 31/4745
USPC ....................................................... 424/78.3
See application file for complete search history.

(56) References Cited

U.S. PATENT DOCUMENTS

| 5,880,131 A | 3/1999 | Greenwald |
| 6,914,121 B2 | 7/2005 | El-Tayar |
| 7,872,041 B2 | 1/2011 | Scheller |
| 7,943,141 B2 | 5/2011 | Harris |
| 8,088,884 B2 | 1/2012 | Yoon |
| 8,110,651 B2 | 2/2012 | Yoon |
| 8,383,093 B1 | 2/2013 | Moreadith |
| 8,597,633 B2 | 12/2013 | Moreadith |
| 2006/0051315 A1 | 3/2006 | Scaria et al. |
| 2011/0121224 A1 | 5/2011 | Matsushita |
| 2011/0123453 A1 | 5/2011 | Bentley et al. |
| 2012/0123055 A1 | 5/2012 | Yoon |
| 2012/0136123 A1 | 5/2012 | Harris |
| 2014/0112880 A1 | 4/2014 | Moreadith |

FOREIGN PATENT DOCUMENTS

| EP | 1466627 | 10/2004 |
| WO | WO9955376 | 11/1999 |
| WO | 2010100220 | 10/2010 |
| WO | 2011127256 | 10/2011 |

OTHER PUBLICATIONS

Dahse, Thomas, Extended European Search Report: Supplementary European Search Report and Search Opinion—WO Applicatin No. 12846647.1; The European Patent Office (Munich); pp. 1-13 dated Sep. 15, 2015 Sep. 15, 2015.
Belluzzi, J.D., et al., N-0923, a Selective Dopamine D2 Receptor Agonist, is Efficacious in Rat and Monkey Models of Parkinson's Disease; BELLUZI; Movement Disorders, vol. 9, No. 2, pp. 147-154 Jan. 1, 1994 Jan. 1, 1994.
D'Souza, A.J., et al., Release from Polymeric Prodrugs: Linkages and Their Degradation; D'Souza; Journal of Pharmaceutical Sciences, vol. 93, No. 8, pp. 1962-1979 Aug. 1, 2004 Aug. 1, 2004.
Stocchi, Fabrizio, et al., Intermittent vs. Continuous Levodopa Administration in Patients with Advanced Parkinson Disease; Arch Neurol, vol. 62, pp. 905-910 Jun. 1, 2005 Jun. 1, 2005.
McLeod, Andrew, et al., Glucocorticoid-Dextran Conjugates as Potential Prodrugs for Colon-Specific Delivery: Hydrolysis in Rat Gastrointestinal Tract Contents; Journal of Pharmaceutical Sciences, vol. 83, No. 9, pp. 1284-1288 May 2, 1994 May 2, 1994.
Bibbiani, Francesco, et al., Continuous dopaminergic stimulation redues risk of motor complications in parkinsonian primates; Experimental Neurology, vol. 192, pp. 73-78 Jan. 19, 2005 Jan. 19, 2005.
Stockwell, K.A., et al., Continuous delivery of ropinirole reverses motor deficits without dyskinesia induction in MPTP-treated common marmosets; Experimental Neurology, vol. 211, pp. 172-179 Feb. 9, 2008 Feb. 9, 2008.
Di Stefano, Antonio, et al., Antiparkinson Prodrugs; Molecules, vol. 13, pp. 46-68 Jan. 16, 2008 Jan. 16, 2008.

(Continued)

Primary Examiner — Devang K Thakor
(74) Attorney, Agent, or Firm — Thomas G. Peterson; Maynard Cooper & Gale

(57) ABSTRACT

The present disclosure provides polymer conjugates comprising a polymer and an agent, the agent linked to the polymer via a linking group containing a cleavable moiety.

20 Claims, 3 Drawing Sheets

(56) References Cited

OTHER PUBLICATIONS

Cawello, Will, et al., Absorption, Disposition, Metabolic Fate, and Elimination of the Dopamine Agonist Rotigotine in Man: Administration by Intravenous Infustion or Transdermal Delivery; Drug Metabolism and Disposition, vol. 37, No. 10, pp. 2055-2060.

Viegas, Tacey, et al., Polyoxazoline: Chemistry, Properties, and Applications in Drug Delivery; Bioconjugate Chemistry, vol. 22, pp. 976-986 Apr. 1, 2011 Apr. 1, 2011.

Li, Xiaoling, et al., Synthesis of Poly(Hydroxypropylglutamine-Prazosin Carbamate) and Release Studies; Pharmaceutical Research, vol. 8, No. 4, pp. 527-530 Jan. 1, 1991 Jan. 1, 1991.

Duncan, R., et al., Polymer-drug conjugates: towards a novel approach for the treatment of endrocine-related cancer; Endocrine-Related Cancer, vol. 12, pp. S189-S199 Jan. 1, 2005 Jan. 1, 2005.

Poewe, Werner, et al., Efficacy of pramipexole and transdermal rotigotine in advanced Parkinson's disease: a double-blind, double-dummy, randomised controlled trial, Lancet Neurology, vol. 6, pp. 513-520 May 1, 2007.

Stockwell, K.A., et al., Continuous administration of rotigotine to MPTP-treated common marmosets enhances anti-parkinsonian activity and reduces dyskinesia induction; Experimental Neurology, vol. 219 pp. 533-542 Jul. 18, 2009 Jul. 18, 2009.

Schmidt, Werner, et al., Continuous versus pulsatile administration of rotigotine in 6-OHDA-lesioned rats: contralateral rotations and abnormal involutary movements; J Neural Transm vol. 115, pp. 1385-1392 Jan. 1, 2008 Jan. 1, 2008.

Trenkwalder, Claudia, et al., Efficacy of rotigotine for treatment of moderate-to-severe restless legs syndrome: a randomised, double-blind, placebo-controlled trial; Lancet Neurol, vol. 7, pp. 595-604 May 31, 2008 May 31, 2008.

Joshi, Kasturi, Transdermal Drug Delivery Systems and Their Use of Polymers; MatE 175-Biomaterials, pp. 1-31 Nov. 26, 2008 Nov. 26, 2008.

Li, Chun, et al., Polymer-Drug Conjugates: Recent Development in Clinical Oncology; Adv Drug Delivery Reviews, vol. 60, No. 8, pp. 886-898 May 22, 2008 May 22, 2008.

Becamel, Philippe, International Preliminary Report on Patentability and Written Opinion—International Application No. PCT/US2012/063088; The International Bureau of WIPO, pp. 1-11 dated May 15, 2014 May 15, 2014.

Cesana, Sonia, et al., First Poly(2-oxazoline)s with Pendant Amino Groups; Macromol Chem Phys, vol. 207,pp. 183-192 Jan. 1, 2006 Jan. 1, 2006.

Taubmann, Christian, et al., First Aldehyde-Functionalized Polly(2-oxazoline)s for Chemoselective Ligation; Macromol. biosci., vol. 5, pp. 603-602 May 2, 2005 May 2, 2005.

The Parkinson Study Group, Arch Neurol., vol. 60; pp. 1721-1728 Jan. 1, 2003.

Kehr, J., et al., Continuous delivery of rotigotine decreases extracellular dopamine suggesting continuous receptor stimulation; J. Neural Transm, vol. 114, pp. 1027-1031 Apr. 16, 2007 Apr. 16, 2007.

SUBCUTANEOUS DELIVERY OF POLYMER CONJUGATES OF THERAPEUTIC AGENTS

CROSS REFERENCE TO RELATED APPLICATIONS

The present application is a continuation of U.S. application Ser. No. 14/355,515, filed May 1, 2014 (currently pending). U.S. application Ser. No. 14/355,515 is a 371 of International Application No. PCT/US12/63088, filed Nov. 1, 2012 (currently expired), PCT/US12/63088 is a continuation in part of U.S. application Ser. No. 13/524,994 filed Jun. 15, 2012, now U.S. Pat. No. 8,383,093, issued on Feb. 26, 2013, which claims the benefit of U.S. Provisional Application No. 61/554,336, filed Nov. 1, 2011.

FIELD OF THE DISCLOSURE

The present disclosure is related generally to polymer conjugates. The present disclosure relates more specifically to polymer conjugates comprising a water soluble polymer and an agent, the agent linked to the water soluble polymer by a releasable linker, the releasable linker comprising a cleavable moiety which is cleavable in a subject to release the agent after administration of the conjugate to a subject. Methods of using such conjugates for treatment and methods for the preparation of such conjugates are also provided.

BACKGROUND

Development of drug conjugates with water-soluble polymers can enhance the properties of the drugs, including water-solubility, pharmacokinetics, metabolism, bio-distribution, and bioactivity. A number of polymer-protein conjugates having stable linkages have been approved by FDA and are currently valuable medicines (Bentley, M. D. et al., Poly(ethylene) Glycol Conjugates of Biopharmaceuticals in Drug Delivery, in Knablein, J. (ed.), Modern Biopharmaceuticals, Wiley-VCH Verlag GbH, Volume 4, 2005, Chapter 2, pp. 1393-1418). Conjugation of water-soluble polymers including poly(ethylene glycol), poly(glutamate), and poly(hydroxypropylmethacrylate) with small molecule oncolytics has led to several products in clinical trials, but as yet, no marketed drugs (Mero, A., PEG: a useful technology in anticancer therapy, in Veronese, F. M. (ed.), PEGylated Protein Drugs: Basic Science and Clinical Application, Birkhauser Verlag, Basel, 2009, pp. 273-281). Unlike the case of protein conjugates, it is frequently useful to formulate small-molecule conjugates with releasable linkages. These polymer conjugates are known to significantly extend the half-lives of the attached small molecules. When the oncolytic drug, irinotecan, was attached to a multi-arm polyethylene glycol polymer, and injected intravenously to mice the plasma half-life of its active metabolite SN-38 was increased from 2 hours to 17 days (Eldon, M. A. et al., Anti-tumor activity and pharmacokinetics of NKTR-102, PEGylated-irinotecan conjugate, in irinotecan-resistant tumors implanted in mice, Poster number: P-0722, presented at the 14th European Cancer Conference (ECCO 14), 23-27 Sep. 2007, Barcelona, Spain).

The advantage of polymer conjugates of small molecule drugs derives from the typically short in vivo half-life of the drug. The short half-lives of these drugs require frequent dosing of several times daily which results in "pulses" of high concentration of the drug, followed by longer periods where the drug concentration in the blood stream is below the amount required for therapeutic efficacy. For example, in some cases, such as Parkinson's disease (PD), pulsatile stimulation of striatal dopamine receptors with short-acting dopamine agonists or levo-dopa may actually accelerate molecular and physiological changes that lead to degeneration of dopaminergic neurons in the central nervous system (CNS), thus promoting motor fluctuations (dyskinesias) that can be disabling. Physiological levels that are maintained at a steady state without phasic peak and trough levels have been shown to eliminate these side effects in both animals and humans. Low solubility of some of these compounds, combined with limited oral bioavailabity, further complicates their clinical use. These problems may be solved by preparation of a soluble polymer conjugate.

The art is lacking a composition that is administered by the subcutaneous route and is able to provide sustained, controllable delivery of a drug over a period of days to weeks. The present disclosure provides polymer conjugates comprising a water soluble polymer and an agent, the agent linked to the water soluble polymer by a releasable linker, the releasable linker comprising a cleavable moiety which is cleavable in a subject to release the agent after administration of the conjugate to a subject. The present disclosure provides such conjugates. As shown herein, the subcutaneous injection of such polymer conjugates provides sustained delivery of the agent at therapeutically effective levels of a drug over a time period of days to weeks.

SUMMARY OF THE DISCLOSURE

Figure 1A:
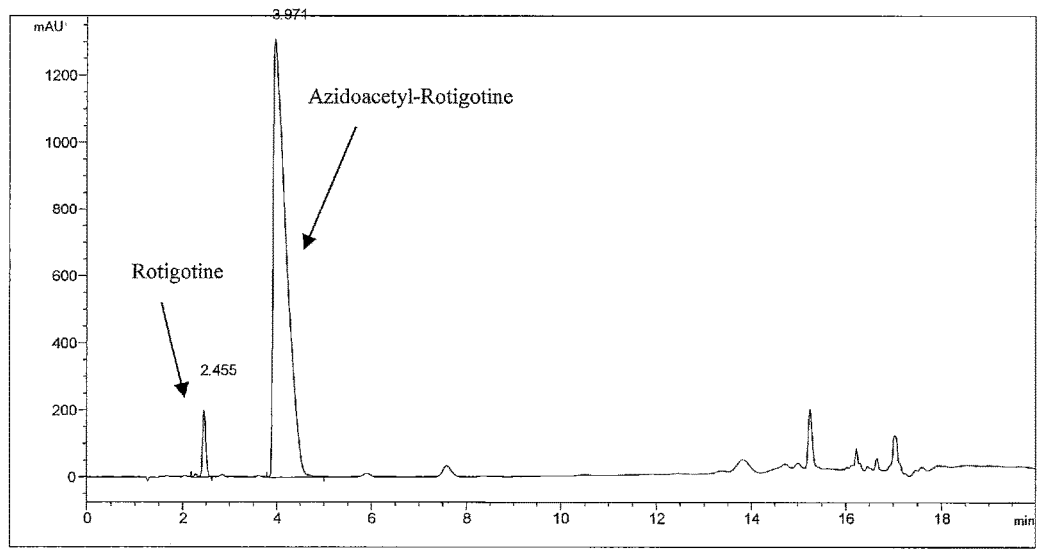
FIG. 1A shows an HPLC chromatogram of rotigotine 2-azidoacetate before reversed phase chromatography purification

In a first aspect, the present disclosure provides a polymer conjugate comprising a water-soluble polymer and an agent, the agent linked to the polymer by a releasable linker. In certain embodiments of this aspect, the agent is a diagnostic agent or a therapeutic agent, such as, but not limited to, an organic small molecule.

In a second aspect, the present disclosure provides a polymer conjugate comprising a water-soluble polymer and an agent useful in the treatment of Parkinson's Disease (PD) or other diseases or conditions related to dopamine insufficiency in the peripheral or central nervous system in which the agent is linked to the polymer by a releasable linker.

In a third aspect, the present disclosure provides a polymer conjugate comprising a water-soluble polymer and an agent useful in the treatment of a disorder characterized by excessive GABA re-uptake or GABA re-uptake or an anxiety disorder, social anxiety disorder, panic disorder, neuropathic pain, chronic pain, muscle tremors, muscle spasms, seizures, convulsions and/or epilepsy in which said inhibitor is linked to the polymer by a releasable linker.

In a fourth aspect, the present disclosure provides a polymer conjugate comprising a water-soluble polymer and a dopamine agonist in which the dopamine agonist is linked to the polymer by a releasable linker or a water-soluble polymer and a GABA re-uptake inhibitor in which the GABA re-uptake inhibitor is linked to the polymer by a releasable linker.

In a fifth aspect, the present disclosure provides a polymer conjugate comprising a water-soluble polymer and rotigotine, the rotigotine linked to the polymer by a releasable linker, a polymer conjugate comprising a water-soluble polymer and ropinirole, the ropinirole linked to the polymer by a releasable linker and a polymer conjugate comprising a water-soluble polymer and tiagabine, the tiagabine linked to the polymer by a releasable linker. In one embodiment of the foregoing, the water soluble polymer is polyoxazoline, dextran, dextran modified by oxidation or polyethylene glycol.

In a sixth aspect, the present disclosure provides a poly(oxazoline) (POZ) conjugate comprising a POZ polymer and an agent, the agent linked to the POZ polymer by a releasable linker. In certain embodiments of this aspect, the agent is a diagnostic agent or a therapeutic agent, such as, but not limited to, an organic small molecule.

In a seventh aspect, the present disclosure provides a POZ polymer conjugate comprising a POZ polymer and an agent useful in the treatment of PD or other diseases or conditions related to dopamine insufficiency in the peripheral or central nervous system, the agent linked to the polymer by a releasable linker.

In an eighth aspect, the present disclosure provides a POZ polymer conjugate comprising a POZ polymer and an agent useful in the treatment of a disorder characterized by excessive GABA re-uptake or GABA re-uptake or an anxiety disorder, social anxiety disorder, panic disorder, neuropathic pain, chronic pain, muscle tremors, muscle spasms, seizures, convulsions and/or epilepsy in which said inhibitor is linked to the polymer by a releasable linker.

In ninth aspect, the present disclosure provides a POZ polymer conjugate comprising a POZ polymer and a dopamine agonist, the dopamine agonist linked to the POZ polymer by a releasable linker or and a POZ polymer and a GABA re-uptake, the GABA re-uptake inhibitor is linked to the POZ polymer by a releasable linker.

In a tenth aspect, the present disclosure provides a POZ polymer conjugate comprising a POZ polymer and rotigotine, the rotigotine linked to the POZ polymer by a releasable linker, a POZ polymer conjugate comprising a POZ polymer and ropinirole, the ropinirole linked to the POZ polymer by a releasable linker and a POZ polymer conjugate comprising a POZ polymer and tiagabine, the tiagabine linked to the POZ polymer by a releasable linker.

In any of the first through fifth aspects, the water-soluble polymer may be a water soluble polymer known in the art. Exemplary water soluble polymers suitable for use with the present disclosure include, but are not limited to, the following water-soluble polymers: POZ, poly(5,6-dihydro-4h-1,3-oxazine), dextran, dextran modified by oxidation, polyethylene glycol (PEG), poly(hydroxypropylmethacrylate), polyglutamic acid, polylactic-polyglutamic acid mixture, polysialic acid, polycaprolactone, polyvinylpyrrolidone, poly(sialic acid), polyglycosaminoglycan, polyglycerol, poly(acryloyloxyethylphosphorylcholine), and methacrylate-based copolymer with synthetic forms of phosphorylcholine. Combinations of the foregoing are also included. In a particular embodiment of the first through fifth aspects, the water-soluble polymer is POZ, PEG, dextran or dextran modified by oxidation. In another particular embodiment of the first through fifth aspects, the water-soluble polymer is POZ. In another embodiment, of the first through fifth aspects, the water-soluble polymer is a copolymer of PEG and POZ.

In any of the first through tenth aspects, the releasable linker contains a cleavable moiety, the cleavable moiety being optionally contained in a larger chemical moiety (i.e, a linking group), allowing the chemical linkage between the agent and the polymer to be cleaved. In certain embodiments of this aspect, the cleavable moiety is an ester, a carbonate ester, a carboxylate ester, a carbamate, a disulfide, an acetal, a hemiacetal, a phosphate, a phosphonate or an amide. In a particular embodiment, the cleavable moiety is an ester. Suitable ester functionalities include, but are not limited to, carboxylate ester and carbonate esters.

In any of the foregoing aspects, exemplary agents useful in the treatment of PD or other diseases or conditions related to dopamine insufficiency in the peripheral or central nervous include, but are not limited to, dopamine agonists, adenosine $A_{2A}$ antagonist, anticholinergics, monamine oxidase-B inhibitors and catechol-O-methyl transferase (COMT) inhibitors. Exemplary dopamine agonists include, but are not limited to, rotigotine, pramipexole, quinagolide, fenoldopam, apomorphine, 5-OH-DPAT, ropinirole, pergolide, cabergoline, and bromocriptine. Exemplary anticholinergics include, but are not limited to, trihexyphenidyl, biperidin and hyoscyamine. Exemplary monamine oxidase-B inhibitors include, but are not limited to, seligiline and rasagiline. Exemplary COMT inhibitors include, but are not limited to, tolcapone and entacapone. Exemplary A2a antagonists include, but are not limited to, caffeine, theophylline, istradefylline, and preladenant.

In any of the foregoing aspects, exemplary GABA re-uptake inhibitor include, but are not limited to, tiagabine and nipecotic acid. In any of the third, fourth, eighth or ninth aspects, the GABA re-uptake inhibitor is tiagabine.

In any of the foregoing aspects, exemplary dopamine agonists include, but are not limited to, rotigotine, pramipexole, quinagolide, fenoldopam, apomorphine, 5-OH-DPAT, ropinirole, pergolide, cabergoline, and bromocriptine. In any of the second, fourth, seventh or ninth aspects, the dopamine agonist is rotigotine. In any of the second, fourth, seventh or ninth aspects, the dopamine agonist is (−)rotigotine.

In any of the first through tenth aspects, the agent may be a diagnostic agent or a therapeutic agent. In any of the first through tenth aspects, the therapeutic agent may be an organic small molecule.

In an eleventh aspect, the present disclosure provides a method of treatment for a disease, the method comprising the steps of administering a conjugate of the first through tenth aspects to a subject.

In a twelfth aspect, the present disclosure provides a method of treatment for a disease, the method comprising the step of administering a conjugate of the first through tenth aspects to a subject, wherein the level of the agent in the bloodstream is controlled by the nature of the agent, the nature of the linking group, the nature of the polymer, the size of the polymer, the method of delivery or a combination of the foregoing.

In a thirteenth aspect, the present disclosure provides a method of treatment for PD or other diseases or conditions related to dopamine insufficiency in the peripheral or central nervous system, the method comprising the step of administering a conjugate of the first-second, fourth-seventh or ninth-tenth aspects to a subject.

In an fourteenth aspect, the present disclosure provides a method of treatment for PD or other diseases or conditions related to dopamine insufficiency in the peripheral or central nervous system, the method comprising the step of administering a conjugate of the first-second, fourth-seventh or ninth-tenth aspects to a subject, wherein the levels of the agents in the bloodstream is controlled by the nature of the agent, the nature of the linking group, the nature of the polymer, the size of the polymer, the method of delivery or a combination of the foregoing.

In a fifteenth aspect, the present disclosure provides a method of treatment for a disorder characterized by excessive GABA re-uptake or GABA re-uptake or an anxiety disorder, social anxiety disorder, panic disorder, neuropathic pain, chronic pain, muscle tremors, muscle spasms, /seizures, convulsions and/or epilepsy, the method comprising the step of administering a conjugate of the third-fourth, sixth or eighth-ninth aspects to a subject.

In a sixteenth aspect, the present disclosure provides a method of treatment for a disorder characterized by excessive GABA re-uptake or GABA re-uptake or an anxiety disorder, social anxiety disorder, panic disorder, neuropathic pain, chronic pain, muscle tremors, muscle spasms, seizures, convulsions and/or epilepsy, the method comprising the step of administering a conjugate of the third-fourth, sixth or eighth-ninth aspects to a subject, wherein the levels of the agents in the bloodstream is controlled by the nature of the agent, the nature of the linking group, the nature of the polymer, the size of the polymer, the method of delivery or a combination of the foregoing.

In any of the eleventh through sixteenth aspects, the conjugate is administered to a subject by subcutaneous administration.

In any of the eleventh through sixteenth aspects, the levels of the released agent in the plasma of a subject is controlled by the dose of POZ-conjugate delivered via subcutaneous route.

In any of the eleventh through sixteenth aspects, the method of treatment provides sustained, controllable delivery of the agent over a period of days to weeks.

In any of the eleventh through sixteenth aspects, the method of treatment may further comprise identifying a subject in need of such treatment.

In any of the eleventh through sixteenth aspects, the conjugate is administered in a therapeutically effective amount.

In a seventeenth aspect, the present disclosure provides for methods of manufacture of a conjugate of the first through tenth aspects.

In an eighteenth aspect, the present disclosure provides for kits containing a conjugate of the first through tenth aspects along with instructions for administering the conjugate.

DETAILED DESCRIPTION

Definitions

As used herein, the term "agent" refers to any molecule having a therapeutic or diagnostic application, wherein the agent is capable of forming a linkage with a functional group on a polymer or a linking group attached to a polymer, the agent including, but not limited to, a therapeutic agent (such as but not limited to a drug), a diagnostic agent or an organic small molecule. In a specific embodiment, agent is useful in the treatment of PD or other diseases or conditions related to dopamine insufficiency in the peripheral or central nervous system. In a specific embodiment, the agent is a dopamine agonist, adenosine $A_{2A}$ antagonist, an anticholinergic, a monoamine oxidase-B inhibitor or a catechol-O-methyl transferase (COMT) inhibitor. In a specific embodiment, the agent is useful in the treatment of a disorder characterized by excessive GABA re-uptake or GABA re-uptake or an anxiety disorder, social anxiety disorder, panic disorder, neuropathic pain, chronic pain, muscle tremors, muscle spasms, seizures, convulsions and/or epilepsy. In a specific embodiment, the agent is a dopamine agonist. In another specific embodiment, the agent is a GABA uptake inhibitor.

As used herein, the term "link", "linked" "linkage" or "linker" when used with respect to a polymer or agent described herein, or components thereof, refers to groups or bonds that normally are formed as the result of a chemical reaction and typically are covalent linkages.

As used herein, the term "releasable linker" or "releasable functionality" refers to a chemical linkage containing a cleavable moiety that is cleavable in a subject in vivo under physiological conditions in the subject after a conjugate of the present disclosure has been administered to the subject. In one embodiment, the cleavable moiety is cleaved by a chemical reaction. In aspect of this embodiment, the cleavage is by reduction of an easily reduced group, such as, but not limited to, a disulfide. In one embodiment, the cleavable moiety is cleaved by a substance that is naturally present or induced to be present in the subject. In an aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing.

As used herein, the term "alkyl", whether used alone or as part of a substituent group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)CH(CH$_3$)$_2$, —CH(CH$_2$ CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl" and "unsubstituted alkynyl" refers to alkyl, alkenyl and alkynyl groups that do not contain heteroatoms.

As used herein, the term "substituted alkyl", "substituted alkenyl" and "unsubstituted alkynyl" refers to alkyl alkenyl and alkynyl groups as defined above in which one or more bonds to a carbon(s) or hydrogen(s) are replaced by a bond to non-hydrogen or non-carbon atoms such as, but not limited to, an oxygen atom in groups such as alkoxy groups and aryloxy groups; a sulfur atom in groups such as, alkyl and aryl sulfide groups, sulfone groups, sulfonyl groups, and sulfoxide groups; a silicon atom in groups such as in trialkylsilyl groups, dialkylarylsilyl groups, alkyldiarylsilyl groups, and triarylsilyl groups; and other heteroatoms in various other groups.

As used herein, the term "unsubstituted aralkyl" refers to unsubstituted alkyl or alkenyl groups as defined above in which a hydrogen or carbon bond of the unsubstituted or substituted alkyl or alkenyl group is replaced with a bond to a substituted or unsubstituted aryl group as defined above. For example, methyl ($CH_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms, such as, but not limited to, those atoms described above with respect to a substituted alkyl, and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl or alkenyl, group to define a fused ring system (e.g. dihydronaphthyl or tetrahydronaphthyl). Thus, the phrase "substituted aryl" includes, but is not limited to tolyl, and hydroxyphenyl among others.

As used herein, the term "unsubstituted heterocyclyl" refers to both aromatic and nonaromatic ring compounds including monocyclic, bicyclic, and polycyclic ring compounds containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms, condensed unsaturated heterocyclic groups containing 1 to 4 nitrogen atoms, unsaturated 3 to 8 membered rings containing 1 to 2 oxygen atoms and 1 to 3 nitrogen atoms, saturated 3 to 8 membered rings containing 1 to 2 oxygen atoms and 1 to 3 nitrogen atoms such, unsaturated condensed heterocyclic groups containing 1 to 2 oxygen atoms and 1 to 3 nitrogen atoms, unsaturated 3 to 8 membered rings containing 1 to 3 sulfur atoms and 1 to 3 nitrogen atoms, saturated 3 to 8 membered rings containing 1 to 2 sulfur atoms and 1 to 3 nitrogen atoms, saturated and unsaturated 3 to 8 membered rings containing 1 to 2 sulfur atoms, unsaturated condensed heterocyclic rings containing 1 to 2 sulfur atoms and 1 to 3 nitrogen atoms, unsaturated 3 to 8 membered rings containing oxygen atoms, unsaturated condensed heterocyclic rings containing 1 to 2 oxygen atoms, unsaturated 3 to 8 membered rings containing an oxygen atom and 1 to 2 sulfur atoms, saturated 3 to 8 membered rings containing 1 to 2 oxygen atoms and 1 to 2 sulfur atoms, unsaturated condensed rings containing 1 to 2 sulfur atoms, and unsaturated condensed heterocyclic rings containing an oxygen atom and 1 to 2 oxygen atoms. Heterocyclyl group also include those described above in which one or more S atoms in the ring is double-bonded to one or two oxygen atoms (sulfoxides and sulfones).

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes heterocyclyl groups in which one of the carbons is bonded to one of the non-carbon or non-hydrogen atom, such as, but not limited to, those atoms described above with respect to a substituted alky and substituted aryl groups and also includes heterocyclyl groups in which one or more carbons of the heterocyclyl group is bonded to a substituted and/or unsubstituted alkyl, alkenyl or aryl group as defined herein. This includes bonding arrangements in which two carbon atoms of an heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocylalkyl" refers to unsubstituted alkyl or alkenyl groups as defined above in which a hydrogen or carbon bond of the unsubstituted alkyl or alkenyl group is replaced with a bond to a substituted or unsubstituted heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocylalkyl" has the same meaning with respect to unsubstituted heterocylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

As used herein, the terms "treatment", "treat" and "treating" refers a course of action (such as administering a conjugate or pharmaceutical composition) initiated after the onset of a symptom, aspect, or characteristics of a disease or condition so as to eliminate or reduce such symptom, aspect, or characteristics. Such treating need not be absolute to be useful.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the term "in need of prevention" refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

As used herein, the term "individual", "subject" or "patient" refers to any animal, including mammals, such as mice, rats, other rodents, rabbits, dogs, cats, swine, cattle, sheep, horses, or primates, and humans. The term may specify male or female or both, or exclude male or female.

As used herein, the term "therapeutically effective amount" refers to an amount of a conjugate, either alone or as a part of a pharmaceutical composition, that is capable of having any detectable, positive effect on any symptom, aspect, or characteristics of a disease or condition. Such effect need not be absolute to be beneficial.

General Description

The present disclosure provides polymer conjugates consisting of, consisting essentially of or comprising a water-soluble polymer and an agent. In one embodiment, the agent may be linked to the polymer backbone via a direct linkage through a reactive group on the agent and a reactive group on the polymer. In one embodiment, the direct linkage contains at least one cleavable moiety such that in vivo under physiological conditions in the body of a subject, such as, but not limited to, a human, the agent is released from the polymer at some point after administration of the polymer conjugate to the subject. In an alternate embodiment, the agent may be linked to the polymer through a linking group. In one embodiment, the linking group contains at least one cleavable moiety such that in vivo under physiological conditions in the body of a subject, such as, but not limited to, a human, the agent is released from the polymer at some point after administration of the polymer conjugate to the subject. Such releasable moieties are discussed herein. In one embodiment, the linking group contains, in addition to the cleavable moiety, a group capable of forming a linkage with a reactive group on the polymer, and a group capable of forming a linkage with a reactive group on the agent. Regardless of the form of the linkage, the linkage is a releasable linkage that allows the agent to be released from the polymer at some point after administration of the conjugate to a subject via cleavage of the cleavable moiety. The release kinetics of the agent from the conjugate provides sustained, controllable delivery of the agent over a period of days to weeks. In one embodiment, the release kinetics of the agent from the polymer is controlled by the nature of the linking group, the nature of the agent, the nature of the polymer, the size of the polymer, the method of delivery or a combination of the foregoing. In one embodiment, the release kinetics of the agent from the polymer is controlled by the nature of the linking group. In one embodiment, the release kinetics of the agent from the polymer is controlled by the nature of the linking group and/or the nature of the agent. In one embodiment, the release kinetics of the agent from the polymer is controlled by the nature of the linking group and/or the nature of the polymer. In one embodiment, the release kinetics of the agent from the polymer is controlled by the nature of the linking group, the nature of the agent and/or the nature of the polymer.

In a general embodiment, the polymer conjugate of the present disclosure may be represented by the general formula I.

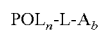

$$POL_n\text{-}L\text{-}A_b \qquad \text{I}$$

wherein,
POL is a water-soluble polymer;
n is 1-1000 and represent the number of monomer units comprising the water-soluble polymer;
b is 1 to 50, provided that n is always greater than or equal to b;
L is an optional linking group containing a cleavable moiety or represents a direct linkage through a reactive group on the agent and a reactive group on the polymer, provided that the direct linkage forms a cleavable moiety; and
A is an agent.

The polymer portion of the disclosed polymer conjugates may take on a variety of forms. In certain embodiments, the polymer is a poly(oxazoline) (POZ), poly(5,6-dihydro-4h-1,3-oxazine), a dextran, a dextran modified by oxidation, a polyethylene glycol (PEG), a poly(hydroxypropylmethacrylate), a polyglutamic acid, a polylactic-polyglutamic acid mixture, a polysialic acid, a polycaprolactone, a polyvinylpyrrolidone, a glycosaminoglycans, a polyglycerol, a poly(acryloyloxyethylphosphorylcholine), or a methacrylate-based copolymer with synthetic forms of phosphorylcholine; combinations of the foregoing are also included.

In one embodiment, the polymer is a poly(oxazoline) (POZ). In still another embodiment, the polymer is a polyethylene glycol (PEG). In still another embodiment, the polymer is a dextran. In still another embodiment, the polymer is a dextran modified by oxidation.

The agent may be any agent useful in the treatment of a disease or condition or the diagnosis of a disease or condition. In certain embodiments, the agent is a diagnostic agent or a therapeutic agent. In certain embodiment, the therapeutic agent is an organic small molecule. In one embodiment, the agent is a compound useful in the treatment of PD or other diseases or conditions related to dopamine insufficiency in the peripheral or central nervous system. In another embodiment, the agent is useful in the treatment of a disorder characterized by excessive GABA re-uptake or GABA re-uptake. In another embodiment, the agent is useful in the treatment of an anxiety disorder, social anxiety disorder, panic disorder, neuropathic pain, chronic pain, muscle tremors, muscle spasms, seizures, convulsions and/or epilepsy. The nature of the agents is described in more detail in the present disclosure.

The linking group may form linkages with any reactive group on the polymer backbone and any reactive group on the agent. The linkage between the linking group and the polymer may be formed on a terminal end of the polymer. Alternatively, the linkage between the linking group and the polymer may be formed using a side chain group of the polymer (referred to herein as a "pendent" position). Furthermore, the linking group may include components of the reactive group that was originally present on the polymer or the agent.

Suitable linking groups are described herein. In a particular embodiment, the polymer conjugates of the present disclosure may be represented by the general formula II.

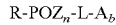
R-POZ$_n$-L-A$_b$                II wherein,
R is an initiating group;
POZ is a polyoxazoline polymer;
n is 1-1100 and represent the number of monomer units comprising the polyoxazoline polymer;
b is 1 to 50, provided that n is always greater than or equal to b;
L is an optional linking group containing a cleavable moiety or represents a direct linkage through a reactive group on the agent and a reactive group on the polymer, provided that the direct linkage forms a cleavable moiety; and A is an agent.

A variety of POZ polymers may be used in the POZ conjugates of the present disclosure. The POZ may contain a single type or class of functional groups or may contain more than one type or class of functional groups. The POZ be a linear POZ polymer, a branched POZ polymer, a pendent POZ polymer or a multi-armed POZ polymer. Various representative POZ polymers are described herein. The POZ polymer may be prepared by living cation polymerization or by other methods as is known in the art. Representative POZ polymers are described in U.S. Pat. Nos. 7,943,141, 8,088,884, 8,110,651 and 8,101,706, application Ser. Nos. 13/003,306, 13/549,312 and 13/524,994, each of which is incorporated herein by reference for such teachings. In one embodiment, the POZ polymer is prepared by living cation polymerization.

The agent may be any agent useful in the treatment of a disease or condition or the diagnosis of a disease or condition. In certain embodiments, the agent is a diagnostic agent or a therapeutic agent. In certain embodiment, the therapeutic agent is an organic small molecule. In one embodiment, the agent is a compound useful in the treatment of PD or other diseases or conditions related to dopamine insufficiency in the peripheral or central nervous system. In another embodiment, the agent is useful in the treatment of a disorder characterized by excessive GABA re-uptake or GABA re-uptake. In another embodiment, the agent is useful in the treatment of an anxiety disorder, social anxiety disorder, panic disorder, neuropathic pain, chronic pain, muscle tremors, muscle spasms, seizures, convulsions and/or epilepsy. The nature of the agents is described in more detail in the present disclosure.

In one embodiment, the POZ polymer contains at least one reactive group capable of forming a linkage with an agent or a linking group.

The linkage (whether a direct linkage or a linkage utilizing a linking group) between the polymer and agent may be formed between any reactive group on the polymer backbone and any reactive group on the agent. The linkage between the linking group and the polymer may be formed on a terminal end of the polymer. Alternatively, the linkage between the linking group and the polymer may be formed using a side chain group of the polymer (referred to herein as a "pendent" position). Furthermore, the linkage (whether a direct linkage or a linkage utilizing a linking group) may include components of the reactive group that was originally present on the polymer or the agent. Suitable linking groups are described herein.

Exemplary R groups include, but are not limited to, hydrogen, alkyl and substituted alkyl. In one embodiment, the initiating group is an alkyl group, such as a C1 to C4 alkyl group. In a specific embodiment of the foregoing, the initiating group is a methyl group. In another embodiment, the initiating group is H. In yet another embodiment, the initiating group is selected to lack a functional group. Additional exemplary initiating groups are disclosed in U.S. Pat. Nos. 7,943,141, 8,088,884, 8,110,651 and 8,101,706, application Ser. Nos. 13/003,306, 13/549,312 and 13/524,994, each of which is incorporated herein by reference for such teachings.

In a particular embodiment, the POZ conjugate of the present disclosure may be represented by the general formula IIA, wherein the linkage between the agent and the polymer is formed at the "pendent" position.

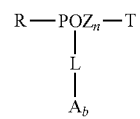

wherein
R, POZ, n, b, L and A are as defined in the description of formula II; and
T is a terminating group.

In one embodiment, T is a terminating nucleophile. In one embodiment, T is Z—B-Q, wherein Z is S, O, or N; B is an optional linking group; and Q is a terminating nucleophile or a terminating portion of a nucleophile. In certain embodiments Q is inert (i.e., does not contain a functional group); in other embodiments, Q contains a second functional group.

Exemplary B groups include, but are not limited to, alkylene groups. In a particular embodiment, B is —(CH$_2$)$_y$— where y is an integer selected from 1 to 16. In a particular embodiment, Z is S. POZ conjugates containing a sulfur group as described herein may be prepared by terminating the POZ cation with a mercaptide reagent, such as, but not limited to, a mercapto-ester (for example, —S—CH$_2$CH$_2$—CO$_2$CH$_3$) or mercapto-protected amine (for example, —S—CH$_2$CH$_2$—NH— tBoc). Such POZ conjugates provide for effective, large-scale purification by ion-exchange chromatography (to remove secondary amines), as well as allowing for control of polydispersity values (with polydispersity values of 1.10 or less) and for the creating of conjugates with higher molecular weight POZ polymers. In another embodiment, Z is N. In a further embodiment, Z is O.

As stated above, Q may be inert or may contain a functional group. When Q contains a functional group, exemplary groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). When Q is an inert group, any inert group may be used, including, but not limited to —C$_6$H$_5$.

In one embodiment, L is present and contains a cleavable moiety, Z is S, B is —CH$_2$CH$_2$— and Q is —COOH. In another specific embodiment L is present and contains a cleavable moiety, Z is O, B is —CH$_2$CH$_2$— and Q is —COOH. In still another specific embodiment L is present and contains a cleavable moiety, Z is N, B is —CH$_2$CH$_2$— and Q is —COOH.

In another particular embodiment, the POZ conjugate of the present disclosure may be represented by the general formula IIB, wherein the linkage between the agent and the polymer is formed at the "pendent" position.

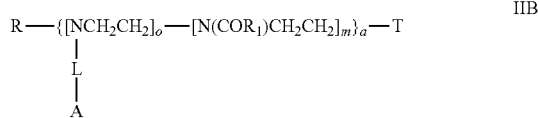

wherein
R, L, A are as defined in the description of formula II and T (including the definitions of Z, B and Q) is as described in the description of formula IIA;
R$_1$ is a non-reactive group;
a is ran which indicates a random copolymer or block which indicates a block copolymer
o is an integer from 1 to 50; and
m is an integer from 1 to 1000.

In one embodiment, R$_1$ is an alkyl or a substituted alkyl. In a particular embodiment, R$_1$ is methyl, ethyl, propyl or butyl. Exemplary R$_1$ groups are described in U.S. Pat. Nos. 7,943,141, 8,088,884, 8,110,651 and 8,101,706, application Ser. Nos. 13/003,306, 13/549,312 and 13/524,994, each of which is incorporated herein by reference for such teachings.

In a particular embodiment, T is Z—B-Q and the compound is represented by the general formula IIC.

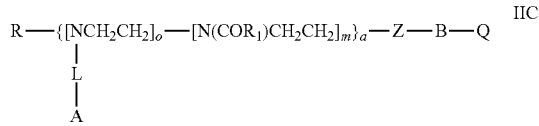

wherein
R, L, A are as defined in the description of formula II and Z, B and Q are as described in the description of formula IIA and R$_1$ is as defined in the description for the formula IIB;

In one embodiment, L is present and contains a cleavable moiety, Z is S, B is —CH$_2$CH$_2$— and Q is —COOH. In another specific embodiment L is present and contains a cleavable moiety, Z is O, B is —CH$_2$CH$_2$— and Q is —COOH. In still another specific embodiment L is present and contains a cleavable moiety, Z is N, B is —CH$_2$CH$_2$— and Q is —COOH.

In one embodiment of the conjugates of formula IIB and IIC, the POZ conjugate is formed by reacting a POZ polymer of the general formula R—{[N(COX)CH$_2$CH$_2$]$_o$—[N(COR$_1$)CH$_2$CH$_2$]$_m$}$_a$—with an agent or a linking group. In the general formula above, X represents a pendent moiety containing a functional group capable of forming a linkage with an agent or a linking group. As a result of the linkage being formed, the COX portion of the POZ polymer becomes a part of the linkage linking the polymer and the agent. Exemplary functional groups for X include, but are not limited to, alkene, alkyne, aralkyl, heterocycloalkyl, amine, oxyamine, aldehyde, ketone, acetal, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). X may comprise a linking portion that links the functional group to the polyoxazoline polymer. Exemplary linking portions include alkylene groups. In certain cases, the alkylene group is a C$_1$-C$_{15}$ alkylene group.

In a particular embodiment, X contains an alkyne group and the agent or linking group contains an azido group. In another embodiment, X contains an azido group and the agent or linking group contains an alkyne group. In still a further embodiment, X contains a carboxylic acid group and the linking group contains a phenolic group.

In the embodiments shown in FIGS. IIB and IIC, the number of agents and linking groups attached to the polymer conjugate is defined by the variable o as this polymer block contains the pendent moiety containing a functional group capable of forming a linkage with an agent or a linking group. In one embodiment, the number of agents and linking groups attached to the polymer conjugate is equal to the value of the variable o. In another embodiment, the number of agents and linking groups attached to the polymer conjugate is less than the value of the variable o.

In the embodiments described above for the general formulas I, II, IIA, IIB and IIC, specific linking groups are as described below. For the sake of clarity any linking group described herein may be used in the general formulas described above.

Linking Group

In the embodiments described above, the agent is linked to the polymer via a releasable linkage. In one embodiment, a linking group is provided between the polymer and the agent, the linking group containing a cleavable moiety. The linking group is capable of forming a releasable linkage between the polymer and the agent. In other words the linking group contains a linkage that can be cleaved in vivo in a subject after administration of a polymer conjugate of the present disclosure to the subject. In one embodiment, the cleavable moiety is cleaved by a chemical reaction. In aspect of this embodiment, the cleavage is by reduction of an easily reduced group, such as, but not limited to, a disulfide. In one embodiment, the cleavable moiety is cleaved by a substance that is naturally present or induced to be present in the subject. In an aspect of this embodiment, such a substance is an enzyme or polypeptide. Therefore, in one embodiment, the cleavable moiety is cleaved by an enzymatic reaction. In one embodiment, the cleavable moiety is cleaved by a combination of the foregoing. The linking group may contain portions of the polymer and/or portions of the agent as such portions have reacted to form the linking group as discussed below.

Exemplary releasable moieties include, but are not limited to, esters, carboxylate esters (—C(O)—O—), carbonate esters (—O—C(O)—O—), carbamates (—O—C(O)—NH—) and amides (—C(O)—NH—); other releasable moieties are discussed herein. In a particular embodiment, the cleavable moiety is an ester. In another particular embodiment, the cleavable moiety is a carbonate ester or a carboxylate ester. In addition, the linking group may be a naturally occurring amino acid, a non-naturally occurring amino acid or a polymer containing one or more naturally occurring and/or non-naturally occurring amino acids. The linking group may include certain groups from the polymer chain and/or the agent.

In the descriptions below, the polymer is assumed to be a polyoxazoline polymer for the purpose of exemplification. However, the reactions below are equally applicable to other polymer types.

In one embodiment, the linking group is a di-substituted triazole that contains a cleavable moiety in one of the $R_3$ or $R_4$ groups. In one embodiment, the cleavable moiety is present in the $R_4$ group. In a specific embodiment, the di-substituted triazole has the structure:

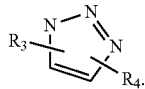

In another embodiment, the di-substituted triazole has the structure:

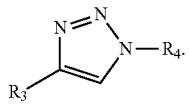

In each of the foregoing structures:

$R_3$ is a linker linking the triazole moiety to the polymer chain. $R_3$ may be defined in part by the functional group on the polymer chain; in other words, $R_3$ may contain a part of the functional group on the polymer chain. In one embodiment, $R_3$ is —C(O)—$R_5$—, where $R_5$ is absent or is a substituted or unsubstituted alkyl from 1 to 10 carbons in length. $R_4$ is a linker linking the triazole moiety to the agent. $R_4$ may be defined in part by the functional group on the agent; in other words, $R_4$ may contain a part of the functional group on the agent. In one embodiment, $R_4$ is —$R_6$—$R_7$—$R_8$—, where $R_6$ is a substituted or unsubstituted alkyl, substituted or unsubstituted aralkyl or a oligo(ethylene oxide) (for example, —(CH$_2$CH$_2$O)$_d$— where d is 1-10 or 1-4), $R_7$ is a group containing the cleavable moiety or a portion of cleavable moiety and $R_8$ is absent or O, S, CR$_c$, or NR$_c$, where $R_c$ is H or substituted or unsubstituted alkyl. In certain embodiments, $R_7$ and $R_8$ may combine to form the cleavable moiety. In one embodiment, $R_7$ is —$R_a$—(O)—$R_b$—, —$R_a$—O—C(O)—$R_b$—, —$R_a$—C(O)—NH—cyclic-O—C(O)—$R_b$— (where cyclic represents substituted or unsubstituted aryl, heterocylalkyl, heterocycle or cycloalkyl), —$R_a$—C(O)—NH—(C$_6$H$_4$)—O—C(O)—$R_b$—, —$R_a$—C(O)—$R_b$—, —$R_a$—C(O)—O—$R_b$—, —$R_a$—O—C(O)—O—$R_b$—, —$R_a$—O—C(O)—NR$_{15}$—$R_b$— (where $R_{15}$ is a is H or a substituted or unsubstituted C1-C5 alkyl), —$R_a$—CH(OH)—O—$R_b$—, —$R_a$—S—S—$R_b$—, —$R_a$—O—P(O)(OR$_{11}$)—O—$R_b$— (where $R_{11}$ is H or a substituted or unsubstituted C$_1$-C5 alkyl), or —$R_a$—C(O)—NR$_{15}$—$R_b$— (where $R_{15}$ is a is H or a substituted or unsubstituted C1-C5 alkyl), where $R_a$ and $R_b$ are each independently absent or substituted or unsubstituted alkyl. In another embodiment, $R_a$ and $R_b$ are each independently absent or a C2-C16 substituted or unsubstituted alkyl. In one embodiment of the foregoing, $R_6$ is a straight chain substituted or unsubstituted C1-C16 alkyl or a branched substituted or unsubstituted C1-C16 alkyl, $R_7$ is —$R_a$—C(O)—O—$R_b$— and $R_8$ is absent. In one embodiment of the foregoing, $R_6$ is a straight chain substituted or unsubstituted C1-C4 alkyl or a branched substituted or unsubstituted C1-C4 alkyl, $R_7$ is —$R_a$—C(O)—O—$R_b$— and R8 is absent. In one embodiment of the foregoing, $R_6$ is, —CH$_2$—, —CH$_2$—CH$_2$—, or —CH$_2$(CH$_3$)— and $R_7$ is —C(O)—O— and $R_8$ is absent.

In a particular embodiment, $R_3$ is —C(O)—(CH$_2$)$_3$ and $R_4$ is —CH$_2$—C(O)—O—, —CH$_2$—CH$_2$—C(O)—O— or —CH(CH$_3$)—C(O)—O—.

In a particular embodiment, $R_3$ is —C(O)—(CH$_2$)$_3$ and $R_4$ is —CH$_2$—CH$_2$—O—C(O), —CH$_2$—CH$_2$—CH$_2$—O—C(O), —CH$_2$—CH$_2$—CO—NH—(C$_6$H$_4$)—O—C(O)— or —(CH$_2$CH$_2$O)$_d$—C(O)—, where d is 1-10.

In another embodiment, the linking group has the structure $R_9$—Y—$R_{10}$, where Y is a cleavable moiety and $R_9$ and $R_{10}$ are each groups linking Y to the polymer conjugate and the agent, respectively. R9 and $R_{10}$ may be the same of different. In one embodiment, $R_9$ and $R_{10}$ are each independently absent or substituted or unsubstituted alkyl, substituted or unsubstituted aralkyl or a oligo(ethylene oxide) (for example, —(CH$_2$CH$_2$O)$_d$— where d is 1-10 or 1-4). In another embodiment, $R_9$ and $R_{10}$ are each independently absent or a C2-C16 substituted or unsubstituted alkyl.

In one embodiment of the foregoing, the linking group Y is $R_9$—(O)—$R_{10}$—, —$R_9$—O—C(O)—$R_{10}$—, —R9—C(O)—NH-cyclic-O—C(O)—$R_{10}$— (where cyclic represents substituted or unsubstituted aryl, heterocylalkyl, heterocycle or cycloalkyl), —$R_9$—C(O)—NH—(C$_6$H$_4$)—O—C(O)—$R_{10}$—, —$R_9$—C(O)—$R_{10}$—, —$R_9$—C(O)—O—$R_{10}$—, —$R_9$—O—C(O)—O—$R_{10}$—, —$R_9$—O—C(O)—NR$_{16}$—$R_{10}$— (where $R_{16}$ is a is H or a substituted or unsubstituted C1-C5 alkyl), —$R_9$—CH(OH)—O—$R_{10}$—, —$R_9$—S—S—$R_{10}$—, —$R_9$—O—P(O)(OR$_{12}$)—O—$R_{10}$— (where $R_{12}$ is H or a substituted or unsubstituted C1-C5 alkyl), —$R_9$—C(O)—NR$_{16}$—$R_{10}$— (where $R_{16}$ is a is H or a substituted or unsubstituted C1-C5 alkyl) or —$R_9$—[NR$_{16}$—CH($R_{13}$)($R_{14}$)—C(O)]$_q$—$R_{10}$— (where $R_{16}$ is a is H or a substituted or unsubstituted C1-C5 alkyl, $R_{13}$ is H or a C1-C5 alkyl, $R_{14}$ is a side chain group on a naturally occurring or non-naturally occurring amino acid and q is 1-10), where $R_9$ and $R_{10}$ are each independently absent or substituted or unsubstituted alkyl. In another embodiment, $R_9$ and $R_{10}$ are each independently absent, a C1-C16 or a C1-C4 substituted or unsubstituted alkyl.

In one embodiment, the release kinetics of the agent from the polymer is controlled by the nature of the linking group, the nature of the agent, the nature of the polymer, the size of the polymer, the method of delivery or a combination of the foregoing. In one embodiment, the release kinetics of the agent from the polymer is controlled by the nature of the linking group. In one embodiment, the release kinetics of the agent from the polymer is controlled by the nature of the linking group and/or the nature of the agent. In one embodiment, the release kinetics of the agent from the polymer is controlled by the nature of the linking group and/or the nature of the polymer. In one embodiment, the release kinetics of the agent from the polymer is controlled by the nature of the linking group, the nature of the agent and/or the nature of the polymer. Furthermore, diffusion of the free agent can also play a role.

In each of the foregoing, the cleavable moiety may be cleaved chemically under physiological conditions, cleaved by a substance that is naturally present or induced to be present in the subject under physiological conditions or by a combination of the foregoing. In one embodiment, such substance is an enzyme or polypeptide and the cleavage is an enzymatic cleavage.

Agent

The agent may be any agent useful in the treatment of a disease or condition or the diagnosis of a disease or condition. In certain embodiments, the agent is a diagnostic agent or a therapeutic agent. In certain embodiment, the therapeutic agent is an organic small molecule. Furthermore, the agent may be any molecule having a therapeutic or diagnostic application, wherein the agent is capable of forming a linkage with a functional group on a polymer of the present disclosure, such as but not limited to, a POZ polymer, or a linking group linked to a polymer of the present disclosure.

In one embodiment, the agent is useful for the treatment of PD or other diseases or conditions related to dopamine insufficiency in the peripheral or central nervous system. In such an embodiment, the agent may be a dopamine agonists, dopamine antagonist, adenosine $A_{2A}$ receptor antagonists, anticholinergics, monamine oxidase-B inhibitors and catechol-O-methyl transferase (COMT) inhibitors. Exemplary dopamine agonists include, but are not limited to, rotigotine, pramipexole, quinagolide, fenoldopam, apomorphine, 5-OH-DPAT, ropinirole, pergolide, cabergoline, and bromocriptine. Exemplary anticholinergics include, but are not limited to, trihexyphenidyl, biperidin and hyoscyamine. Exemplary monamine oxidase-B inhibitors include, but are not limited to, seligiline and rasagiline. Exemplary COMT inhibitors include, but are not limited to, tolcapone and entacapone. Exemplary Adenosine $A_{2A}$ receptor antagonists include, but not limited to, caffeine, theophylline, istradefylline, and preladenant (B. C. Cook and P. F. Jackson, Adenosine $A_{2A}$ receptor antagonists and Parkinson's disease, ACS Chemical Neuroscience, 2011, 2, 555-567).

PD is a central nervous system disorder resulting from loss of dopamine neurons in the substantia nigra pars compacta. The loss of these neurons in the brain leads to a deficiency of dopamine, a neurotransmitter that is essential for normal coordination and movement. Striatal dopaminergic neurons fire in a random, but continuous fashion due to stable levels of dopamine, allowing for precisely coordinated movements. In PD patients the pre-synaptic neurons degenerate. Administration of dopaminergic agents (dopamine agonists and levo-dopa) in an attempt to control symptoms leads to discontinuous stimulation of the post-synaptic neurons, promoting motor fluctuations that can worsen as the disease progresses (dyskinesias). Early symptoms of dopamine deficiency in PD include tremors, rigidity, bradykinesia, and gait problems. Cognitive and behavioral problems as well as dementia occur in later stages of PD.

While there is no cure, for PD at this time, symptoms of this disease are treated with a variety of drugs aimed at maintaining dopaminergic tone. Drugs currently used for the treatment of PD include levodopa, dopamine agonists, adenosine $A_{2A}$ antagonist, anticholinergics, monamine oxidase-B inhibitors and catechol-O-methyl transferase inhibitors and other drugs. Levodopa is typically reserved for the later stages of PD while the other classes are the drugs of choice in the early stages of PD. There are challenges associated with these drugs. Levodopa can be administered orally, but gastrointestinal tract metabolism and erratic absorption limit bioavailability. For levodopa, bioavailability is less than 10% and even less reaches the brain intact due to peripheral metabolism, including metabolism by decarboxylase enzymes. To address this issue, decarboxylase inhibitors such as carbidopa are co-administered to inhibit peripheral metabolism. Furthermore, the short half-lives of these drugs require frequent dosing of several times daily which results in pulsatile stimulation of striatal dopamine receptors; this may actually accelerate the demise of dopaminergic neurons in the CNS. Low solubility of some of these compounds, with limited oral bioavailability, further complicates their clinical use.

The use of dopamine agonists to treat PD is known in the art. The use of, 2-aminotetralins (a class of compounds with dopamine agonist activity) date back to the late 1980s in disclosures by Horn, A. S. (U.S. Pat. No. 4,722,933, February 1988 and U.S. Pat. No. 4,885,308, December 1989). Horn discussed analogues and small molecule pro-drugs of 2-aminotetralin to treat central nervous system disorders. One such example is rotigotine, a potent dopamine agonist. However, administration of rotigotine has proven to be difficult due to poor solubility in aqueous medium and short half-life. Swart and de Zeeuw report that oral and intraperitoneal bioavailability of rotigotine in rats to be less than 10% (Pharmacokinetics of the dopamine D2 agonist S(−)-2-(N-propyl-N-2-thienylethylamino)-5-hydroxytetralin in freely moving rats. J. Pharm. Sci. 1993 February; 82(2):200-3). Studies in man show that rotigotine has a half-life of 2.5 hours and it is rapidly metabolized to the sulfate and glucuronide analogues at the phenolic group. In an effort to improve the characteristics and oral bioavailability of these dopamine agonists, Stefano, Sozio, and Cerasa (Molecules 2008, 13: 46-68) prepared acetyl, propionyl, isobutyryl and carbamate pro-drugs. Esters of this type, however, would not be expected to improve water solubility and the improvement in duration in action was marginally increased from 3 to 4 hours to 11 to 15 hours. A transdermal patch was developed to address the suboptimal pharmacokinetics. This approach allows for 24 hours of delivery and improved bioavailability, but stability issues relating to poor solubility and crystallization in the patch resulted in this product's withdrawal from the U.S. market until formulation issues were addressed.

Ropinirole is another non-ergoline dopamine agonist that is delivered orally and has a half-life of 3 to 6 hours in man. Higher doses are required to achieve clinical benefit due to hepatic and renal metabolism. In addition, the once-a-day tablet dose generates undesired peak and troughs in blood concentration.

In another embodiment, the agent is useful for the treatment of a disorder characterized by excessive GABA re-uptake or GABA re-uptake. In one embodiment, the agent is useful in the treatment of an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy. In such an embodiment, the agent may be a GABA re-uptake inhibitor. GABA (gamma-aminobutyric acid) is a neurotransmitter produced in the central nervous system that is thought to be the major inhibitory neurotransmitter. Inhibition of its re-uptake by certain small molecules (for example, tiagabine and nipecotic acid) potentiate its activity in the post-synaptic neuron and potentiate GABAergic neurotransmission.

Therefore, there is a need in the art for new compositions for the treatment of PD and other conditions relating to dopamine deficiency as well as for the treatment of an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy.

The present disclosure provides conjugates containing a polymer, such as those described herein, and an agent useful in the treatment of PD or other diseases or conditions related to dopamine insufficiency in the peripheral or central nervous system as well as the treatment of anxiety disorders, social anxiety disorders, panic disorders, neuropathic pain (which includes usefulness in poorly understood disorders like fibromyalgia), chronic pain, muscle tremors, muscle spasms, seizures, convulsions and/or epilepsy. The foregoing disorders will benefit from a polymer approach for sustained pharmacokinetics, increased bioavailability and ease of administration.

The polymer conjugates of the present disclosure have been exemplified by POZ-rotigotine, POZ-tiagabine, POZ-ropinirole, PEG-rotigotine, PEG-tiagabine, and dextran-rotigotine. Other agents and polymers, including those disclosed herein, are also useful in the conjugates of the present disclosure provided such agents and polymers have, or can be modified to contain, appropriate functionality for linkage to the water soluble polymer.

Dopamine Agonists

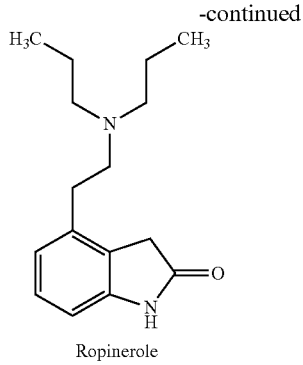
Ropinerole

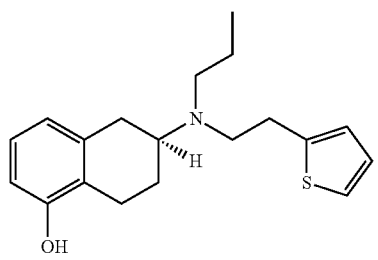
Rotigotine

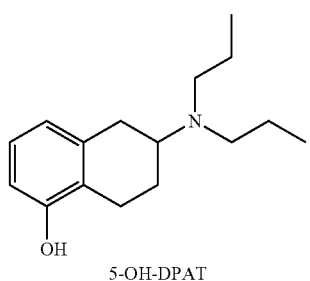
5-OH-DPAT

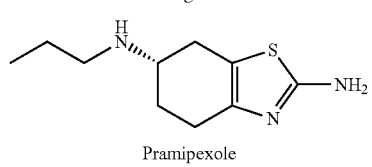
Pramipexole

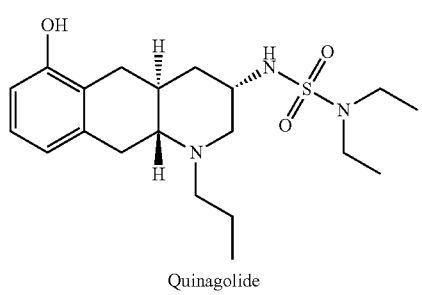
Quinagolide

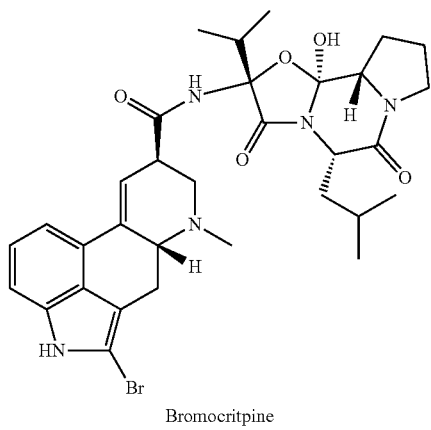
Bromocritpine

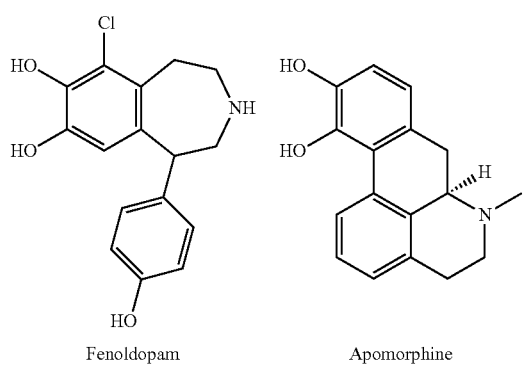
Fenoldopam   Apomorphine

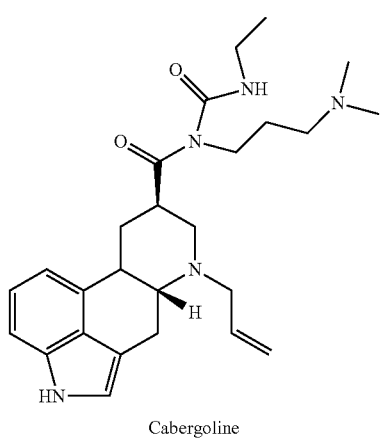
Cabergoline

-continued

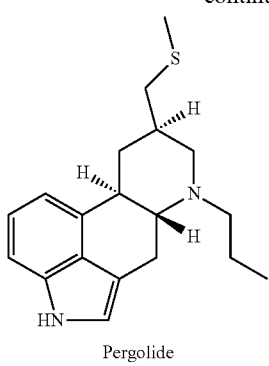

Pergolide

Other classes of drugs useful in the treatment of PD, such as, but not limited to, anticholinergics (such as, but not limited to, trihexyphenidyl, biperidin and hyoscyamine), monamine oxidase-B inhibitors (such as, but not limited to, seligiline and rasagiline), catechol-O-methyl transferase (COMT) inhibitors (such as, but not limited to, tolcapone and entacapone) and adenosine $A_{2A}$ receptor antagonists (such as, but not limited to, preladenant, theophylline and istradefylline) are also useful in the conjugates and methods of treatment described herein.

Anticholinergics

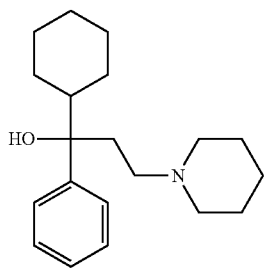

Trihexyphenidyl

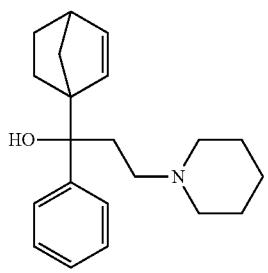

Biperidin

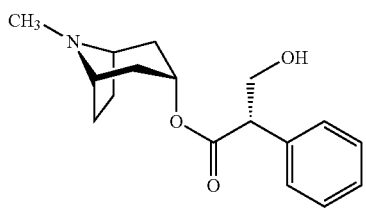

Hyoscyamine

Monamine oxidase-B inhibitors

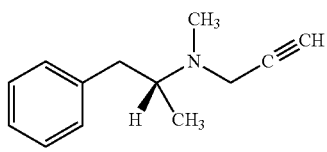

Seligiline

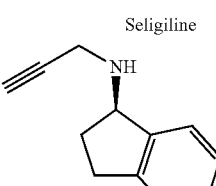

Rasagiline

Catechol-O-methyl transferase inhibitors

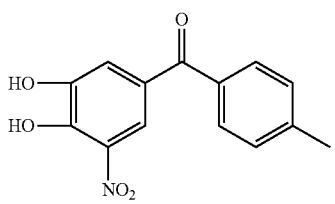

Tolcapone

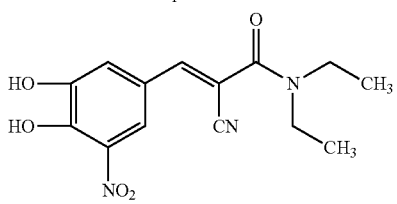

Entacapone

Adenosine $A_{2A}$ receptor antagonists

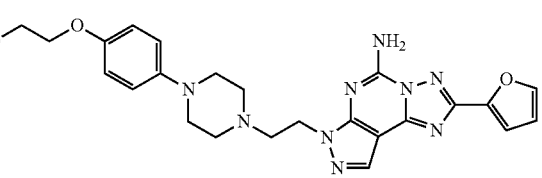

Preladenant

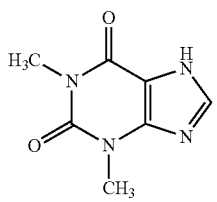

Theophylline

Istradefylline

For clarity, the agent may be any of the foregoing classes of compounds or a compound of another class that have appropriate chemical functionality to form a releasable linkage with a water-soluble polymer or linking group of the present disclosure. The foregoing examples are presented by way of exemplification and are not intended to be limiting.

Furthermore, the agent may be used to treat a variety of diseases or conditions. The present specification described certain agents useful for the treatment of PD and other diseases or conditions related to dopamine insufficiency in the peripheral or central nervous system and agents useful for the treatment of anxiety disorders, social anxiety disorders, panic disorders, neuropathic pain (which includes usefulness in poorly understood disorders like fibromyalgia), chronic pain, muscle tremors, muscle spasms, seizures, convulsions and/or epilepsy in order to illustrate the teachings of the present disclosure. However, the choice of agent should not be limited to the treatment of the exemplified diseases or conditions. Any agent that would benefit from a polymer approach for sustained pharmacokinetics, increased bioavailability and ease of administration may also be used. The foregoing examples are presented by way of exemplification and are not intended to be limiting.

Control of Release of Agent

The present disclosure provides polymer conjugates where the release kinetics of the agent from the water-soluble polymer can be controlled by varying one or more parameters of the polymer conjugate. Such parameters include, but are not limited to, the nature of the linking group, the nature of the polymer, the nature of the agent, the size of the polymer, and varying the method of delivery (mode of administration). Tables 1-4 provide experimental data on control of cleavage rates by varying the nature of the linker, drug and polymer.

In one embodiment, the release kinetics of the agent from the water-soluble polymer is controlled by the nature of the linking group. In another embodiment, the release kinetics of the agent from the water-soluble polymer is controlled by the nature of the polymer. In another embodiment, the release kinetics of the agent from the water-soluble polymer is controlled by the nature of the agent. In another embodiment, the release kinetics of the agent from the water-soluble polymer is controlled by the size of the polymer. In another embodiment, the release kinetics of the agent from the water-soluble polymer is controlled by the mode of administration. In still a further embodiment, the release kinetics of the agent from the water-soluble polymer is controlled by the nature of the linking group and/or the nature of the agent. In still a further embodiment, the release kinetics of the agent from the water-soluble polymer is controlled by the nature of the linking group and/or the nature of the polymer. In still a further embodiment, the release kinetics of the agent from the water-soluble polymer is controlled by the nature of the linking group, the nature of the agent and/or the nature of the polymer.

As discussed above, the release kinetics of the agent from the water-soluble polymer (i.e., rate of cleavage of the linking group) is controlled, in one embodiment, by the nature of the linking group. For example, as shown in Table 1 for cleavage of polymer-triazine-alkyl-$CO_2$— rotigotine, changes in the alkyl group affect the release of the drug rotigotine. Similarly, the nature of the polymer has an effect on the release kinetics of the agent from the water-soluble polymer. For example, rotigotine is released much more slowly from POZ than from PEG or modified dextran (Table 1). Slower release of the agent avoids a rapid spike in drug concentration in the blood followed by rapid clearance. Such a profile results in sustained release of drug over time. In some instances a single administration of a polymer conjugate of the present disclosure can provide for therapeutically effective concentrations of the agent in the blood over a period of several days to weeks.

Table 2 illustrates that rate of release of an agent from a polymer conjugate of the present disclosure is affected by the drug itself. Variation of polymer and linker can be used to tune the release rate of each agent within a certain range determined by the agent. Table 3 illustrates that varying the molecular weight of polymer and the number of pendents has no effect on rate of release of the agent (irinotecan in this case) from the polymer.

In addition, the size of the polymer contained in the polymer conjugate impacts the rate of release of the agent into systemic circulation. In one embodiment, the size of the polymer impacts the rate of release of the agent into systemic circulation without affecting the rate of cleavage of the linking group. For example, with subcutaneous administration, the rate of release of the polymer conjugate from the subcutaneous compartment is controlled, at least in part, by the size of the polymer. As polymer size increases, the rate of systemic clearance from the subcutaneous compartment decreases. As polymer size decreases, the rate of systemic clearance from the subcutaneous compartment increases. As a result, the entrance of the polymer into the systemic circulation, and subsequent cleavage of the linking group to release the agent, can be controlled.

Furthermore, the route of administration affects the rate of release of the agent into the systemic circulation. Administration by the subcutaneous route results in a slower and sustained release of the agent into the systemic circulation compared to other routes of administration, such as for example, intravenous administration. Administration via the intravenous route results in a more rapid release of the agent into the systemic circulation. These concepts are illustrated in Examples 31-32 and FIGS. 2-4. Example 32 shows similar results for pharmacokinetics in monkeys, and Example 31 shows similar results for pharmacodynamics for rats.

Figure 2:
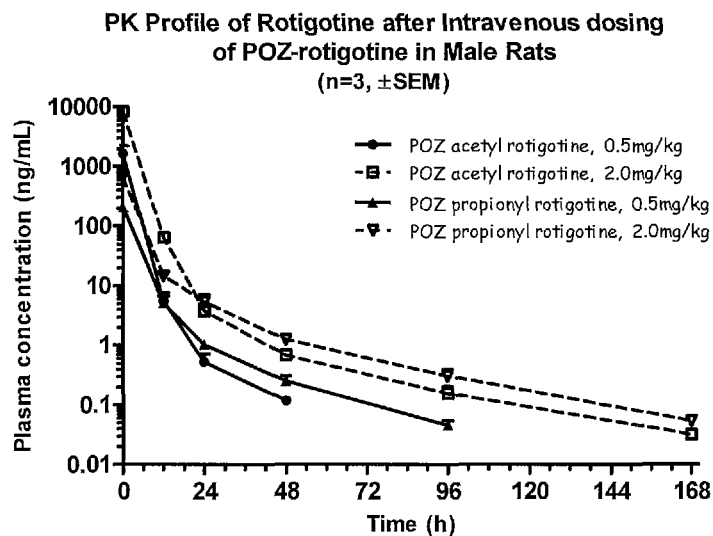
FIG. 2 shows the pharmacokinetic profile of rotigotine after intravenous dosing of POZ rotigotine in male Sprauge-Dawley rats.
Figure 3:
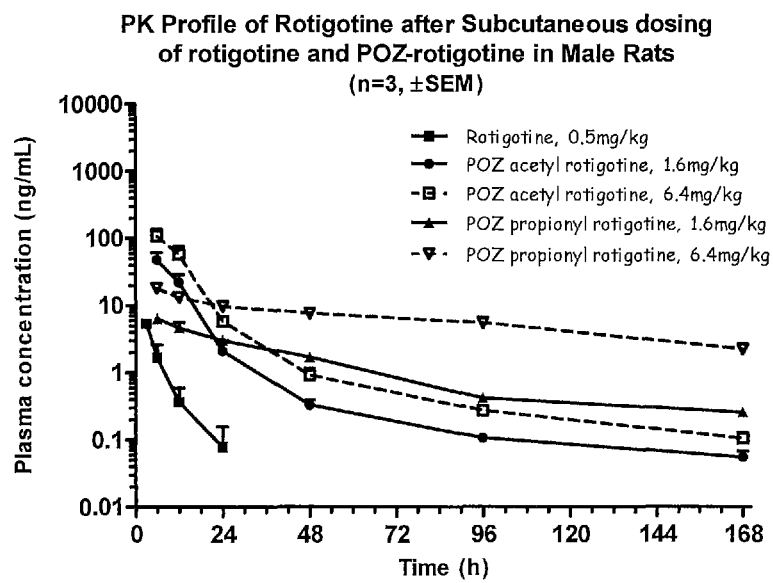
FIG. 3 shows the pharmacokinetic profile of rotigotine after subcutaneous dosing of POZ rotigotine in male Sprauge-Dawley rats.

The plasma concentration of rotigotine (ng/mL) after intravenous and subcutaneous injection of POZ-rotigotine in rats is described in Example 31 and shown in FIGS. 2 and 3, respectively. These results show that use of POZ conjugates of rotigotine, whether dosed intravenously (IV) or subcutaneously (SC), will reduce the clearance rate of rotigotine from the blood when compared to the parent molecule alone. The terminal plasma half-life (t½) for rotigotine, POZ acetyl rotigotine and POZ propyl rotigotine was 2.8, 16 and 60 h, respectively. However, there is a difference in the PK profiles for the POZ-conjugates POZ acetyl rotigotine and POZ propyl rotigotine when route of administration is compared (IV vs SC). POZ-conjugates delivered IV are generally cleared in a bi-phasic pattern with little difference between POZ acetyl rotigotine and POZ propyl rotigotine. However, when POZ acetyl rotigotine and POZ propyl rotigotine are compared following SC administration there is a marked difference. POZ acetyl rotigotine has essentially the same PK profile when delivered either SC or IV. POZ propyl rotigotine has a markedly prolonged PK profile that is near "zero order" kinetics. The nature of the linker plays a role in the release of the agent, in this case rotigotine, and the levels measured in rat plasma from day 1 to day 7 are higher for the propyl linker than the acetyl linker. The initial plasma concentrations of rotigotine during the first 12 hours are lower for POZ propyl rotigotine when compared to the POZ acetyl rotigotine conjugate. At 12 hours, the C. values of plasma rotigotine were 6 ng/mL for POZ propyl rotigotine versus for 48 ng/mL for the POZ acetyl rotigotine when dosed SC at the dose of 1.6 mg/kg.

Figure 4:
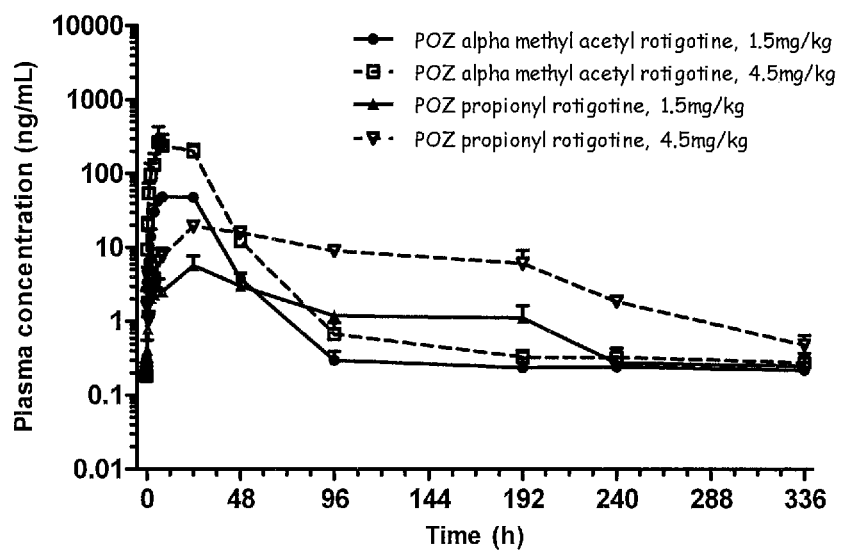
FIG. 4 shows the pharmacokinetic profile of rotigotine after subcutaneous dosing of POZ-rotigotine in female Cynomolgus monkeys.

The plasma concentration of rotigotine (ng/mL) after subcutaneous injection of POZ rotigotine in normal, treatment-naïve female macaques monkeys is described in Example 32 and shown in FIG. 4. Animals were randomly assigned into four treatment groups, each N=3. Animals received one subcutaneous dose of either POZ alpha methyl acetyl rotigotine or POZ propyl rotigotine at doses of either 1.5 mg/kg or 4.5 mg/kg (based on rotigotine equivalents). The plasma concentration of rotigotine (ng/mL) after subcutaneous injection is shown in FIG. 4. These results show that POZ conjugates of rotigotine will reduce the clearance rate of rotigotine from the blood. The average terminal plasma half-life (t½) of rotigotine from POZ alpha methyl acetyl rotigotine and POZ propionyl rotigotine was 9 and 60 h, respectively. Once again, the POZ propyl rotigotine has a markedly prolonged PK profile that is near "zero order" kinetics. The initial plasma concentrations of rotigotine during the first 12 hours are lower for POZ propyl rotigotine when compared to the POZ alpha methyl acetyl rotigotine compound. From 4 to 192 hours, the average $C_{ss}$, value of plasma rotigotine was between 1 and 6 ng/mL for POZ propyl rotigotine at the 1.5 mg/kg dose.

These results show that controlled delivery of an agent can be "tuned" to release the agent with a desired release profile without an initial burst effect based on the nature of the releasable linker, the nature of the polymer, the nature of the agent, the route of administration (e.g. subcutaneous vs. IV injection) or a combination of the foregoing.

Viscosity and Drug Loading

Viscosity and drug loading are additional factors that must be considered when formulating a suitable polymer-drug conjugate for treating disease. As shown in Example 30 and Table 5, higher molecular weight polymer conjugates are increasingly viscous when in solution, and thus can become too viscous for effective injection. The nature of the polymer is also a factor in this consideration. For example, POZ conjugates are less viscous than 4-arm PEG conjugates of the same molecular weight. Similarly the PEG-dendrimer is less viscous than the 4-arm PEG conjugate. Additionally, one must consider the number of agents that can be attached to the polymer backbone. For example, the POZ-20K polymer with 10 pendents carries more molecules of the agent than the 4-arm PEG 20K polymer, and thus one can inject a lower mass of POZ conjugate and achieve the same amount of agent delivered to the subject. Thus viscosity and drug loading, as well as the factors affecting release rates into the blood (discussed in above) must be taken into account when formulating a suitable polymer-drug composition for treating disease. In one embodiment, an acceptable polymer-drug conjugate from a viscosity standpoint is syringeabile through a 28 G needle. In one embodiment, an acceptable polymer-drug conjugate from a viscosity standpoint has a viscosity (as measured in mPas) of less than or equal to 210, 175, 160, 150, 125 or 75.

Methods of Treatment

The present disclosure provides polymer conjugates comprising a water-soluble polymer and an agent, the agent linked to the polymer by a releasable linker. The present disclosure further shows that the release of the agent from the polymer conjugate can be controlled. In one aspect, the agent is delivered with a pharmacokinetic profile that lacks peaks and troughs as seen in prior art treatments. In one aspect, a near steady state release of the agent from the polymer conjugate is achieved over a period of time from days to weeks. In one embodiment, such a release profile provides a therapeutically effective concentration of the agent over such time period. As a result, the polymer conjugates of the present disclosure are useful for treating human disease through appropriate selection of the agent. Furthermore, the polymer conjugates of the present disclosure allow for less frequent administration as compared to the art to achieve therapeutically effective concentrations of the agent in a subject. In one embodiment, polymer conjugates of the present disclosure are administered once a day, once every other day, once a week or at other desired intervals.

In one embodiment, a method of treating a disease state or condition is disclosed. Such method comprises the step of administering to the subject an amount of a polymer conjugate of the present disclosure to a subject. In one embodiment, such disease state or condition is PD. In one embodiment, such disease state or condition is a disease or condition related to dopamine insufficiency in the peripheral or central nervous system. In one embodiment, such disease or condition is restless leg syndrome. In one embodiment, such disease state or condition is an anxiety disorder. In one embodiment, such disease state or condition is a social anxiety disorder. In one embodiment, such disease state or condition is a panic disorder. In one embodiment, such disease state or condition is a seizure disorder. In one embodiment, such disease state or condition is neuropathic pain. In one embodiment, such disease state or condition is fibromyalgia. In one embodiment, such disease state or condition is convulsions. In one embodiment, such disease state or condition is epilepsy. In one embodiment, such disease state or condition is muscle tremors. In one embodiment, such disease state or condition is muscle spasms.

In such embodiments, any polymer conjugate described herein may be used and the agent may be selected based on the disease or condition to be treated. In a particular embodiment, the polymer is a POZ polymer. In another embodiment, the polymer is a PEG polymer. In still another embodiment, the polymer is a dextran polymer or a dextran polymer modified by oxidation.

In one embodiment, the present disclosure provides a method of treating a disease state or condition is a disease or condition related to dopamine insufficiency in the peripheral or central nervous system. Such method comprises the step of administering to the subject an amount of a polymer conjugate of the present disclosure to a subject.

In one embodiment, the disease or condition related to dopamine insufficiency is PD. Therefore, the present disclosure provides a method of treating PD. Such method comprises the step of administering to the subject an amount of a polymer conjugate of the present disclosure to a subject.

In one embodiment, the disease or condition related to dopamine insufficiency is restless leg syndrome. Therefore, the present disclosure provides a method of treating restless leg syndrome. Such method comprises the step of administering to the subject an amount of a polymer conjugate of the present disclosure to a subject.

Any polymer conjugate of the present disclosure may be used in the methods above. In a particular embodiment, the following polymer conjugates may be used in such methods of treatment.

In one embodiment, the polymer conjugate is a poly (oxazoline) polymer conjugate and the agent is a compound useful in the treatment of PD or another disease or condition related to dopamine insufficiency in the peripheral or central nervous system.

In one embodiment, the polymer conjugate is a poly(oxazoline) polymer conjugate and the agent is a dopamine agonist, adenosine $A_{2A}$ antagonist, anticholinergic, monamine oxidase-B inhibitor or catechol-O-methyl transferase (COMT) inhibitor.

In one embodiment, the polymer conjugate is a poly(oxazoline) polymer conjugate and the agent is rotigotine, pramipexole, quinagolide, fenoldopam, apomorphine, 5-OH-DPAT, ropinirole, pergolide, cabergoline, or bromocriptine.

In one embodiment, the polymer conjugate is a poly(oxazoline) polymer conjugate and the agent is rotigotine or (−)rotigotine.

In one embodiment, the polymer conjugate is a poly(oxazoline) polymer conjugate and the agent is ropinirole.

In one embodiment, the polymer conjugate is a poly(oxazoline) polymer conjugate and the agent is trihexyphenidyl, biperidin or hyoscyamine.

In one embodiment, the polymer conjugate is a poly(oxazoline) polymer conjugate and the agent is seligiline or rasagiline.

In one embodiment, the polymer conjugate is a poly(oxazoline) polymer conjugate and the agent is tolcapone or entacapone.

In one embodiment, the polymer conjugate is a poly(oxazoline) polymer conjugate and the agent is caffeine, theophylline, istradefylline or preladenant.

In the foregoing embodiments where the polymer conjugate is a poly(oxazoline) polymer conjugate, the poly(oxazoline) polymer conjugate may have the general formula as shown for compound II, IIA, IIB or IIC. In one embodiment, the polymer conjugate is a poly(oxazoline) polymer conjugate having the general formula as shown for compound IIC or an example herein.

In one embodiment, the polymer conjugate is a polyethylene glycol polymer conjugate and the agent is a compound useful in the treatment of PD or another disease or condition related to dopamine insufficiency in the peripheral or central nervous system.

In one embodiment, the polymer conjugate is a polyethylene glycol polymer conjugate and the agent is a dopamine agonist, adenosine $A_{2A}$ antagonist, anticholinergic, monamine oxidase-B inhibitor or catechol-O-methyl transferase (COMT) inhibitor.

In one embodiment, the polymer conjugate is a polyethylene glycol polymer conjugate and the agent is rotigotine, pramipexole, quinagolide, fenoldopam, apomorphine, 5-OH-DPAT, ropinirole, pergolide, cabergoline, or bromocriptine.

In one embodiment, the polymer conjugate is a polyethylene glycol polymer conjugate and the agent is rotigotine or (−)rotigotine.

In one embodiment, the polymer conjugate is a polyethylene glycol polymer conjugate and the agent is ropinirole.

In one embodiment, the polymer conjugate is a polyethylene glycol polymer conjugate and the agent is trihexyphenidyl, biperidin or hyoscyamine.

In one embodiment, the polymer conjugate is a polyethylene glycol polymer conjugate and the agent is seligiline or rasagiline.

In one embodiment, the polymer conjugate is a polyethylene glycol polymer conjugate and the agent is tolcapone or entacapone.

In one embodiment, the polymer conjugate is a polyethylene glycol polymer conjugate and the agent is caffeine, theophylline, istradefylline or preladenant.

In the foregoing embodiments, when the polymer is a polyethylene glycol polymer, the polyethylene glycol polymer may be a multi-arm polymer, including a 4-arm polymer, a difuncitonal polymer or a dendrimer.

In the foregoing embodiments where the polymer conjugate is a polyethylene glycol polymer conjugate, the polyethylene glycol polymer conjugate may have the general formula as shown for compound I or an example herein.

In one embodiment, the polymer conjugate is a dextran or oxidized dextran polymer conjugate and the agent is a compound useful in the treatment of PD or another disease or condition related to dopamine insufficiency in the peripheral or central nervous system.

In one embodiment, the polymer conjugate is a dextran or oxidized dextran polymer conjugate and the agent is a dopamine agonist, adenosine $A_{2A}$ antagonist, anticholinergic, monamine oxidase-B inhibitor or catechol-O-methyl transferase (COMT) inhibitor.

In one embodiment, the polymer conjugate is a dextran or oxidized dextran polymer conjugate and the agent is rotigotine, pramipexole, quinagolide, fenoldopam, apomorphine, 5-OH-DPAT, ropinirole, pergolide, cabergoline, or bromocriptine.

In one embodiment, the polymer conjugate is a dextran or oxidized dextran polymer conjugate and the agent is rotigotine or (−)rotigotine.

In one embodiment, the polymer conjugate is a dextran or oxidized dextran polymer conjugate and the agent is ropinirole.

In one embodiment, the polymer conjugate is a dextran or oxidized dextran polymer conjugate and the agent is trihexyphenidyl, biperidin or hyoscyamine.

In one embodiment, the polymer conjugate is a dextran or oxidized dextran polymer conjugate and the agent is seligiline or rasagiline.

In one embodiment, the polymer conjugate is a dextran or oxidized dextran polymer conjugate and the agent is tolcapone or entacapone.

In one embodiment, the polymer conjugate is a dextran or oxidized dextran polymer conjugate and the agent is caffeine, theophylline, istradefylline or preladenant.

In the foregoing embodiments where the polymer conjugate is a dextran or oxidized dextran polymer conjugate, the dextran or oxidized dextran polymer conjugate may have the general formula as shown for compound I or an example herein.

In one embodiment, the present disclosure provides a method of treating a disease or condition caused by excessive GABA re-uptake or GABA re-uptake. In another embodiment, the present disclosure provides a method of treating an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy. Such method comprises the step of administering to the subject an amount of a polymer conjugate of the present disclosure to a subject. In such an embodiment, the agent may be a GABA re-uptake inhibitor.

In one embodiment, the disease or condition caused by excessive GABA re-uptake or GABA re-uptake is an anxiety disorder. Therefore, the present disclosure provides a method of treating an anxiety disorder. Such method comprises the step of administering to the subject an amount of a polymer conjugate of the present disclosure to a subject.

In one embodiment, the disease or condition caused by excessive GABA re-uptake or GABA re-uptake is a social anxiety disorder. Therefore, the present disclosure provides a method of treating a social anxiety disorder. Such method comprises the step of administering to the subject an amount of a polymer conjugate of the present disclosure to a subject.

In one embodiment, the disease or condition caused by excessive GABA re-uptake or GABA re-uptake is a panic disorder. Therefore, the present disclosure provides a method of treating a panic disorder. Such method comprises the step of administering to the subject an amount of a polymer conjugate of the present disclosure to a subject.

In one embodiment, the disease or condition caused by excessive GABA re-uptake or GABA re-uptake is a seizure disorder. Therefore, the present disclosure provides a method of treating a seizure disorder. Such method comprises the step of administering to the subject an amount of a polymer conjugate of the present disclosure to a subject.

In one embodiment, the disease or condition caused by excessive GABA re-uptake or GABA re-uptake is muscle tremors. Therefore, the present disclosure provides a method of treating muscle tremors. Such method comprises the step of administering to the subject an amount of a polymer conjugate of the present disclosure to a subject.

In one embodiment, the disease or condition caused by excessive GABA re-uptake or GABA re-uptake is muscle spasms. Therefore, the present disclosure provides a method of treating muscle spasms. Such method comprises the step of administering to the subject an amount of a polymer conjugate of the present disclosure to a subject.

In one embodiment, the disease or condition caused by excessive GABA re-uptake or GABA re-uptake is convulsions. Therefore, the present disclosure provides a method of treating convulsions. Such method comprises the step of administering to the subject an amount of a polymer conjugate of the present disclosure to a subject.

In one embodiment, the disease or condition caused by excessive GABA re-uptake or GABA re-uptake is neuropathic pain. Therefore, the present disclosure provides a method of treating neuropathic pain. Such method comprises the step of administering to the subject an amount of a polymer conjugate of the present disclosure to a subject.

In one embodiment, the disease or condition caused by excessive -GABA re-uptake or GABA re-uptake is fibromyalgia. Therefore, the present disclosure provides a method of treating fibromyalgia. Such method comprises the step of administering to the subject an amount of a polymer conjugate of the present disclosure to a subject.

In one embodiment, the disease or condition caused by excessive. GABA re-uptake or GABA re-uptake is epilepsy. Therefore, the present disclosure provides a method of treating epilepsy. Such method comprises the step of administering to the subject an amount of a polymer conjugate of the present disclosure to a subject.

In one embodiment, the disease or condition caused by excessive GABA re-uptake or GABA re-uptake is muscle spasms. Therefore, the present disclosure provides a method of treating muscle spasms. Such method comprises the step of administering to the subject an amount of a polymer conjugate of the present disclosure to a subject.

In one embodiment, the disease or condition caused by excessive GABA re-uptake or GABA re-uptake is insomnia. Therefore, the present disclosure provides a method of treating insomnia. Such method comprises the step of administering to the subject an amount of a polymer conjugate of the present disclosure to a subject.

Any polymer conjugate of the present disclosure may be used in the methods above. In a particular embodiment, the following polymer conjugates may be used in such methods of treatment.

In one embodiment, the polymer conjugate is a poly(oxazoline) polymer conjugate and the agent is a compound useful in the treatment of an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy.

In one embodiment, the polymer conjugate is a poly(oxazoline) polymer conjugate and the agent is a GABA re-uptake inhibitor.

In one embodiment, the polymer conjugate is a poly(oxazoline) polymer conjugate and the agent is tiagabine or nipecotic acid.

In one embodiment, the polymer conjugate is a poly(oxazoline) polymer conjugate and the agent is tiagabine.

In the foregoing embodiments where the polymer conjugate is a poly(oxazoline) polymer conjugate, the poly(oxazoline) polymer conjugate may have the general formula as shown for compound II, IIA, IIB or IIC. In one embodiment, the polymer conjugate is a poly(oxazoline) polymer conjugate having the general formula as shown for compound IIC or an example herein.

In one embodiment, the polymer conjugate is a polyethylene glycol polymer conjugate and the agent is a compound useful in the treatment of an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy.

In one embodiment, the polymer conjugate is a polyethylene glycol polymer conjugate and the agent is a GABA re-uptake inhibitor.

In one embodiment, the polymer conjugate is a polyethylene glycol polymer conjugate and the agent is tiagabine or nipecotic acid.

In one embodiment, the polymer conjugate is a polyethylene glycol polymer conjugate and the agent is tiagabine.

In the foregoing embodiments, when the polymer is a polyethylene glycol polymer, the polyethylene glycol polymer may be a multi-arm polymer, including a 4-arm polymer, a difuncitonal polymer or a dendrimer.

In the foregoing embodiments where the polymer conjugate is a polyethylene glycol polymer conjugate, the polyethylene glycol polymer conjugate may have the general formula as shown for compound I or an example herein.

In one embodiment, the polymer conjugate is a dextran or oxidized dextran polymer conjugate and the agent is a compound useful in the treatment of an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy.

In one embodiment, the polymer conjugate is a dextran or oxidized dextran polymer conjugate and the agent is a GABA re-uptake inhibitor.

In one embodiment, the polymer conjugate is a dextran or oxidized dextran polymer conjugate and the agent is tiagabine or nipecotic acid.

In one embodiment, the polymer conjugate is a dextran or oxidized dextran polymer conjugate and the agent is tiagabine.

In the foregoing embodiments where the polymer conjugate is a dextran or oxidized dextran polymer conjugate, the dextran or oxidized dextran polymer conjugate may have the general formula as shown for compound I or an example herein.

In the methods described, the polymer conjugate may be administered alone or as a part of a pharmaceutical composition as described herein. In one embodiment, the subject is determined to be in need of such treatment. In a further embodiment, the polymer conjugate is administered in a therapeutically effective amount. In the methods disclosed herein, the subject may be a mammal. In certain embodiments, the subject is a human.

In one embodiment, the methods of treatment are accomplished by subcutaneous administration of the polymer conjugates of the present disclosure or pharmaceutical compositions containing such polymer conjugates.

In addition, in one embodiment, such polymer conjugate is administered once a day. In another embodiment, such polymer conjugate is administered once every other day. In still a further embodiment, such polymer conjugate is administered every third day, every fourth day, every fifth day or every sixth day. In yet a further embodiment, such polymer conjugate is administered once a week. Other dosing frequencies may also be used based on the nature of the polymer conjugate selected and the release kinetics of the agent.

The polymer conjugates described herein can also be administered in combination with other therapeutic agents, for example, other agents that are useful for treatment of PD or any other condition recited herein. When administered with other therapeutic agents, the polymer conjugates of the present disclosure may be administered before, after or at the same time as the additional therapeutic agent. Accordingly, in one embodiment the present disclosure also provides a composition comprising a polymer conjugate described herein, at least one other therapeutic agent, and a pharmaceutically acceptable diluent or carrier.

Kits

The present disclosure provides a kit comprising, consisting essentially of or consisting of a polymer conjugate of the present disclosure, packaging material, and instructions for administering the foregoing to a subject for the treatment of PD or another disease or condition related to dopamine insufficiency in the peripheral or central nervous system.

The present disclosure also provides a kit comprising, consisting essentially of or consisting of a polymer conjugate of the present disclosure, packaging material, and instructions for administering the foregoing to a subject for the treatment of an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy.

The present disclosure provides a kit comprising, consisting essentially of or consisting of a polymer conjugate of the present disclosure, at least one other therapeutic agent, packaging material, and instructions for administering the foregoing to a subject for the treatment of PD or another disease or condition related to dopamine insufficiency in the peripheral or central nervous system.

The present disclosure also provides a kit comprising, consisting essentially of or consisting of a polymer conjugate of the present disclosure, at least one other therapeutic agent, packaging material, and instructions for administering the foregoing to a subject for the treatment of an anxiety disorder, social anxiety disorder, panic disorder, neuropathic pain (which includes usefulness in poorly understood disorders like fibromyalgia), chronic pain, muscle tremors, muscle spasms, seizures, convulsions and/or epilepsy.

Methods of Manufacture

In one embodiment, the agent is linked to the polymer using "click chemistry". This approach is also readily applicable to all polymer types. In one embodiment, the polymer is POZ. In another embodiment, the polymer is PEG. In another embodiment, the polymer is dextran. The click chemistry approach involves the reaction between an alkyne group and an azido group. Therefore, in one embodiment, the agent contains one of an alkyne or azido group and the polymer contains the other of the alkyne or azido group. The respective groups may also be present on linking groups attached to the agent and/or polymer as well. In one aspect, the click chemistry reaction involves the reaction of an azidoester on the agent and an alkyne on the polymer. In a particular embodiment of this aspect, the azidoester group is formed by suitable chemical reactions with a chemical group on the agent, such as, but not limited to, a hydroxyl group. An exemplary reaction would be the preparation of an azidoester by displacing a halide from a halo acid with sodium azide to form the azidoacid followed by esterification of the azidoacid with a hydroxyl group on the agent (exemplified here as rotigotine).

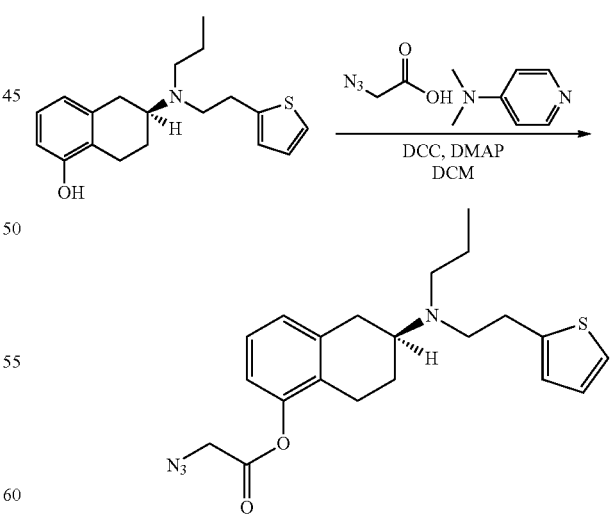

The azidorotigotine ester is then linked to an alkyne functionality present on the polymer. In a particular embodiment, the alkyne functionality is an acetylene functionality present at a pendent position on the POZ polymer.

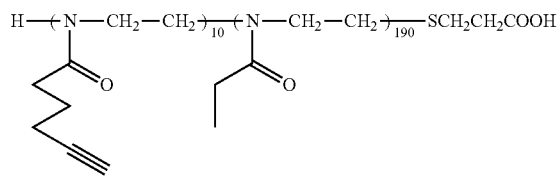
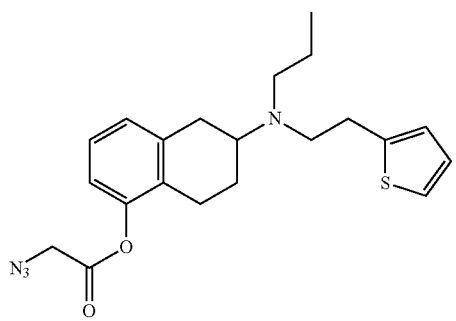
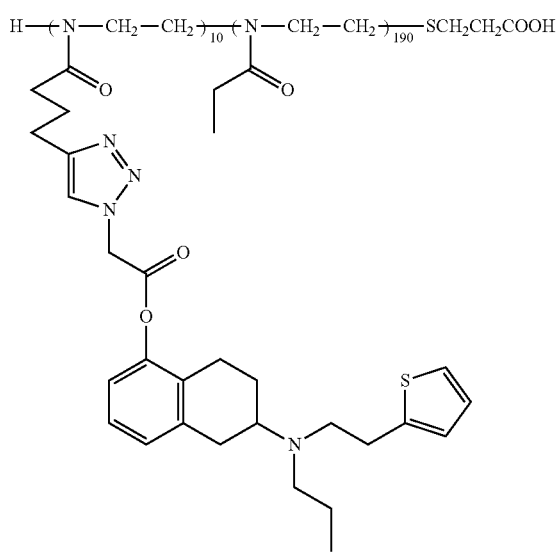

Azidoacetyl-Rotigotine

H—[(Acetyl-Rotigotine)$_{10}$(EOZ)$_{190}$]—COOH 20K

While the above method may be used, other approaches to the formation of releasable functionalities may be used. For example, a linkage containing an ester as the cleavable moiety may also be formed by creating an azide functional group on the polymer, such as a pendent group on a POZ polymer, creating an alkyne group on the agent, such as an acetylene ester of rotigotine, and reacting the azide group and the alkyne group to form a linkage having a cleavable moiety (in this case an ester bond).

In another approach, a carboxylic acid group can be created on the polymer, such as a pendent group on a POZ polymer, and reacting the carboxylic acid group by directly esterifying an alcohol or phenolic group on the agent to form a linkage having a cleavable moiety (in this case an ester bond). In one embodiment, a carboxylic acid group on the POZ polymer is generated at a pendent position on the POZ polymer by including a carboxylated monomer in the polymerization reaction.

In the preparation of the polymer conjugates of the present disclosure, the number of agents on the polymer is controlled by the number of reactive groups present on the polymer; in one embodiment, the reactive groups are present in a pendent position on the polymer. For reactive groups at the pendent position, the number of reactive groups present on the polymer is controlled by the ratio of monomer units (for example, monomer oxazolines) having functionalized side chains (e.g. acetylenes) capable of forming linkages with the agent or linking group relative to monomer units having inactive side-chains (e.g. alkyls) used in the polymerization. In addition, for a given ratio of monomer units having functionalized side chains, the polymer length can be controlled providing further control of the number of agents loaded onto a given polymer conjugate. Therefore, the number of agents attached to a particular polymer conjugate can be controlled. As described above, the nature of the linking group, the size of the polymer and the route of administration (intravenous, subcutaneous or transdermal) allows control over the release kinetics of the agent from the polymer. These combined properties allow one to "tune" the release of the attached agent by varying the amount of agent delivered and varying the release kinetics of the agent for the desired pharmacology.

Pharmaceutical Compositions

Polymer conjugates can be formulated for both human and veterinary use. These formulations contain pharmaceutically accepted ingredients that act as fillers, binders, carriers, stabilizers, buffers, solvents, co-solvents, viscosity enhancers, lubricants, surfactants, flavoring and sweetening agents, taste-masking agents, inorganic salts, antioxidants, antimicrobial agents, chelating agents, lipids, phospholipids, (Ref: Handbook of Pharmaceutical Excipients, 3rd edition, Ed. A. H. Kibbe, Pharmaceutical Press, 2000). The amount of agent in these formulations will depend on their physicochemical properties, dose and mode of administration. Most dosage forms will generally contain 1 to 99% by weight of the total formulation.

Formulations suitable for oral administration can be in solid form and they include tablets, pills, capsules, cachets, lozenges, fast dissolving solids, fine powders and granular powders. A tablet is a compression or mold of the drug conjugate and acceptable pharmaceutical excipients. Capsules are gelatin and non-gelatin cachets that encapsulate the drug and excipients. Formulations are also in liquid form and they include solutions, suspensions, emulsions, syrups and elixirs. These liquids may be aqueous, sugar based and non-aqueous based, glycol based.

Formulations suitable for parenteral use are sterile liquids and sterile powders and lyophilized powders ready for reconstitution in a suitable aqueous medium. Examples of the latter are sterile water for injection, 5% dextrose solution for injection, and 0.9% sodium chloride solution for injection, and lactated Ringer's injection. These formulations can be administered intravenously, subcutaneously, intramuscularly, and intradermally. These formulations are pH balanced and isotonic to blood and surrounding tissue. Similar formulations can be delivered as nasal sprays and eye drops.

Topical, transdermal and rectal formulations are water, polymer and oil based. They can be dissolved or suspended in mineral oil, petroleum waxes, liquid and solid polyols, polyhydroxy alcohols, cocoa butter, hydrogenated fats, surfactants, and esters of carboxylic acids. Transdermal formulations are reservoir or monolithic in design and the drug conjugates are typically in soluble form. Transdermal formulations also contain excipients to promote permeation of the agent across the skin.

EXPERIMENTAL EXAMPLES

Example 1—Synthesis of Random H-[(Ptyn)$_{10}$(EOZ)$_{190}$]-T-CO$_2$H

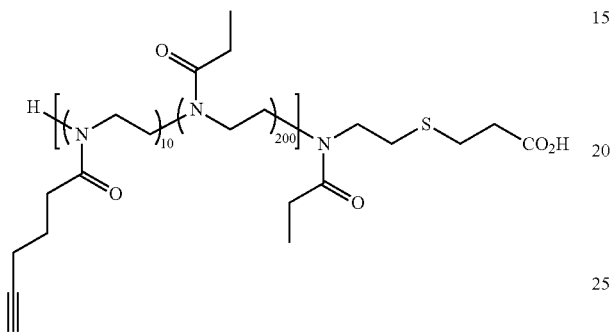

The synthesis of POZ polymers with various pendent groups is described in U.S. Pat. Nos. 8,110,651 and 8,101,706, each of which is incorporated herein by reference for such teachings. In a specific embodiment, the synthesis of H-[(Ptyn)$_{10}$(EOZ)$_{190}$]-T-CO$_2$H is provided although other POZ polymers with different molecular weights, different initiating and terminating groups as well as different groups at the "R$_2$" position (with reference to the definitions of POZ above) may be produced by the same methods. In addition, block copolymers may be produced in addition to the random copolymers described below. Methods for producing random and block copolymers are described in U.S. patent application Ser. Nos. 12/744,472 and 12/787,241, each of which is incorporated herein by reference for such teachings.

For the synthesis of H-[(Ptyn)$_{10}$(EOZ)$_{190}$]-T-CO$_2$H, triflic acid (HOTf, 173.3 μL, 1.96 mmol) was added to a solution of 2-pentynyl-2-oxazoline (PtynOZ, 3.76 g, 27.4 mmol, 14 eq) and 2-ethyl-2-oxazoline (EOZ, 46.61 g, 470.2 mmol, 240 eq) in chlorobenzene (124 mL). After stirring for 5 minutes at room temperature, the mixture was heated to 80° C. for 10 hours followed by cooling to room temperature. In a separate flask, the terminating reagent was prepared by the dropwise addition of methyl 3-mercaptopropionate (1.23 mL, 0.0114 mol) into a suspension of sodium hydride (60% in mineral oil, 0.272 g, 0.0068 mol) in chlorobenzene (34 mL). This mixture was stirred for 7 hours, before the solution of living polymer of H-(Ptyn)$_{10}$(EOZ)$_{200}$$^+$ was added. The resulting mixture was then stirred for 18 hours. The solvent was removed by rotary evaporation to yield a white residue. This residue was dissolved in water and the pH adjusted to 12.0. The resulting aqueous solution was purified by ion-exchange chromatography using DEAE Sepharose FF. The aqueous solution was saturated with NaCl (15% w/w) and extracted with dichloromethane. The combined organic phases were dried over anhydrous sodium sulfate, filtered, and concentrated using a rotary evaporator. The residue was precipitated by adding the dichloromethane concentrate to diethyl ether. The precipitated material was collected and dried in vacuo to give 22.8 g of desired product as a white powder (50% yield).

$^1$H NMR (Varian, 500 MHz, 10 mg/mL CDCl$_3$) showed the usual backbone peaks at 1.13 ppm (m, 3H, CH$_3$CH$_2$CO—); 2.32 ppm (m) and 2.41 (s) (total area 2H, CH$_3$CH$_2$CO—); and 3.47 ppm (m, 4H, —NCH$_2$CH$_2$N—). The terminal group peaks appear at 2.63 ppm (m, 2H, —SCH$_2$CH$_2$CO$_2$H), 2.74 ppm (m, 2H, —CH$_2$SCH$_2$CH$_2$CO$_2$H), and 2.85 ppm (m, 2H, —SCH$_2$CH$_2$CO$_2$H). The pendent pentynyl group peaks appear at 1.85 ppm (m, 2H, —CH$_2$CH$_2$CCH) and 2.03 ppm (br s, 1H, —CH$_2$CH$_2$C≡CH). The number of pendent, Ptyn, groups were determined as 8.5 by comparing the integrations of terminal acetylene proton and polymer backbone protons. GPC gave Mn=19,500 Da and Mp=20,800 Da with PDI of 1.07.

Example 2—Synthesis of Azidoacetic Acid in Non-aqueous Solvents

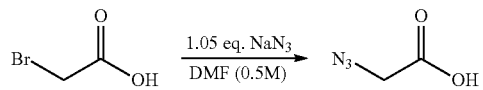 [SMILES: O=C(O)CBr ; [N-]=[N+]=NCC(=O)O]

This example provides a general synthetic scheme for the synthesis of various azidoalkyl acid linkers. To exemplify this method, the synthesis of 2-azidoacetic acid is provided. Through the substitution of 2-bromoacetic acid, used in the synthesis of 2-azidoacetic acid, with other reagents azidoalkyl acid linkers, such as, but not limited to, 3-azidopropionic acid and 2-azoidopropioni acid, may be produced.

For the synthesis of 2-azidoacetic acid, to a solution of 2-bromoacetic acid (1 g, 7.20 mmol) in DMF (14.39 ml) was added sodium azide (0.491 g, 7.56 mmol). After stirring for 16 hours at room temperature, the reaction mixture was monitored by RP HPLC showing 98% conversion (retention time, t$_r$=2.40 min) with remaining 2% bromoacetic acid (t$_r$=2.77 min).

H$^1$ NMR analysis (10 mg/mL in CDCl$_3$) showed the relevant peak at 3.84 ppm (s, 2H, N$_3$CH$_2$CO$_2$H).

Example 3—Synthesis of Rotigotine with 2-azidoacetic Acid Linker

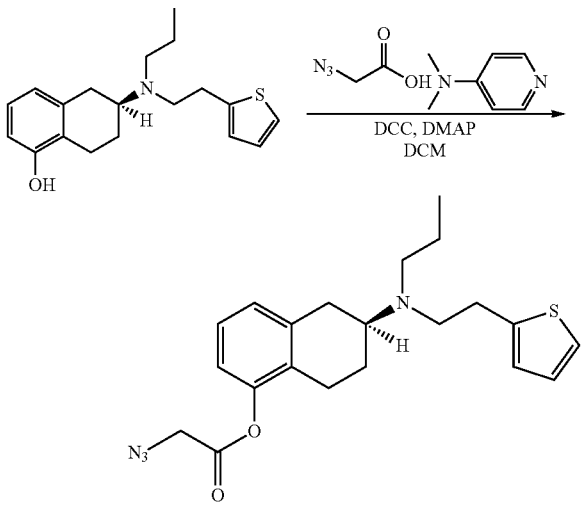

In a 25 mL round bottom flask, was placed rotigotine (1 g, 3.17 mmol, 1 equiv.), 2-azidoacetic acid-DMAP salt (0.849 g, 3.80 mmol, 1.2 equiv.) and 32 mL of anhydrous DCM and the mixture stirred under argon. DMAP (0.077 g, 0.634 mmol, 0.2 equiv.) and DCC (0.785 g, 3.80 mmol, 1.2 equiv.) were added as solids. The mixture was stirred for 16 hours at room temperature. The mixture was then filtered to remove precipitated urea and concentrated using a rotary evaporator. The crude mixture was first purified by silica gel column chromatography using a mixture of ethyl acetate and hexanes (1:2) as an eluent to give a clear yellow oil (1.27 g, 92% yield).

A second purification was performed by reversed phase chromatography to remove free rotigotine and other small molecule impurities. A sample solution for loading was prepared by dissolving crude azidoacetyl-rotigotine (350 mg) in 0.1% TFA in acetonitrile (4.05 mL), followed by addition of 1 N HCl (0.91 mL) and 0.1% TFA in water (4.04 mL). The sample solution was filtered through a 0.2 μm PTFE syringe filter, and then was loaded to a Waters SunFire Prep C18 OBD 30/250 Column (from Waters) on an AKTA Purifier system equipped with an UV detector at 214 nm. 0.1% TFA in water (A) and 0.1% TFA in acetonitrile (B) were used as mobile phase. The column was then eluted isocratically with 40% of mobile phase B at flow rate of 20 mL/min. The fractions that contained azidoacetyl-rotigotine were collected and pooled. Acetonitrile in the pooled fraction was evaporated by rotary-evaporation. The remaining aqueous solution was extracted with DCM (3×50 mL), dried over anhydrous sodium sulfate and filtered, followed by evaporation of the DCM. The residue was dried in vacuum (293 mg, 83%).

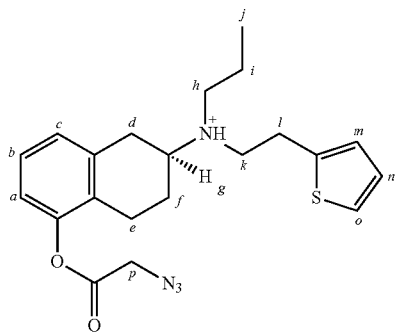

a, b, c, m, n, o: 6H,
δ6.932-7.223
p: 2H, δ4.156, s
j: 3H, δ1.030, t $^1$H NMR (Varian, 500 MHz, 10 mg/mL CDCl$_3$) showed peaks at 0.90 ppm (t, J=6.84 Hz, 3H), 1.25 (in, 1H), 1.29 (m, 1H), 1.49 (m, 1H), 1.59 (m, 1H), 2.05 (m, 2H), 2.54 (m, 3H), 2.82 (m, 3H), 2.97 (m, 3H), 4.156 N$_3$CH$_2$ C(=O)O— (s, 2H), 6.81 (s, 1H), 6.88 (d, J=7.81 Hz, 1H), 6.92 (t, J=3.42 Hz, 1H), 7.02 (d, J=7.32 Hz, 1H), 7.13 (m, 2H).

Figure 1B:
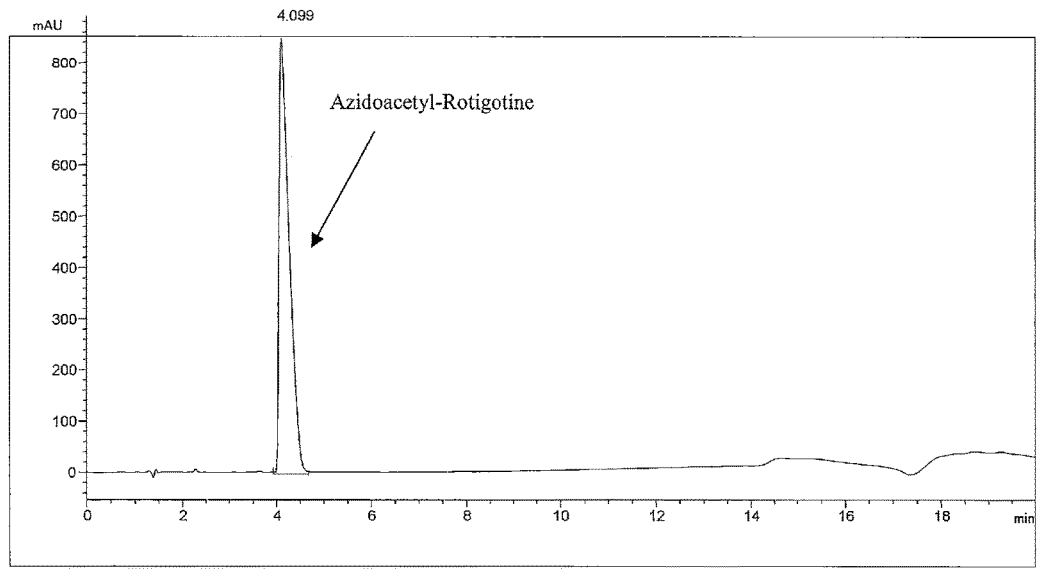
FIG. 1B shows an HPLC chromatogram of rotigotine 2-azidoacetate after reversed phase chromatography purification

RP-HPLC analysis showed that the product contained no free rotigotine. The HPLC chromatogram of azidoacetyl-rotigotine before (FIG. 1A) and after (FIG. 1B) reversed phase chromatography purification are shown.

Example 4—Synthesis of Rotigotine with 3-azidopropionic Acid Linker

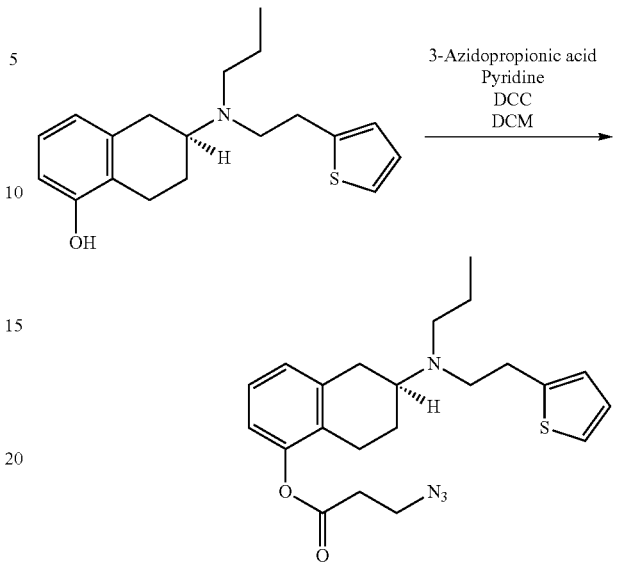

In a 50 mL round bottom flask, rotigotine (500 mg, 1.56 mmol, 1 equiv.), 3-azidopropionic acid (447 mg, 3.73 mmol, 2.4 equiv.) dissolved in 5 mL DCM, pyridine (302 μL, 3.73 mmol, 2.4 equiv.) were dissolved in 50 mL anhydrous DCM and allowed to stir under argon. The solution was cooled in an ice-water bath for 5 min, and the bath was removed. To the solution DCC was added (778 mg, 3.73 mmol, 2.4 equiv.). The solution was allowed to stir at room temperature under argon. Following an overnight reaction, reverse phase HPLC analysis of the reaction mixture showed complete conversion of free rotigotine to the ester form. The reaction mixture was filtered and the filtrate was concentrated to dryness on a rotary-evaporator. The crude product was then purified by silica gel chromatography. The crude product was dissolved in a mixed solvent of hexanes-ethyl acetate (6 mL, 4:1 v/v), was then loaded onto a 300 mL Silica Gel Column (30 mm id). The column was eluted with hexanes-ethyl acetate mixed solvent (4:1 v/v). The fractions (10 mL each) were analyzed by TLC and reversed phase HPLC. The product fractions were pooled, evaporated by rotary-evaporation, and then dried under vacuum overnight. Yield: 292 mg.

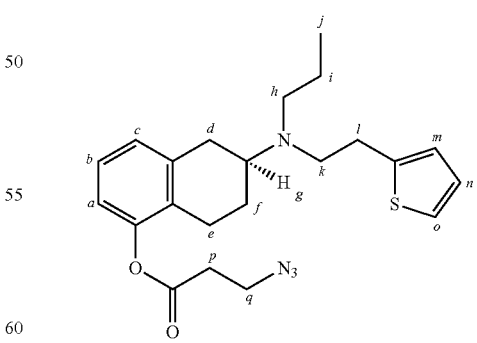

a, b, c, m, n, o: 6H,
δ6.808-7.127
p: 2H, δ2.838, t;
q: 2H, δ3.706, t;
j: 3H, δ0.895, t $^1$H NMR (Varian, 500 MHz, 10 mg/mL CDCl$_3$) showed peaks at 3.706 ppm N$_3$CH$_2$CH$_2$C(=O)O— (t, 2H), 2.838 N$_3$ CH$_2$CH$_2$C(=O)O— (t, 2H).

Example 5—Synthesis of Rotigotine with 2-azidopropionic Acid Linker

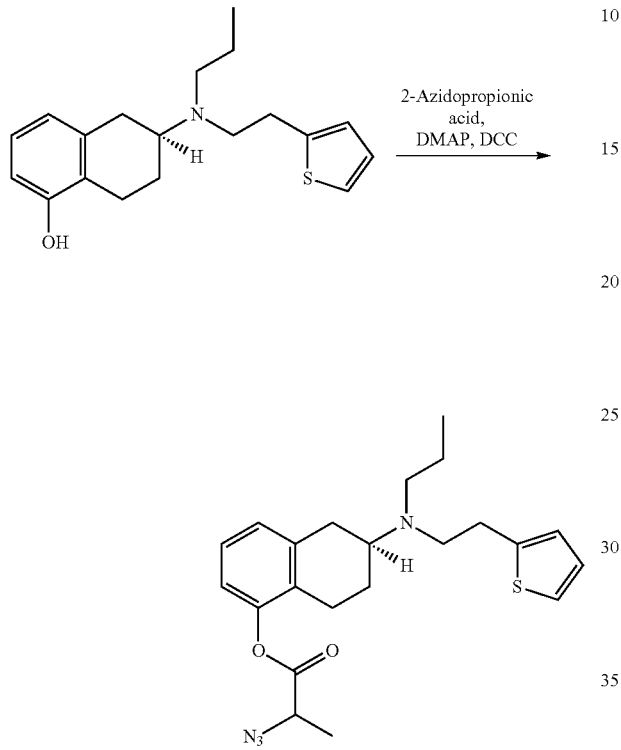

In a 100 mL round bottom flask was placed 2-azidopropionic acid (251 mg, 2.02 mmol, 1.3 equiv.) dissolved in 3 mL of DCM, rotigotine (500 mg, 1.55 mmol, 1 equiv.), and 4-DMAP (249 mg, 2.02 mmol, 1.3 equiv.) dissolved in 6 mL of DCM (6 mL) and the mixture was allowed to stir under argon. The solution was cooled by placing the flask in an ice-water bath for 5 min. To the solution, DCC was added (421 mg, 2.02 mmol, 1.3 equiv.). The progress of the reaction was followed by reversed phase HPLC. Following overnight stirring at room temperature, additional 2-azidopropionic acid (126 mg, 0.65 equiv.) in 2 mL of DCM and 4-DMAP (124 mg, 0.65 equiv.) were added to the reaction mixture, followed by DCC (211 mg, 0.65 equiv.). The solution was allowed to stir at room temperature for another 3.5 hours. HPLC result shows 94% of conversion to ester. The reaction mixture was filtered and the filtrate was concentrated to dryness on a rotary-evaporator. The crude product was then purified by silica gel chromatography. The crude product was dissolved in a mixed solvent of hexanes-ethyl acetate (6 mL, 4:1 v/v), and then loaded on to a 300 mL Silica Gel Column (30 mm id). The column was eluted with a hexanes-ethyl acetate mixed solvent (4:1 v/v). The fractions (10 mL each) were analyzed by TLC and reversed phase HPLC. The product fractions were pooled, evaporated by rotary-evaporation, and then dried in vacuum overnight. Yield: 307 mg.

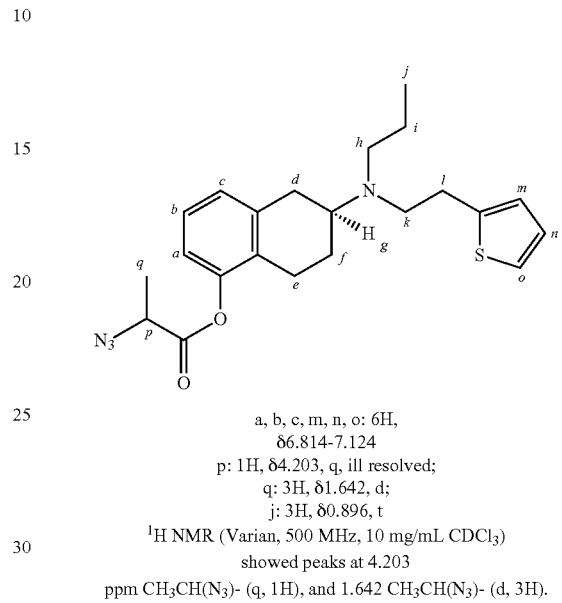

a, b, c, m, n, o: 6H, δ6.814-7.124
p: 1H, δ4.203, q, ill resolved;
q: 3H, δ1.642, d;
j: 3H, δ0.896, t $^1$H NMR (Varian, 500 MHz, 10 mg/mL CDCl$_3$) showed peaks at 4.203 ppm CH$_3$CH(N$_3$)- (q, 1H), and 1.642 CH$_3$CH(N$_3$)- (d, 3H).

Example 6—Preparation of H-[(Acetyl-Rotigotine)$_{10}$(EOZ)$_{190}$]—COOH 20K by Attachment of Azidoacetyl-Rotigotine to Polyoxazoline 10 Pendent Acid 20K

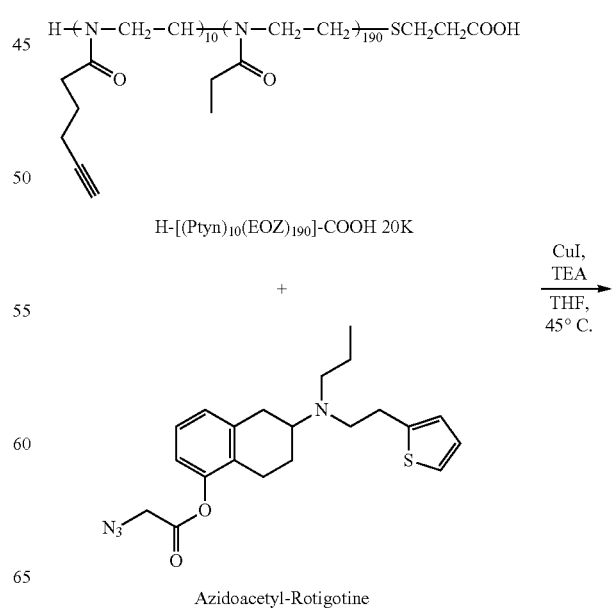

-continued

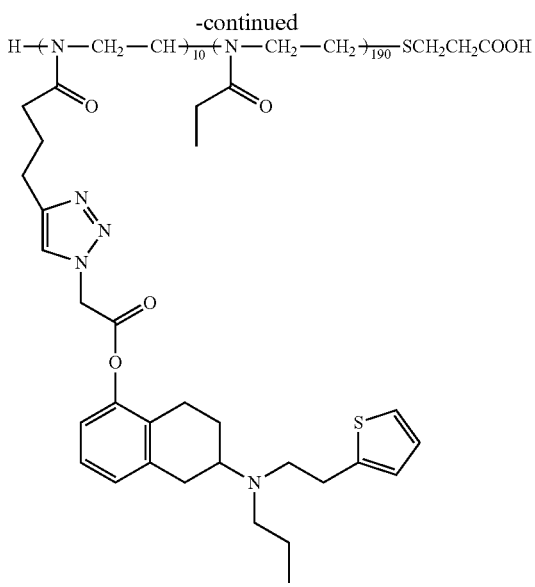

H-[(Acetyl-Rotigotine)$_{10}$(EOZ)$_{190}$]-COOH 20K

H-[(PtynOZ)$_{10}$(EOZ)$_{1901}$]—COOH 20K polymer (1.306 gm, 0.0653 mmol, 1.0 equiv.; prepare as described in Example 1) was dissolved in 15 mL of THF in a 100 mL round bottom flask. In a separate 50 mL round bottom flask, azidoacetyl-rotigotine (FW 384.50 Da. 251 mg, 0.653 mmol, 10.0 equiv.; prepared as in Example 3) was dissolved in 15 mL of THF (15 mL). The azidoacetyl-rotigotine solution was transferred into the 100 mL round bottom flask. The solution was flushed with argon. CuI (Copper (I) iodide, ≥99.5%, Sigma-Aldrich, 50 mg, 0.261 mmol, 4.0 equiv.) was then added to the flask, followed by addition of TEA (127 µL, 0.914 mmol, 14.0 equiv.). The solution was allowed to stir overnight at 45° C. under Argon. The green, crude reaction mixture was filtered with the aid of a 0.2 µm syringe filter, and then 0.1 N HCl acid (20 mL) was added into the filtrate. The mixture turned brown in color. The THF in the mixture was evaporated with the aid of a rotary-evaporator at 28° C.

Two column purification steps were employed to purify the crude product. In step one, a glass column (2 cm ID) was packed with a slurry of silica gel 60 (EMD, 70-230 Mesh, 30 mL) in 60 mL of 0.1 N HCl acid. The column packing and elution was done by gravity. Prewashed (water and 2 mM HCl acid) Dowex® M4195 media (20 mL) was packed above the silica layer. The column was equilibrated with 2 mM HCl (50 mL).

In a second glass column, Amberlite IR-120H (40 mL) was packed and washed with deionized water until the conductivity of the eluent was less than 1 µS/cm. The column was then equilibrated with 2 mM HCl (40 mL).

The filtered crude reaction mixture (20 mL) which contained >300 mg/L Cu$^{+/2+}$ (measured by Quantofi Copper test stick), was loaded on to the first Dowex/silica gel column. The column was eluted with 2 mM HCl acid. The eluent that containing the H-[(Acetyl-Rotigotine)$_{10}$(EOZ)$_{190}$]—COOH 20K polymer product (100 mL) was collected. The Cu$^{+/2+}$ levels was less than 10 mg/L (Quantofi Copper test stick). Free rotigotine in the eluent was then removed by the Amberlite IR-120H as next described. The eluent of the Dowex/silica gel column (100 mL) was loaded onto Amberlite IR-120H (40 mL) column. The column was eluted with 1 mM HCl. To the eluent (150 mL) from the Amberlite column, NaCl was added to make 10% concentration. The cloudy solution was extracted with DCM (3×200 mL, gentle shaking) and dried over anhydrous sodium sulfate. The salt was filtered off, and the filtrate was concentrated to ~20 mL by rotary-evaporation. The concentrated solution was added to 400 mL of ethyl ether to obtain a precipitate. Following filtration, the precipitate was dried under vacuum. The yield was 1.13 gm. RP-HPLC analysis showed the absence of rotigotine and azidoacetyl-rotigotine. The produced polyoxazoline conjugate of rotigotine showed good water solubility.

$^1$H NMR (Varian, 500 MHz, 10 mg/mL CDCl$_3$) showed peaks at 5.479 ppm —NCH$_2$ C(=O)O— (s, 2H), 6.945-7.197 from the phenyl and thiophene groups of rotigotine.

Example 7—Preparation of H-[(Propionyl-Rotigotine)$_{10}$(EOZ)$_{190}$]—COOH 20K by Attachment of 3-Azidopropionyl-Rotigotine to Polyoxazoline 10 Pendent Acid 20K H-[(PtynOZ)$_{10}$(EOZ)$_{190}$]—COOH 20K (681 mg, 0.034 m mol, 1 equiv.; prepared as in Example 1) was dissolved in 15 mL of THF in a 50 mL round bottom flask. In a 20 mL glass vial, 3-azidopropionyl-rotigotine (140 mg, 0.340 mmol, 10.0 equiv.; prepared as in Example 4) was dissolved in 5 mL of THF. The 3-azidopropionyl-rotigotine solution was transferred into the 50 mL round bottom flask. The solution was flushed under Argon. CuI (Copper (I) iodide, ≥99.5%, Sigma-Aldrich, 26 mg, 0.136 mmol, 4.2 equiv.) was then added to the flask, followed by addition of TEA (20 µL, 0.144 mmol). The solution was allowed to stir overnight at 45° C. under an Argon atmosphere. The green crude reaction mixture was cooled to room temperature and 0.1 N HCl acid (10 mL) was added to it. The reaction mixture became a clear yellow-brownish color. The THF in the mixture was evaporated with the aid of a rotary-evaporator at 28° C.

The reaction mixture was purified, extracted and precipitated as explained in Example 6. The yield was 611 mg. RP-HPLC analysis showed the absence of rotigotine and 3-azidopropionyl-rotigotine. The produced polyoxazoline conjugate of rotigotine showed good water solubility.

$^1$H NMR (Varian, 500 MHz, 10 mg/mL CDCl$_3$) showed peaks at 4.829 ppm —NCH$_2$ CH$_2$C(=O)O— (t, 2H), 6.876-7.194 from the phenyl and thiophene groups of rotigotine.

Example 8—Preparation of H-[(-[(α-Methyl-Acetyl-Rotigotine)$_{10}$(EOZ)$_{190}$]—COOH 20K by Attachment of 2-Azidopropionyl-Rotigotine to Polyoxazoline 10 Pendent Acid 20K H-[(PtynOZ)$_{10}$(EOZ)$_{190}$]COOH 20K (1.409 gm, 0.070 mmol, 1 equiv.; prepared as in Example 1) was dissolved in 15 mL of in a 100 mL round bottom flask. In a 20 mL glass vial, 2-azidopropionyl-rotigotine (291 mg, 0.705 mmol, 10.0 equiv.; prepared as in Example 5) was dissolved in 15 mL of THF (15 mL). The 2-azidopropionyl-rotigotine solution was transferred into the 100 mL round bottom flask. The solution was flushed under argon. CuI (Copper (I) iodide, ≥99.5%, Sigma-Aldrich, 54 mg, 0.282 mmol, 4.0 equiv) was then added to the flask, followed by addition of TEA (41 µL, 0.296 mmol, 4.2 equiv.). The solution was stirred overnight at 45° C. under an argon atmosphere. The reaction mixture was cooled to room temperature, filtered through a 0.2 µm PTFE syringe filter. 0.1 N HCl (20 mL) and added into the filtrate. The crude mixture turned clear brown in appearance. The THF in the mixture was evaporated with the aid of a rotary-evaporator at 28° C.

The reaction mixture was purified, extracted and precipitated as described in Example 6. The yield was 541 mg. RP-HPLC analysis showed the absence of rotigotine and 2-azidopropionyl-rotigotine. The produced polyoxazoline conjugate of rotigotine showed good water solubility.

$^1$H NMR (Varian, 500 MHz, 10 mg/mL CDCl$_3$) showed peaks at 5.692 ppm —N(CH$_2$)CHC(═O)O— (s, H), 6.943-7.196 from the phenyl and thiophene groups of rotigotine.

Example 9—Preparation of 4-Arm Polyethylene Glycol-acetylene (10K)

4-Arm Polyethylene Glycol-SCM (4-Arm PEG-SCM, 220 mg, 0.02 mmole, 1 eq., MW: 11,000 Da) was dissolved in 0.55 mL of dichloromethane in a 3 mL vial under Argon. Propargylamine (8.8 mg, 0.16 mmole, 8 eq.) and triethylamine (16.2 mg, 0.16 mmole, 8 eq.) were then added into the vial. The vial was closed with a rubber septum and the solution was stirred at room temperature under Argon for 18 h. The DCM solution was then precipitated into diethylether (10 mL) in a 20 mL vial. 3 mL vial was rinsed with 0.25 mL of DCM and this portion was also precipitated into the diethylether. The solution was filtered using a 150 mm Whatman filter paper. The polymer was dissolved in 2 mL of isopropanol at 50° C. and the solution was cooled down to room temperature. The precipitate was filtered using a 30 mL glass sintered frit and dried under high vacuum overnight (18 h) to give 203 mg of the final polymer (yield: 95%). $^1$H NMR of the final polymer shows that 4-Arm PEG-SCM chemical shifts at 2.82 ppm (s, 4H, NCOCH$_2$CH$_2$CO) and 4.48 ppm (s, 2H, OCH$_2$COO) completely disappeared and new peaks at 2.24, 4.02, and 4.09 ppm appeared for the new polymer. $^1$H NMR (CDCl$_3$, 500 MHz) δ: 2.24 (s, 1H, C≡CH), 3.59 (m, CH$_2$ (PEG)), 4.02 (s, 2H, OCH$_2$CONH), 4.09 (dd, 2H, CH$_2$C≡CH).

Example 10—Preparation of 4-Arm PEG-acetyl-Rotigotine

Azidoacetyl rotigotine from example 3 (15.9 mg, 0.016 mmole, 1.6 eq.) was dissolved in 3 mL of THF in a vial. 4-Arm PEG-acetylene (110 mg, 0.01 mmole, 1 eq., MW: 11,000 Da) was added and mixture was stirred to dissolve the polymer completely. Copper (I) iodide (3.1 mg, 0.016 mmole, 1.6 eq.) and triethylamine (1.6 mg, 2.21 μL, 0.016 mmole, 1.6 eq.) were added to give a clear green color solution. The resulting solution was stirred at 45° C. under Argon blanket for 17 h. The cloudy mixture (yellow-brownish) was cooled down to room temperature and filtered using a 0.2 μm PTFE syringe filter. The filtrate was stirred with 2 mL of 0.1 N HCl resulting in a slightly cloudy yellow mixture (pH: 2.5). THF was removed using a rotary evaporator at 28° C. The resulting aqueous solution (cloudy) was passed through a Dowex column (10 g, 15 mL). 60 mL of aqueous solution was collected. The solution was then passed through a column packed with 10 g of Amberlite IR-120H (15 mL) resulting in 150 mL of aqueous solution. The solution was saturated with NaCl (15 g) and extracted with DCM three times (3×50 mL). Organic layers were separated, combined, dried over Na$_2$SO$_4$ (10 g), filtered and concentrated down to 0.5 mL and then precipitated into diethylether (20 mL) in a 50 mL beaker. The precipitate was filtered on a 15 mL glass frit and dried under high vacuum overnight to give 95 mg of the final product (yield: 78%)

$^1$H NMR (CDCl$_{13}$, 500 MHz) δ: 0.97 (3H, —NCH$_2$CH$_2$CH$_3$); 1.86 (total of 3H, —NCH$_2$CH$_2$CH$_3$ and —NCHCH$_2$CH$_2$C—); 2.51 (1H, —NCHCH$_2$CH$_2$C—); 2.79-3.49 (total of 11H, rest of the aliphatic CH$_2$ and CH peaks); 3.58 (m, CH$_2$ (PEG)), 3.97 (s, 2H, OCH$_2$CONH), 4.56 (t, 2H, triazole-CH$_2$NHCO), 5.39 (s, triazole-CH$_2$COO); 6.70-7.03 (3H, CH peaks of 1,2,3,4-tetrahydronaphtalene); 6.93-7.42 (3H, CH peaks of 2-thiophene); 7.68-7.83 (d, CH peak of triazole).

Example 11—Coupling of 4-Arm PEG-acetylene (10K) to Azidopropyl Rotigotine

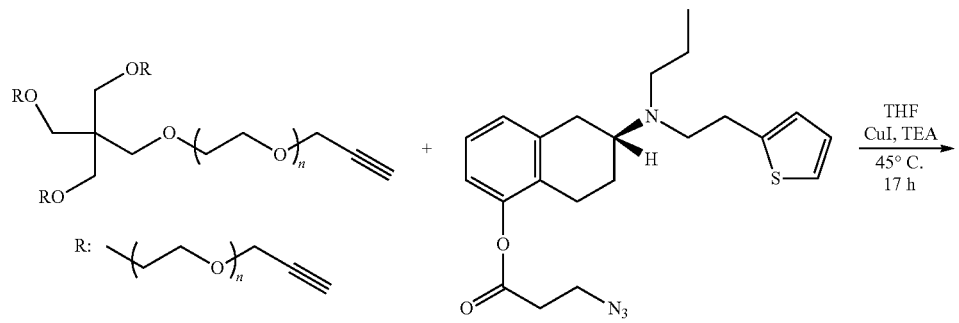

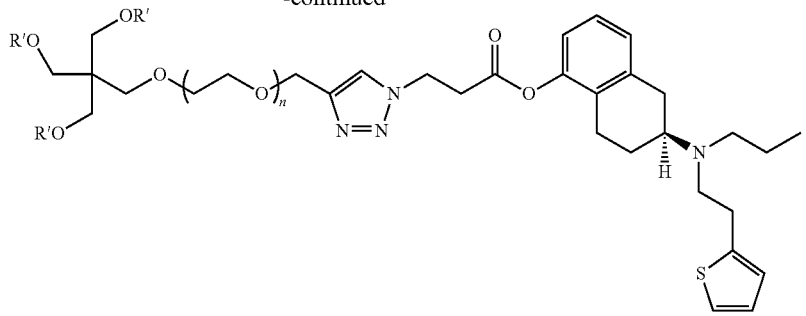

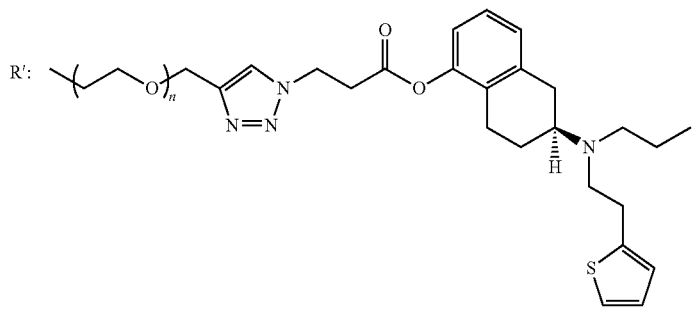

95.0 mg of azidopropyl rotigotine.TFA (0.18 mmole) was dissolved in 20 mL of THF in a 50 mL one-neck round-bottom flask and 330 mg of 4-Arm PEG-acetylene (Creative PEGWorks, ZQ9214,) (0.03 mmole, MW: 11,000 g/mole) was added into the flask and mixture was stirred to dissolve the polymer (brown mixture). 9.3 mg of copper (I) iodide (0.048 mmole) and 6.63 µL of triethylamine (4.8 mg, 0.048 mmole) were added to give a clear brown color solution. The resulting solution was stirred at 45° C. under Argon blanket for 17 h. The brown mixture was cooled down to room temperature and filtered through a 0.2 µM PTFE filter. The filtrate was stirred with 6 mL of 0.1 N HCl resulting in a brown mixture (pH 2.5 by pH paper). THF was removed using a rotary evaporator at 28° C. The resulting cloudy aqueous solution was passed through a column packed with Dowex (10 mL, M4195, Supelco, 1844261) at the top and 20 g of Amberlite IR-120 (30 mL, Fluka, BCBF3074V) at the bottom resulting in 200 mL of aqueous solution. The solution was saturated with 20 g of NaCl and extracted with 50 mL of DCM three times (3×50 mL). The organic layers were separated, combined, dried over 20 g of $Na_2SO_4$, filtered, concentrated down to 2 mL and precipitated into 40 mL of diethylether in a 50 mL beaker. The polymer was filtered and dried under high vacuum to give 310 mg of the final product in 81% yield.

$^1$H NMR ($CDCl_3$, δ, ppm, TMS): 1.03 (3H, —$NCH_2CH_2CH_3$); 1.8-3.6 (total of 17H, aliphatic CH and $CH_2$ peaks of rotigotine; 2.56 (2H, —$OCOCH_2CH_2$-triazole); 3.41 (—$C(CH_2O)_4$); 3.64 (1000H, —$OCH_2CH_2O$—); 4.71 (2H, —$OCH_2$-triazole); 4.76 (2H, —$OCOCH_2CH_2$-triazole); 6.88-7.21 (6H, —CH peaks of 1,2,3,4-tetrahydronaphtalene and —CH peaks of 2-thiophene); 7.76 (1H, —CH peak of triazole).

Example 12: Coupling of 4-Arm PEG-acetylene (20K) to Azidopropyl Rotigotine

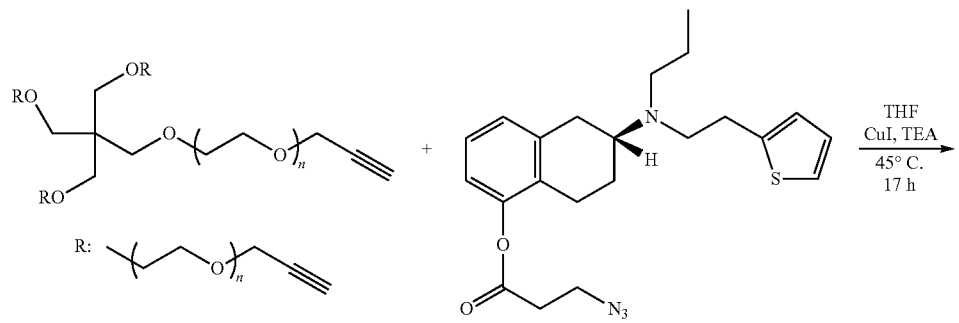

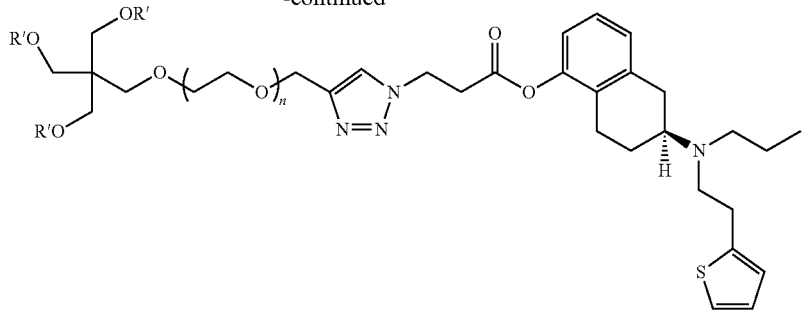

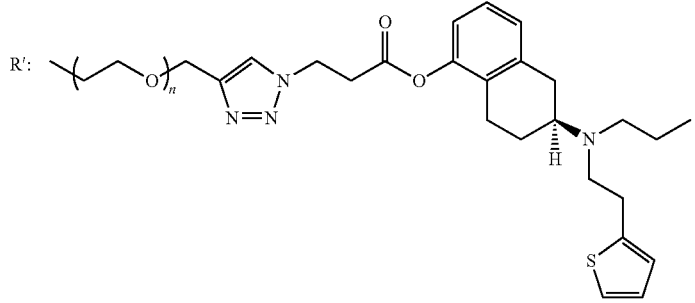

126.2 mg of azidopropyl rotigotine. TFA (ZH-27-9P) (0.24 mmole) was dissolved in 40 ml of THF in a 50 one-neck round-bottom flask and 624 mg of 4-Arm PEG-acetylene (Creative PEGWorks, ZQ9216) (0.03 mmole, MW: 20,800 g/mole) was added into the flask and mixture was stirred to dissolve the polymer completely (yellow solution). 9.63 mg of copper (I) iodide (0.048 mmole) and 6.60 μL of triethylamine (4.8 mg, 0.048 mmole) were added to give a clear yellow color solution. The resulting solution was stirred at 45° C. under Argon blanket for 40 h. The reaction was topped after 40 h of stirring. The solution was filtered through a 045 μM PTFE filter. The filtrate was stirred with 12 mL of 0.1 N HCl resulting in a brown mixture (pH 2.5 by pH paper). THF was removed using a rotary evaporator at 28° C. The resulting cloudy aqueous solution was passed through a column packed with Dowex (20 mL, M4195, Supelco, 1844261) at the top and 40 g of Amberlite 1R-120 (60 mL, Fluka, BCSF3074V) at the bottom resulting in 400 mL of aqueous solution. The solution was saturated with 40 g of NaCl and extracted with 50 mL of DCM three times (3×50 mL). The organic layers were separated, combined, dried over 20 g of $Na_2SO_4$, filtered and concentrated down to 4 mL. The DCM solution was then precipitated into 80 mL of diethylether in a 100 mL beaker. The solvent was decanted and the polymer was dried under high vacuum to give 582 mg of the final product in 86% yield.

$^1$H NMR (CDCl$_3$, δ, ppm, TMS): 1.03 (3H, —NCH$_2$CH$_2$CH$_3$); 1.8-3.6 (total of 17H, aliphatic CH and CH$_2$ peaks of rotigotine; 2.56 (2H, —OCOCH$_2$CH$_2$-triazole); 3.41 (2H, —C(CH$_2$O)$_4$); 3.64 (1000H, —OCH$_2$CH$_2$O—); 4.69 (2H, —OCH$_2$-triazole); 4.74 (2H, —OCOCH$_2$CH$_2$-triazole); 6.88-7.21 (6H, —CH peaks of 1,2,3,4-tetrahydronaphtalene and —CH peaks of 2-thiophene); 7.71 (1H, —CH peak of triazole).

Example 13—Preparation of 2-Arm PEG Acetylene (10K)

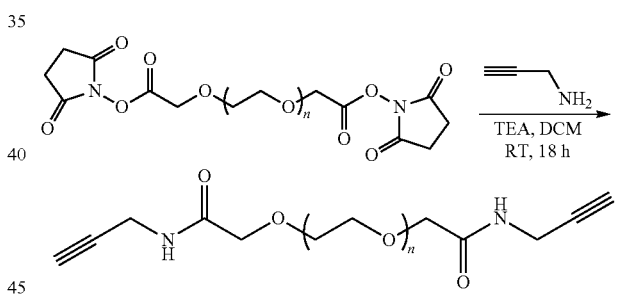

1.05 g of SCM-PEG-SCM (0.1 mmole, MW: 10,500 g/mole) was dissolved in 2.5 mL of dichloromethane (DCM) in a 10 mL vial under Argon and 25.6 μl, of propargylamine (22 mg, 0.4 mmole) and 56.5 μL of triethylamine (41 mg, 0.4 mmole) were then added into the vial. The vial was closed with a rubber septum and the solution was stirred at room temperature under Argon for 18 h. The DCM solution was then precipitated into 50 mL of diethylether in a 100 mL beaker. 10 mL vial was rinsed with 1 mL of DCM and this portion was also precipitated. The solution was filtered using a 150 mm Whatman filter paper. The filtered polymer was redissolved in 50 mL of isopropanol at 50° C. and cooled down to room temperature. The polymer was recrystallized upon cooling. The polymer was filtered using 30 mL glass sintered frit and dried under high vacuum overnight to give 1.0 g of the final polymer in 96% yield (BD-23-86-1). $^1$H NMR (CDCl$_3$, δ, ppm, TMS): 2.24 (1H, —CONHCH$_2$C≡CH), 3.64 (920H, —OCH$_2$CH$_2$O—), 4.02 (2H, —OCH$_2$CONHCH$_2$C≡CH), 4.10-4.15 (2H, —CONHCH$_2$C≡CH).

Example 14: Coupling of 2-Arm PEG-acetylene (10K) to Rotigotine 3-azidopropionate

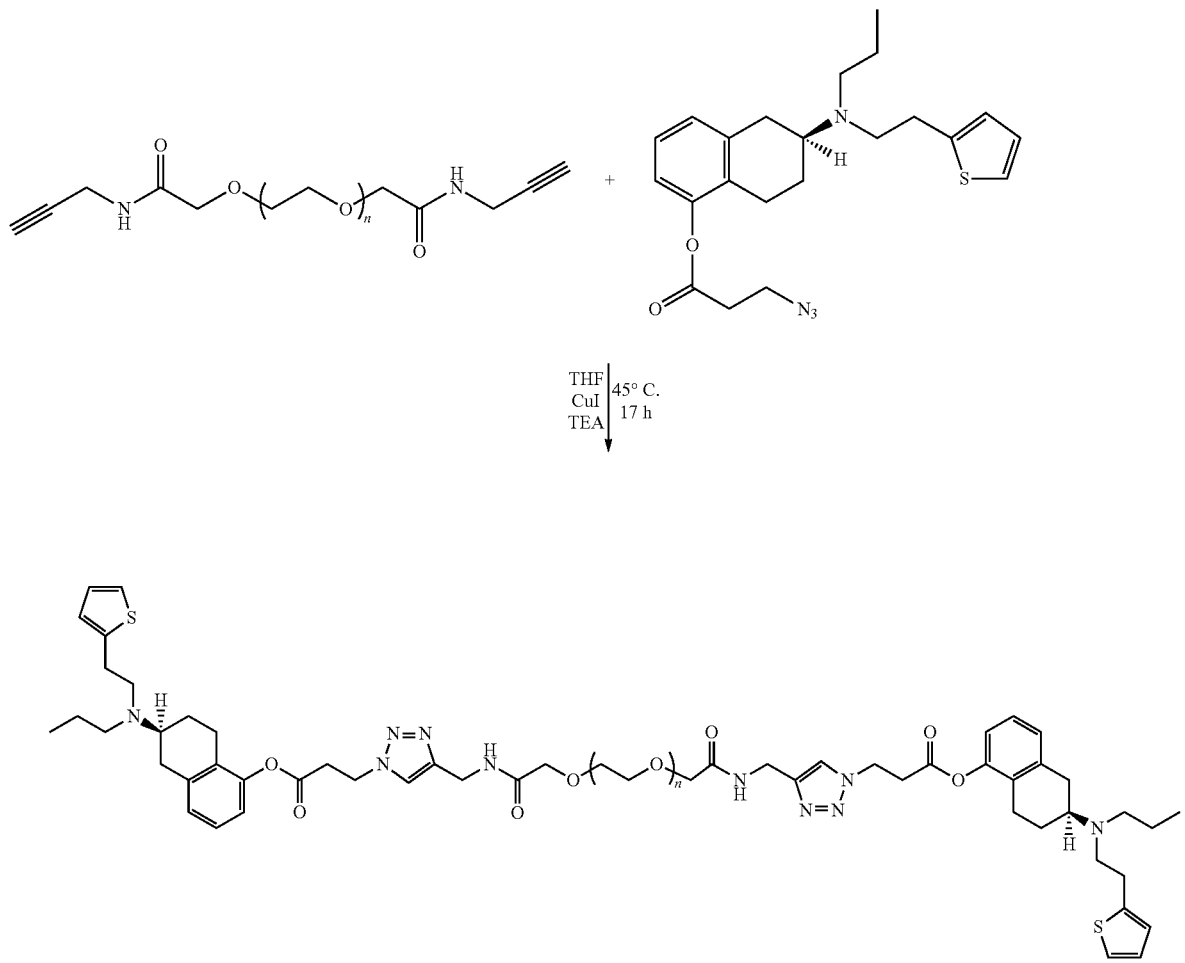

47.3 mg of azidopropyl rotigotine. TFA (0.09 mmole) was dissolved in 20 ml of THF in a 50 mL one-neck round-bottom flask and 315 mg of acetylene-PEG-acetylene (0.03 mmole) was added into the flask and mixture was stirred to dissolve the polymer completely (clear colorless solution). 9.3 mg of copper (I) iodide (0.048 mmole) and 6.63 μL of triethylamine (4.8 mg, 0.048 mmole) were then added into the flask to give a clear green color solution. The resulting solution was stirred at 45° C. under Argon blanket for 20 h. The green color mixture was cooled down to room temperature and filtered using a 0.2 μm PTFE syringe filter. The filtrate was stirred with 6 mL of 0.1 N HCl resulting in a yellow mixture (pH 2.5 by pH paper). THF was removed using a rotary evaporator at 28° C. The resulting cloudy aqueous solution was passed through a column packed with 10 mL of Dowex (M4195, Supelco, 1844261) at the top and 20 g of Amberlite IR-120 (30 mL, Fluka, BCBF3074V) at the bottom resulting in 200 mL of aqueous solution. The aqueous solution was saturated with 20 g of NaCl and extracted with 50 mL of DCM three times (3×50 mL). The organic layers were separated, combined, dried over 20 g of Na$_2$SO$_4$, filtered, concentrated down to 2 mL and precipitated into 40 mL of diethylether in a 50 mL beaker. The precipitated polymer was filtered and dried under high vacuum to give 250 mg of the final product in 73% yield.

$^1$H NMR (CDCl$_3$, δ, ppm, TMS): 1.03 (3H, —NCH$_2$CH$_2$CH$_3$); 1.8-3.6 (total of 17H, aliphatic CH and CH$_2$ peaks of rotigotine; 2.63 (2H, —OCOCH$_2$CH$_2$CH$_2$-triazole); 3.64 (920H, —OCH$_2$CH$_2$O—); 4.02 (2H, —OCH$_2$CONHCH$_2$C≡CH); 4.61 (2H, —CONHCH$_2$-triazole); 4.76 (2H, —OCOCH$_2$CH$_2$-triazole); 6.87-7.21 (6H, —CH peaks of 1,2,3,4-tetrahydronaphtalene and —CH peaks of 2-thiophene); 7.75 (—CH peak of triazole); 7.81 (1H, —CONH—).

Example 15—Preparation of 4-Arm PEG Rotigotine Glycine Ester (10K)

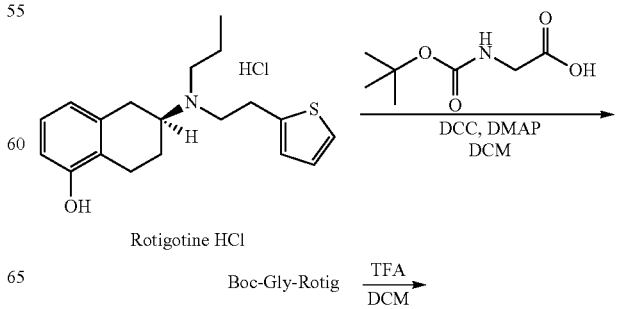

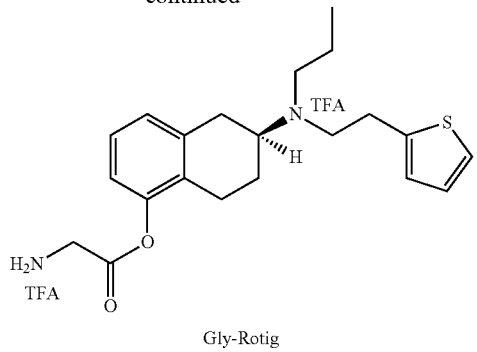

Gly-Rotig

Glycine-Rotigotine Synthesis:

Rotigotine HCl (1.2 g, 3.41 mmol) and Boc-Glycine OH (1.195 g, 6.82 mmol) were dissolved in dichloromethane (150 ml) to give a suspended solution. After the addition of DMAP (0.625 g, 5.11 mmol) and DCC (1.407 g, 6.82 mmol), the mixture was stirred for 16 hours at room temperature. The mixture was filtered using a filter paper and the filtrate was quenched with 51 mL of 0.1 N HCl (5.11 mmol). Two layers were separated and the aqueous phase was extracted with 7 mL of dichloromethane. The combined organic phases were washed with water and then with brine, dried over $Na_2SO_4$, filtered, concentrated using a rotary evaporator, and dried in vacuo to give a crude as pale yellow solids. The crude material was stirred with diethyl ether (50 mL) for 30 minutes, filtered on a glass frit, rinsed with diethyl ether, and dried in vacuo to give a pale yellow powder as a desired product Boc-Gly-Rotigotine. HCl (1.258 g, 75% yield).

$^1$H NMR (Varian, 500 MHz, 10 mg/mL $CDCl_3$) showed peaks at 1.04 ppm (t, 3H, —$CH_2CH_2CH_3$), 1.47 ppm (s, 9H, —NHBoc), 1.96 ppm (m, 2H), 2.06 ppm (m, 1H), 2.60 ppm (m, 2H), 2.93 ppm (m, 1H), 3.04 ppm (m, 1H), 3.13 ppm (m, 1H), 3.26 ppm (m, 2H), 3.40 ppm (m, 2H), 3.52 ppm (m, 1H), 3.66 ppm (m, 2H), 4.17 ppm (d, 2H, —$NHCH_2C$(=O)—), 5.08 ppm (s, 1H, —C(=O)$NHCH_2$—), 6.95 ppm (m, 3H, aromatic), 7.06 ppm (t, 1H, thiophenyl), and 7.20 ppm (m, 2H, thiophenyl).

The Boc-Gly-Rotig HCl was deprotected by first dissolving 1.258 g (2.55 mmol) in dichloromethane (64 ml). After addition of trifluoroacetic acid (9.83 ml, 128 mmol), the reaction mixture was stirred for 1 hour at room temperature and then all the volatiles were removed using a rotary evaporator. The residue (dark yellow) was redissolved in methanol and precipitated by adding into diethyl ether (40 mL). The pale yellow precipitates were filtered using a glass fit and dried to give Gly-Rotigotine. 2TFA (1.140 g, 79% yield).

$^1$H NMR (Varian, 500 MHz, 10 mg/mL $CDCl_3$) showed peaks at 0.98 ppm (d, 3H, —$CH_2CH_2CH_3$), 1.72 ppm (m, 1H), 1.83 ppm (m, 2H), 2.33 ppm (m, 1H), 2.51 ppm (m, 2H), 2.80 ppm (m, 1H), 3.00 ppm (m, 2 1-1), 3.12 ppm (m, 2H), 130 ppm (m, 3H), 3.73 ppm (m, 1H), 4.03 ppm (q, 2H, $NH_2CH_2C$(=O)O—), 6.80 ppm (d, 1H, aromatic), 6.92 ppm (m, 2H, aromatic), 6.99 ppm (d, 1H, thiophenyl), 7.08 ppm (t, 1H, thiophenyl), and 7.17 ppm (d, 1H, thiophenyl).

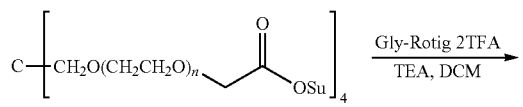

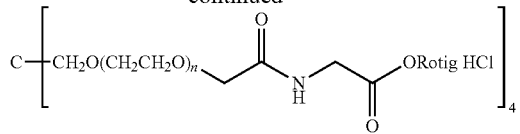

4-arm PEG-SCM 10K (2.02 g, 0.165 mmol) and Gly-Rotigotine. 2TFA (0.373 g, 0.658 mmol) were dissolved in dichloromethane (16.5 ml). TEA (0.229 ml, 1.645 mmol) was added to give a yellow clear solution. After stirring for 16 hours at room temperature, the mixture was quenched with 16 mL of 0.1N HCl solution and charged with 1.6 g of NaCl (10 w/v % for water). Two layers were separated and the aqueous phase was extracted with 16 mL of dichloromethane. The combined organic phases were dried over $Na_2SO_4$, filtered, and concentrated. The crude extract was dissolved in 40 mL of water and passed through Amberlite (IR120H) column to remove all the small molecules. The collected aqueous solution was stirred with 50 mL of dichloromethane and charged with 10.5 g of NaCl (15 w/v % of water). Two layers were separated and the aqueous phase was extracted with additional 50 mL of dichloromethane. The combined organic phases were dried over $Na_2SO_4$, filtered, concentrated, and dried in vacuo to give the desired product 4-arm PEG-Gly-Rotigotine. HCl 10K (1.89 g, 85% yield).

$^1$H NMR (Varian, 500 MHz, 10 mg/mL $CDCl_3$) showed the polymer backbone peaks at 3.64 ppm (m, 4H, —($OCH_2CH_2$)$_n$—) and other major peaks at 1.04 ppm (d, 3H, —$CH_2CH_2CH_3$), 6.96 ppm (m, 3H, aromatic), 7.05 ppm (t, 1H, thiophenyl), 7.20 ppm (m, 2H, thiophenyl), and 7.80 ppm (m, 1H, triazole). The average number of rotigotine molecules on each polymer was determined as 3.1 by $^1$H NMR analysis.

Example 16—Preparation of 4-Arm PEG Rotigotine Glycine Ester (20K)

The glycine-rotigotine. 2TFA salt was prepared as described in example 16. The 4-arm PEG-SCM 20K (2.007 g, 0.098 mmol) and Gly-Rotigotine. 2TFA (0.222 g, 0.393 mmol) were dissolved in dichloromethane (9.8 ml). TEA (0.137 ml, 0.981 mmol) was added to give a yellow clear solution. After stirring for 16 hours at room temperature, the mixture was quenched with 9.8 mL of 0.1N HCl solution and charged with 1.0 g of NaCl (10 w/v % for water). Two layers were separated and the aqueous phase was extracted with 10 mL of dichloromethane. The combined organic phases were dried over $Na_2SO_4$, filtered, and concentrated. The crude extract was dissolved in 40 mL of water and passed through Amberlite (IR120H) column to remove all the small molecules. The collected aqueous solution was stirred with 50 mL of dichloromethane and charged with 10.5 g of NaCl (15 w/v % of water). Two layers were separated and the aqueous phase was extracted with 40 mL of dichloromethane. The combined organic phases were dried over $Na_2SO_4$, filtered, concentrated, and dried in vacuo to give the desired product 4-arm PEG-Gly-Rotigotine. HCl K (1.58 g, 74% yield).

$^1$H NMR (Varian, 500 MHz, 10 mg/mL $CDCl_3$) showed the polymer backbone peaks at 3.64 ppm (m, 4H, —($OCH_2CH_2$)$_n$—) and other major peaks at 1.03 ppm (d, 3H, —$CH_2CH_2CH_3$), 6.95 ppm (m, 3H, aromatic), 7.06 ppm (t, 1H, thiophenyl), 7.20 ppm (m, 2H, thiophenyl), and 7.81 ppm (m, 1H, triazole). The average number of rotigotine molecules on each polymer was determined as 2.53 by $^1$H NMR analysis.

Example 17—Preparation of H-[(Ethyl-Tiagabine)$_{10}$(EOZ)$_{190}$]—COOH 20K by Attachment of Tiagabine 3-azidoacetate to Polyoxazoline 10 Pendent Acid 20K

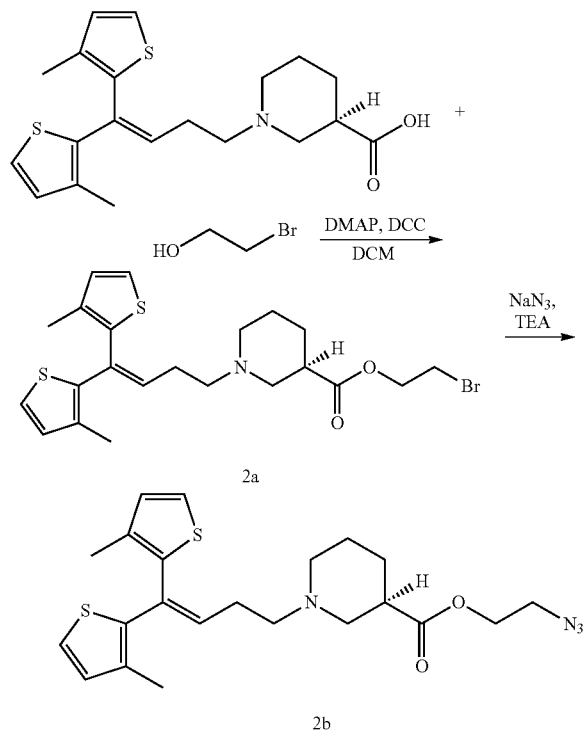

In a 250 mL round bottom flask, tiagabine (2.00 gm, 5.33 mmol), 4-DMAP (658 mg, 5.33 mmol) were dissolved in anhydrous ACN (100 mL). ACN was completely evaporated by rotary-evaporation. DCM (100 mL) was added to dissolve the residual, which was allowed to stir under argon. To the solution 2-bromoethanol (1.17 mL, 15.98 mmol) and DCC were added (1.16 gm, 5.59 mmol). The solution was allowed to stir at room temperature for overnight. The pink solution turned cloudy. Following overnight of reaction, the reaction mixture was analyzed by reversed phase HPLC, which indicated 98% of conversion to 2-bromoethyl tiagabine. The reaction mixture was filtered; the pink filtrate was washed twice with 0.1 N HCl using 100 mL each time in a separatory funnel. Following phase separation, DCM phase was dried over anhydrous sodium sulfate (100 gm). The mixture was filtered through glass frit. The filtrate was concentrated to dryness by rotary-evaporation. The residual was dissolved in DCM (30 mL). White precipitate was filtered off. The filtrate was concentrated to 10 mL, which was then added into hexanes (300 mL) to precipitate. The solid was collected in a glass frit following filtration, and dried in vacuum to provide compound 2a as solid powder (2.1 gm, Yield: 72%). NMR analysis of 2a in deuterated chloroform showed the relevant peaks at 4.405 ppm (t, 2H, BrCH$_2$CH$_2$O—); 3.496 ppm (t, 2H, BrCH$_2$CH$_2$O—); 7.251 ppm (d, 1H, —S—CH═CH—); 7.095 ppm (d, 1H, —S—CH═CH—); 6.889 ppm (d, 1H, —S—CH═CH—); 6.774 ppm (d, 1H, —S—CH═CH—); 5.965 ppm (t, 1H, ═CHCH$_2$—); 2.030 ppm (s, 3H, CH$_3$—); 1.983 ppm (s, 3H, CH$_3$—). 1.455 ppm-3.653 ppm (m, 16H, CH$_3$— and BrCH$_2$— not included).

To 2-Bromoethyl Tiagabine·HCl salt (2a) (2.00 gm, 3.70 mmol) in a 100 mL round bottom flask with 20 mL of anhydrous DMF, TEA (1.11 mL, 7.98 mmol) and NaN$_3$ (262 mg, 3.99 mmol) were added into the solution. The solution was allowed to stir at 40° C. with an oil bath under argon atmosphere. Following overnight of stirring, DMF was evaporated at 40° C. under vacumm by rotary-evaporation. Ethyl acetate (100 mL) and 0.1 N HCl (60 mL) was added to the mixture, stirred, and then transferred into a separatory funnel. Following phase separation, the aqueous phase was extracted by ethyl acetate again (100 mL). The ethyl acetate layer was combined, washed with 0.1 N HCl (20 mL). The ethyl acetate layer was then dried over sodium sulfate (100 gm). Following filtration, the clear filtrate was concentrated to 20 mL in a 250 mL round bottom flask by rotary evaporation. To the mixture hexanes (200 mL) was added to precipitate the product. The solid was collected into a glass frit following filtration, and dried overnight in vacuum, which provide 1.38 gm of crude product in solid form. The crude product (1.0 gm) was re-dissolved in a solution of 0.1% TFA in ACN (24 mL), and then 0.1% TFA in water (96 mL). White precipitate in the mixture was filtered off. The filtrate was then purified by reversed phase chromatography with a SunFire Prep C8 OBD 30/250 Column from Waters using a UV detector at wavelength 214 nm at a flow rate of 20 mL/min. 0.1% TFA in water (Mobile phase A) and 0.1% TFA in ACN (Mobile phase B) were used as mobile phases for the purification. The column was equilibrated with 20% B. Following loading of the crude product, the column was initially eluted isocratically with 20% of mobile phase B. The gradient was ramped to 35% mobile phase B in 15 minutes, and then eluted isocratically with 35% of mobile phase B. The product fraction was collected when the column was eluted with 35% mobile phase B. The solution was evaporated by rotary evaporation to remove ACN. The remaining aqueous solution was extracted by DCM (3×120 mL). Following phase separation, DCM phase was dried over anhydrous sodium sulfate (100 gm). The solid was filtered off, and the filtrate was concentrated by rotary-evaporator to near dryness, and then dried in vacuum to provide compound 2b as viscous oil (0.89 gm). NMR analysis in deuterated chloroform showed the relevant peaks at 4.272 ppm (m, 2H, N$_3$CH$_2$CH$_2$O—); 3.483 ppm (t, 2H, N$_3$CH$_2$CH$_2$O—); 7.251 ppm (d, 1H, —S—CH═CH—); 7.091 ppm (d, 1H, —S—CH═CH—); 6.883 ppm (d, 1H, —S—CH═CH—); 6.769 ppm (d, 1H, —S—CH═CH—); 5.934 ppm (t, 1H, ═CHCH$_2$—); 2.021 ppm (s, 3H, CH$_3$—); 1.972 ppm (s, 3H, CH$_3$—). 1.455 ppm-3.733 ppm (m, 16H, CH$_3$— and BrCH$_2$— not included). HPLC purity 99%.

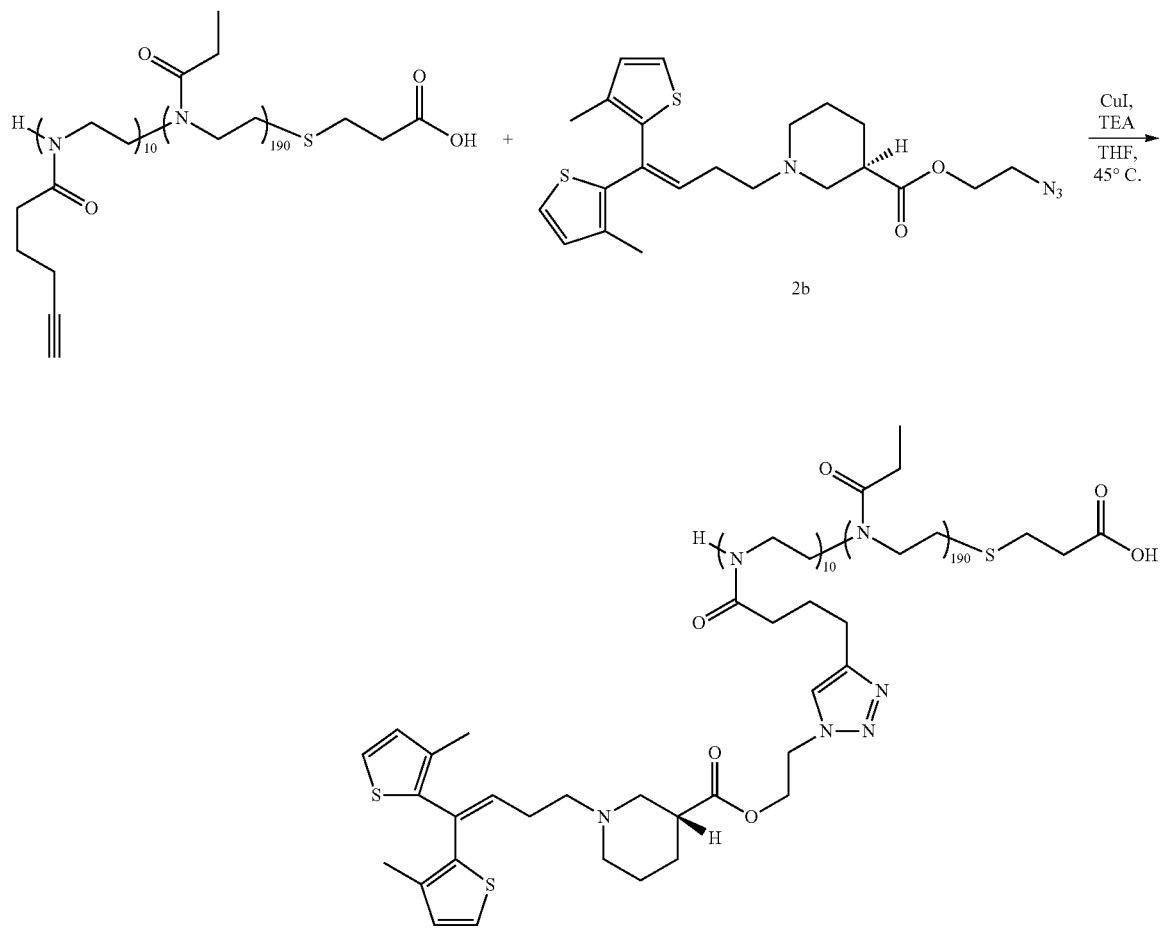

H-[(PtynOZ)$_{10}$(EOZ)$_{190}$]-T-PA (1.13 gm, 0.0577 mmol) was dissolved in THF (25 mL) in a 100 mL RB flask with 2-azidoethyl tiagabine·HCl salt (2b) (344.5 mg, 0.635 mmol). The solution was protected under argon. CuI (44.2 mg, 0.231 mmol) was then added to the flask, followed by immediate addition of TEA (0.12 mL, 0.866 mmol). The solution, which turned greenish, was stirred at 45° C. for overnight under argon atmosphere. The solution was filtered to remove solid. 0.1 N HCl (20 mL) was added into the filtrate. THF in the mixture was then evaporated by rotary-evaporator. The remaining aqueous solution (20 mL) was then loaded to a column (2 cm i.d.) packed with Dowex® M4195 media (20 gm) over silica gel 60 (14 gm), which was equilibrated in 2 mM HCl, to remove copper ion. The column was eluted with 2 mM HCl until no POZ-Tiagabine conjugate was retained on the column. To remove low molecular weight tiagabine related species (tiagabine and 2-azidoethyl tiagabine), the collected eluate (175 mL) was then applied to a column packed with Amberlite TR-120 (41 gm) resin, followed by elution with 2 mM HCl until POZ-Tiagabine conjugate completely eluted. NaCl (15 gm) was added to the collected eluate (300 mL) to make 5% brine.

The solution was extracted with DCM (3×100 mL). Following phase separation, the DCM phases were pooled, and dried over anhydrous sodium sulfate (100 gm) for one hour. The mixture was filtered through a glass fit to remove sodium sulfate. The filtrate was concentrated to 25 mL by rotary evaporation, and then precipitated in 500 mL of diethyl ether. The precipitate was collected when the mixture was filtered through a glass frit, and then dried in vacuum, which yield 1.1 gm of polyoxazoline pendent 2-ethyl tiagabine (4) as white powder. HPLC analysis indicated that POZ-Tiagabine conjugate did not contain free tiagabine, or 2-azidoethyl tiagabine. NMR analysis of polyoxazoline pendent 2-ethyl tiagabine in deuterated chloroform showed the relevant peaks at 7.548 ppm (m, ill resolved, nH, =CH—N); 7.256 ppm (d, nH, —S—CH=CH—); 7.087 ppm (d, nH, —S—CH=CH—); 6.888 ppm (d, nH, —S—CH=CH—); 6.772 ppm (d, nH, —S—CH=CH—); 5.958 ppm (t, nH, =CHCH$_2$—); 4.761 ppm (t, ill resolved, 2nH, —C(=O)CH$_2$CH$_2$CH$_2$—); 4.494 ppm (m, 2nH, N$_3$CH$_2$CH$_2$O—); 3.449 ppm, 2.406 ppm and 1.120 ppm (polymer backbone). Average number (n) of pendent tiagabine molecule on each POZ was 9.4.

Example 18—Preparation of H-[(Propyl-Tiagabine)$_{10}$(EOZ)$_{190}$]—COOH 20K by Attachment of Tiagabine 3-azidopropionate to Polyoxazoline 10 Pendent Acid 20K

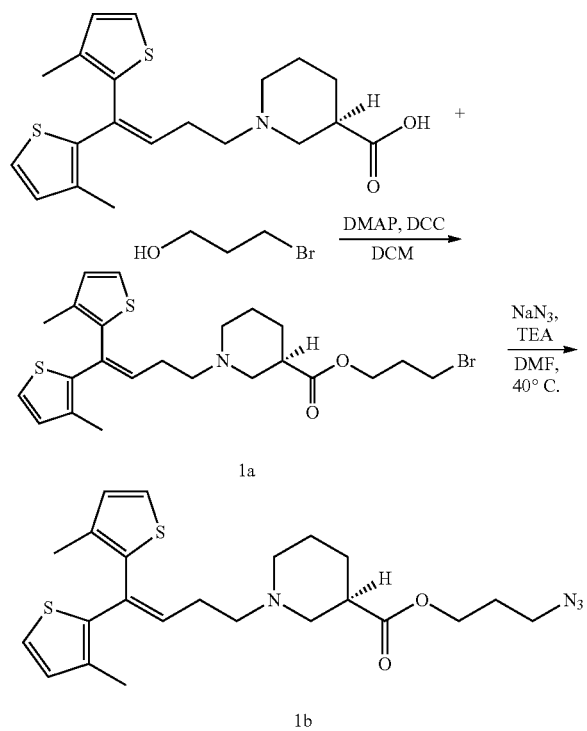

In a 250 mL round bottom flask, tiagabine (2.00 gm, 5.33 mmol), 4-DMAP (658 mg, 5.33 mmol) were dissolved in anhydrous ACN (100 mL). ACN was completely evaporated by rotary-evaporation. DCM (100 mL) was added to dissolve the residual, which was allowed to stir under argon. To the solution 3-bromo-1-propanol (1.49 mL, 15.98 mmol) and DCC were added (1.16 gm, 5.59 mmol). The solution was allowed to stir at room temperature for overnight. The pink solution turned cloudy. Following overnight of reaction, the reaction mixture was analyzed by reversed phase HPLC, which indicated 96% of conversion to 3-bromopropyl tiagabine ester. The reaction mixture was filtered; the pink filtrate was washed twice with 0.1 N HCl using 100 mL each time in a separatory funnel. Following phase separation, DCM phase was dried over anhydrous sodium sulfate. The mixture was filtered through glass frit. The filtrate was concentrated to dryness by rotary-evaporation. The residual was further dried in vacuum. The residual crude product was re-dissolved in a solution of 0.1% TFA in ACN (42 mL), and then 0.1% TFA in water (78 mL). White precipitate in the mixture was filtered off. The filtrate was then purified by reversed phase chromatography with a SunFire Prep C8 OBD 30/250 Column from Waters using a UV detector at wavelength 214 nm. 0.1% TFA in water (Mobile phase A) and 0.1% TFA in ACN (Mobile phase B) were used as mobile phases for the purification. The column was equilibrated with 35% B. Following loading of the crude product, the column was eluted isocratically with 35% of mobile phase B. The product fraction was collected and analyzed by reversed phase HPLC. The solution was evaporated by rotary evaporation to remove ACN. The remaining aqueous solution was extracted by DCM (3×250 mL). Following phase separation, DCM phase was dried over anhydrous sodium sulfate (100 gm). The solid was filtered off, and the filtrate was concentrated by rotary-evaporator to near dryness, and then dried in vacuum to provide compound 1a as viscous oil (1.83 gm, yield: 56%). NMR analysis in deuterated chloroform showed the relevant peaks at 4.247 ppm (t, 2H, BrCH$_2$CH$_2$CH$_2$O—); 3.441 ppm (t, 2H, BrCH$_2$CH$_2$CH$_2$O—); 7.253 ppm (d, 1H, —S—CH═CH—); 7.094 ppm (d, 1H, —S—CH═CH—); 6.884 ppm (d, 1H, —S—CH═CH—); 6.771 ppm (d, 1H, —S—CH═CH—); 5.932 ppm (t, 1H, ═CHCH$_2$—); 2.029 ppm (s, 3H, CH$_3$—); 1.973 ppm (s, 3H, CH$_3$—). 1.455 ppm-3.668 ppm (m, 16H, CH$_3$— and BrCH$_2$— not included). HPLC purity 98%.

To the 3-Bromopropyl Tiagabine Ester·TFA salt (1.80 gm, 2.89 mmol) in a 100 mL round bottom flask with 20 mL of anhydrous DMF, TEA (806 µL, 5.78 mmol) and NaN$_3$ (188 mg, 2.89 mmol) were added into the solution. The solution was allowed to stir at 40° C. with an oil bath under argon atmosphere. Following overnight of stirring, DMF was evaporated at 40° C. under vacuum by rotary-evaporation. Ethyl acetate (100 mL) and 0.1 N HCl (60 mL) was added to the mixture, stirred, and then transferred into a separatory funnel. Following phase separation, the aqueous phase was extracted by ethyl acetate again (100 mL). The ethyl acetate layer was combined, washed with deionized water (50 mL). The ethyl acetate layer was then dried over sodium sulfate. Following filtration, the clear filtrate was concentrated to dryness by rotary evaporation. The residual was further dried in vacuum to provide compound 1b as viscous oil (1.53 gm, Yield: 97%). NMR analysis in deuterated chloroform showed the relevant peaks at 4.190 ppm (t, 2H, N$_3$CH$_2$CH$_2$CH$_2$O—); 3.388 ppm (t, 2H, N$_3$CH$_2$CH$_2$CH$_2$O—); 7.253 ppm (d, 1H, —S—CH═CH—); 7.093 ppm (d, 1H, —S—CH═CH—); 6.884 ppm (d, 1H, —S—CH═CH—); 6.771 ppm (d, 1H, —S—CH═CH—); 5.937 ppm (t, 1H, ═CHCH$_2$—); 2.021 ppm (s, 3-H, CH$_3$—); 1.973 ppm (s, 3H, CH$_3$—); 1.457 ppm-3.683 ppm (m, 16H, CH$_3$— and N$_3$CH$_2$— not included). HPLC purity 92%.

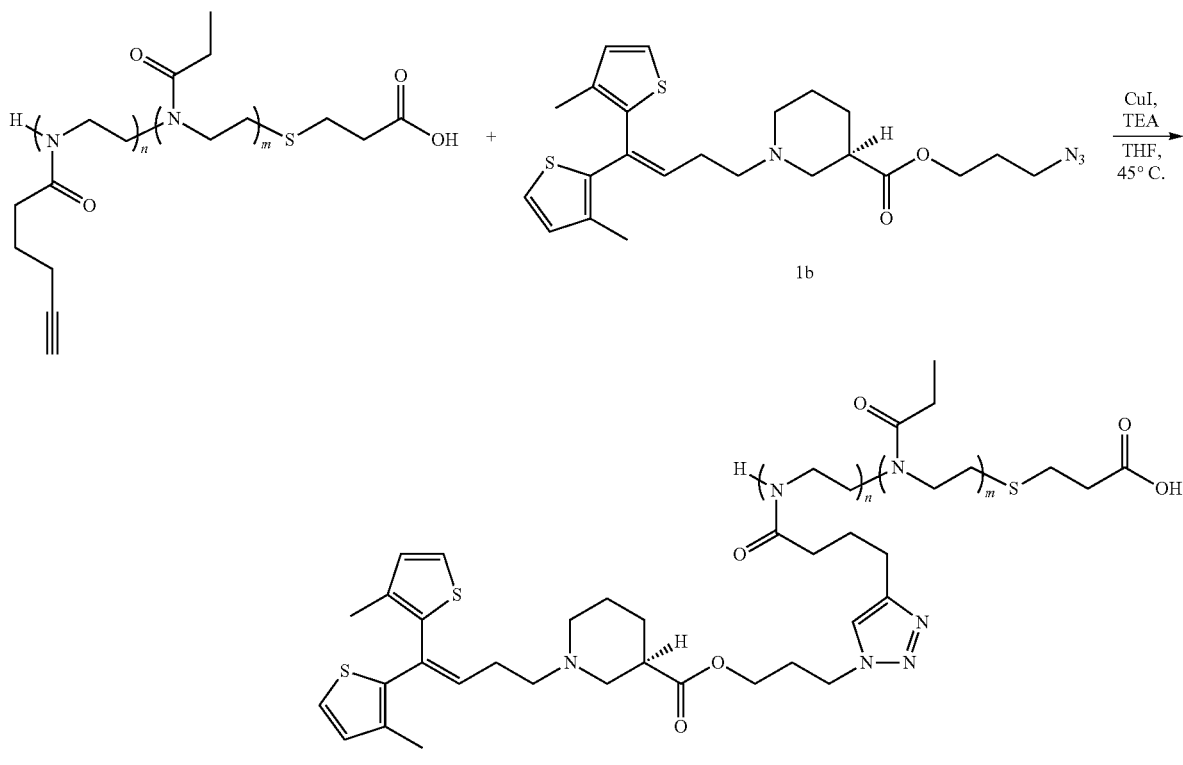

H-[(PtynOZ)$_{10}$(EOZ)$_{190}$]-T-PA (1.13 gm, 0.0577 mmol) was dissolved in THF (25 mL) in a 100 mL RB flask with 3-Azidopropyl Tiagabine Ester·HCl salt (338.7 mg, 0.635 mmol). The solution was protected under argon. CuI (44.2 mg, 0.231 mmol) was then added to the flask, followed by immediate addition of TEA (0.12 mL, 0.866 mmol). The solution, which turned greenish, was stirred at 45° C. for overnight under argon atmosphere. The greenish solution was filtered to remove solid. 0.1 N HCl (20 mL) was added into the filtrate. THF in the mixture was then evaporated by rotary-evaporator. The remaining aqueous solution (20 mL) was then loaded to a column (2 cm i.d.) packed with Dowex® M4195 media (20 gm) over silica gel 60 (14 gm), which was equilibrated in 2 mM HCl, to remove copper ion. The column was eluted with 2 mM HCl until no POZ-Tiagabine conjugate was retained on the column. To remove low molecular weight tiagabine related species (tiagabine and 3-azidopropyl tiagabine ester), the collected eluate (175 mL) was then applied to a column packed with Amberlite IR-120 (41 gm) resin, followed by elution with 2 mM HCl until POZ-Tiagabine conjugate completely eluted. NaCl (15 gm) was added to the collected eluate (300 mL) to make 5% brine. The solution was extracted with DCM (3×100 mL). Following phase separation, the DCM phases were pooled, and dried over anhydrous sodium sulfate (100 gm) for one hour. The mixture was filtered through a glass frit to remove sodium sulfate. The filtrate was concentrated to 25 mL by rotary evaporation, and then precipitated in 500 mL of diethyl ether. The precipitate was collected when the mixture was filtered through a glass frit, and then dried in vacuum, which yield 1.1 gm of white powder. HPLC analysis indicated that POZ-Tiagabine conjugate did not contain free Tiagabine, or 3-Azidopropyl Tiagabine Ester. NMR analysis in deuterated chloroform showed the relevant peaks at 7.55 ppm (m, ill resolved, nH, =CH—N), -); 7.258 ppm (d, nH, —S—CH=CH—); 7.093 ppm (d, nH, —S—CH=CH—); 6.881 ppm (d, nH, —S—CH=CH—); 6.769 ppm (d, nH, —S—CH=CH—); 5.964 ppm (t, nH, =CHCH$_2$—); 4.425 ppm (t, ill resolved, 2nH, —C(=O)CH$_2$CH$_2$CH$_2$—); 3.463 ppm, 2.406 ppm and 1.120 ppm (polymer backbone).

Example 19—Preparation of H-[(PEG3-Tiagabine)$_{10}$(EOZ)$_{190}$]COOH 20K by Attachment of 2-[2-(2-Azidoethoxy)ethoxy]ethyl Tiagabine Ester to Polyoxazoline 10 Pendent Acid 20K

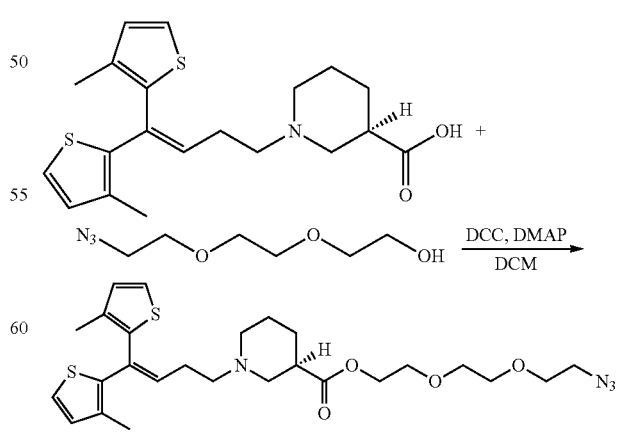

In a 100 mL round bottom flask, tiagabine (786 mg, 2.092 mmol, 1.0 equiv.), 4-DMAP (258 mg, 2.092 mmol, 1.0 equiv.), and 2-[2-(2-Azidoethoxy)ethoxy]ethanol (733 mg, 4.185 mmol, 2.0 equiv.) were dissolved in anhydrous acetonitrile (CAN, 40 mL). ACN was completely evaporated by rotary-evaporation at 25° C. Anhydrous dichloromethane (DCM, 35 mL) was added to dissolve the residue and stirred in an argon atmosphere. To this solution DCC (458 mg, 2.197 mmol, 1.05 equiv.) was added. The solution was allowed to stir at room temperature overnight. The reaction mixture was next filtered to remove solid precipitate and the pink colored DCM filtrate was washed with 0.1 N HCl (2×50 mL) in a separatory funnel. Following phase separation, the DCM phase was dried over anhydrous sodium sulfate, filtered and then concentrated to dryness by rotary evaporation. The residue was further dried under vacuum and the resultant product was 1.35 gm of crude 2-[2-(2-Azidoethoxy)ethoxy]ethyl Tiagabine Ester. This crude powder was next dissolved in 0.1% TFA in ACN (35 mL), followed by addition of 0.1% TFA in water (65 mL). The mixture was filtered through a glass frit to remove white precipitate. The filtrate was further filtered through a 0.45 µm membrane and then purified by preparative reverse phase chromatography using a SunFire Prep C8 OBD 30/250 Column (Waters Corp) and a UV detector set at a wavelength of 214 nm. The elution media used in the purification was 0.1% TFA in water (Mobile phase A) and 0.1% TFA in ACN (Mobile phase B). The column was equilibrated with 35% B. Following loading of the crude product, the column was eluted isocratically with 35% of mobile phase B. The eluted product fraction was evaporated by rotary evaporation to remove ACN. The remaining aqueous solution was then extracted with DCM (3 times×250 mL). Following phase separation each time, DCM phase was collected and dried over anhydrous sodium sulfate (100 gm). The solid was filtered off, and the filtrate was concentrated by rotary-evaporation to near dryness, and then dried under vacuum to yield 2-[2-(2-Azidoethoxy)ethoxy]ethyl Tiagabine Ester as a viscous oil (567 mg, yield: 42%).

The product was analyzed by reverse phase HPLC to confirm purity of 98%. NMR analysis in deuterated chloroform showed the relevant peaks at 4.255 ppm (t, 2H, —C(=O)OCH$_2$CH$_2$O—); 3.652-3.703 ppm (m, 4×2H, —OCH$_2$CH$_2$O—, —C(=O)OCH$_2$CH$_2$O—, —OCH$_2$CH$_2$N$_3$); 3.387 ppm (t, 2H, —CH$_2$N$_3$); 7.249 ppm (d, 1H, —S—CH=CH—); 7.089 ppm (d, 1H, —S—CH=CH—); 6.879 ppm (d, 1H, —S—CH=CH—); 6.767 ppm (d, 1H, —S—CH=CH—); 5.932 ppm (t, 1H, =CHCH$_2$—); 2.029 ppm (s, 3H, CH$_3$—); 1.973 ppm (s, 3H, CH$_3$—). 1.455 ppm-3.550 ppm (m, 13H).

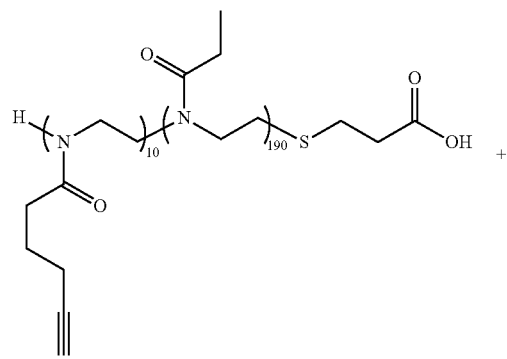

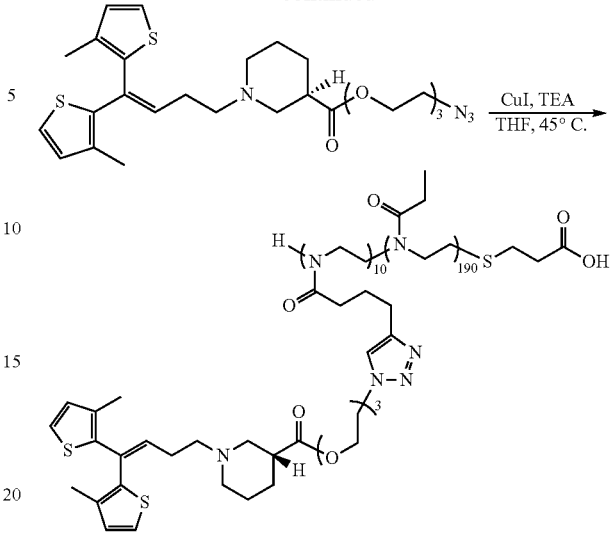

H-[(PtynOZ)$_{10}$(EOZ)$_{190}$]-T-PA (1.65 gm, 0.0847 mmol) was dissolved in tetrahydrofuran (THF, 35 mL) in a 100 mL RB flask with 2-[2-(2-Azidoethoxy)ethoxy]ethyl Tiagabine Ester (561 mg, 0.847 mmol). The solution was mixed in an argon atmosphere. Copper Iodide (CuI, 65 mg, 0.339 mmol) was then added to the flask, followed by immediate addition of triethylamine (TEA, 0.18 mL, 1.270 mmol). The solution, which turned greenish, was stirred at 45° C. for overnight under argon atmosphere. The greenish solution was then filtered to remove any solid residue, and 0.1 N HCl acid (30 mL) was then added to the filtrate. The THF in the mixture was then evaporated by rotary-evaporator. The remaining aqueous solution (30 mL) was then loaded to a column (2 cm i.d.) packed with Dowex® M4195 media (30 gm) over silica gel 60 (20 gm), which was equilibrated in 2 mM HCl, to remove any soluble copper ion species. The column was eluted with 2 mM HCl until no POZ-Tiagabine conjugate was retained on the column. To remove low molecular weight free tiagabine and unreacted 2-[2-(2-Azidoethoxy)ethoxy]ethyl Tiagabine Ester species, the collected eluent (256 mL) was loaded onto a column packed with Amberlite IR-120 (60 gm) resin, and then eluted with 2 mM HCl acid. To the aqueous solution (400 mL) containing the desired POZ-Tiagabine conjugate, was added NaCl (20 gm) to make a brine solution with approximately 5% salt. This solution was extracted with DCM (3 times×145 mL). Following phase separation, the DCM phases were pooled, and dried over anhydrous sodium sulfate (145 gm) for one hour. The mixture was filtered through a glass frit to remove sodium sulfate. The filtrate was concentrated to 30 mL by rotary evaporation, and then precipitated in 650 mL of diethyl ether. The precipitate was collected when the mixture was filtered through a glass frit, and then dried in vacuum, which yield 1.5 gm of white powder. HPLC analysis showed that the desired POZ-Tiagabine conjugate did not contain free Tiagabine, or unreacted 2-[2-(2-Azidoethoxy)ethoxy]ethyl Tiagabine ester. NMR analysis in deuterated chloroform showed the relevant peaks at 7.72 ppm (m, ill resolved, nH, =CH—N); 7.258 ppm (d, nH, —S—CH=CH—); 7.093 ppm (d, nH, —S—CH=CH—); 6.884 ppm (d, nH, —S—CH=CH—); 6.769 ppm (d, nH, —S—CH=CH—); 5.962 ppm (t, nH, =CHCH$_2$—); 4.575 ppm (t, ill resolved, 2nH, —C(=O)CH$_2$CH$_2$CH$_2$—); 3.472 ppm, 2.406 ppm and 1.120 ppm (polymer backbone).

Example 20—Preparation of H-[(Phenyl-Tiagabine)$_{10}$(EOZ)$_{190}$]—COOH 20K by Attachment of Tiagabine 3-azido-N-(4-hydroxyphenyl) propanamide Ester to Polyoxazoline 10 Pendent Acid 20K

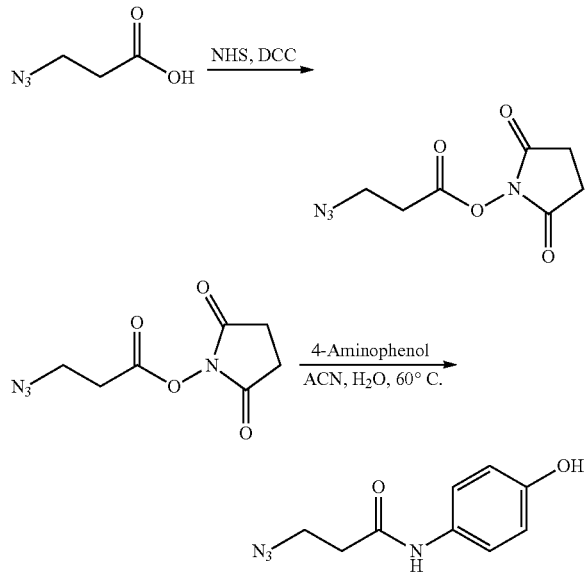

Succinimidyl Azidopropionate:

3-Azidopropionic acid (5.00 gm, purity 95.4%, 41.446 mmol, 1.0 eq.) and N-hydroxysuccinimide (NHS, 4.87 gm, 41.446 mmol, 1.0 eq.) were dissolved in DCM (150 mL), followed by addition of DCC (8.64 gm, 41.446 mmol, 1.0 eq). The solution was allowed to stir under argon at room temperature. Following overnight of reaction, the cloudy mixture was filtered to remove white precipitate. The filtrate was evaporated by rotary evaporation to dryness. The residual was dissolved in ACN (100 mL) and any white precipitate present in ACN was filtered off. The filtrate was evaporated to dryness, by rotary evaporation, followed by further drying under vacuum. The resultant product of succinimidyl azidopropionate was 9.7 gm. NMR analysis in DMSO-d6 showed the relevant peaks at 3.659 ppm (t, 2H, N$_3$CH$_2$—); 3.012 ppm (t, 2H, —N$_3$CH$_2$CH$_2$—); 2.822 ppm (s, 4H, —OSu). Reverse phase HPLC purity was 95%.

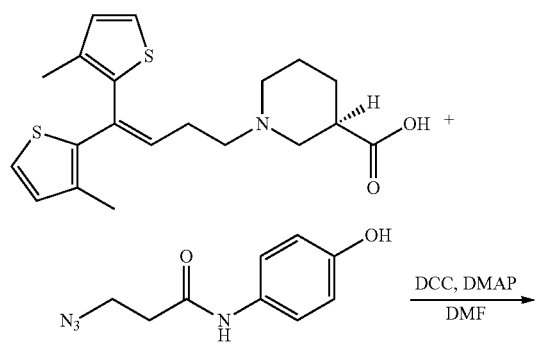

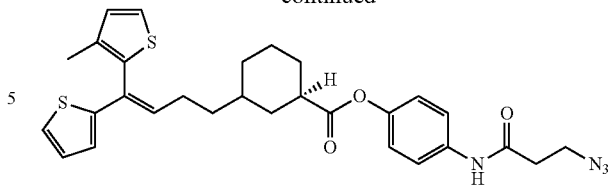

3-Azido-N-(4-hydroxyphenyl)propanamide:

In the next step, 4-aminophenol (1.47 gm, 13.433 mmol, 0.75 eq.) was dissolved in an ACN-water mixed solvent (1:1 v/v, 60 mL) at 60° C. The solution was transferred into the round bottom flask which contained the succinimidyl azidopropionate (4.00 gm, 17.911 mmol, 1.0 eq.). The solution was allowed to stir at 60° C. under Argon atmosphere. Following overnight of reaction, the mixture was filtered through a 0.45 μm membrane. The filtrate was evaporated to remove ACN completely and during the process a precipitate was formed in the remaining aqueous solution. The supernatant was decanted and the residual precipitate was next washed with DI water (30 mL), decanted, and then redissolved in ACN (30 mL). The solution was placed on a rotary evaporator and the solvent was evaporated to leave behind a residue that required additional drying under vacuum. The dried product was 0.79 gm of 3-Azido-N-(4-hydroxyphenyl)propanamide. NMR analysis in DMSO-d6 showed the relevant peaks at 7.352 ppm (d, 2×1H, phenyl); 6.684 ppm (d, 2×1H, phenyl); 3.590 ppm (t, 2H, N$_3$CH$_2$CH$_2$—); 2.552 ppm (t, 2H, N$_3$CH$_2$CH$_2$—). 4-(3-Azidopropanamido)phenyl Tiagabine Ester: In a 250 mL round bottom flask, 3-Azido-N-(4-hydroxyphenyl)propanamide (787 mg, 3.641 mmol, 2.0 eq.), tiagabine (684 mg, 1.821 mmol, 1.0 equiv.), 4-DMAP (225 mg, 1.821 mmol, 1.0 equiv.) were dissolved in 19 mL of anhydrous ACN (10 mL). ACN was completely evaporated by rotary-evaporation at 28° C. DMF (15 mL) was added to dissolve the residual, which was allowed to stir under argon. To the solution DCC were added (398 mg, 1.912 mmol, 1.05 equiv.). The solution was allowed to stir at room temperature overnight. The reaction mixture was evaporated at 35° C. under vacuum to remove DMF. The residual was dissolved in 0.1% TFA in ACN (35 mL), followed by addition of 0.1% TFA in water (65 mL). The mixture was filtered through a glass frit to remove white precipitate. The filtrate was further filtered through a 0.45 μm membrane. The filtrate was then purified by reversed phase chromatography with a SunFire Prep C8 OBD 30/250 Column from Waters using a UV detector at wavelength 214 nm. 0.1% TFA in water (Mobile phase A) and 0.1% TFA in ACN (Mobile phase B) were used as mobile phases for the purification. The product fraction was collected and analyzed by reversed phase HPLC. The solution was evaporated by rotary evaporation to remove ACN. The remaining aqueous solution was extracted by DCM (3×250 mL). Following phase separation, DCM phase was dried over anhydrous sodium sulfate (100 gm). The solid was filtered off, and the filtrate was concentrated by rotary-evaporator to near dryness, and then dried in vacuum to provide 4-(3-Azidopropanamido)phenyl Tiagabine Ester as viscous oil (484 mg). NMR analysis in deuterated chloroform showed the relevant peaks at 7.563 ppm (d, 2H, phenyl); 6.996 ppm (d, 2H, phenyl); 7.235 ppm (d, 1H, —S—CH═CH—); 7.089 ppm (d, 1H, —S—CH═CH—); 6.874 ppm (d, 1H, —S—CH═CH—); 6.768 ppm (d, 1H, —S—CH═CH—); 5.946 ppm (t, 1H, ═CHCH$_2$—); 3.725 ppm (t, 2H, N$_3$CH$_2$—); 2.620 ppm (t, 2H, N$_3$CH$_2$CH$_2$—); 2.029 ppm (s, 3H, CH$_3$—); 1.973 ppm (s, 3H, CH$_3$—). HPLC purity 92%.

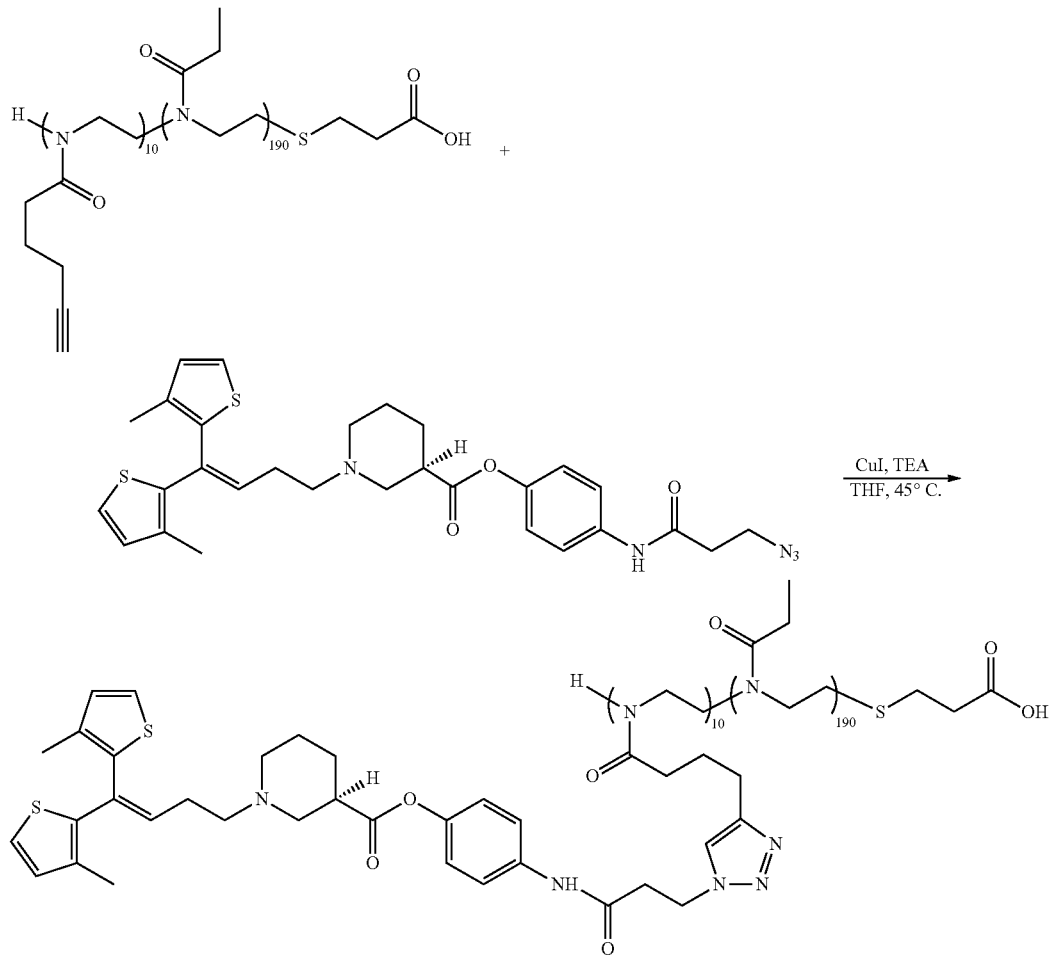

H-[(PtynOZ)$_{10}$(EOZ)$_{190}$]-T-PA (1.29 gm, 0.0659 mmol) was dissolved in THF mL) in a 100 mL RB flask with 4-(3-Azidopropanamido)phenyl Tiagabine Ester (484 mg, 0.659 mmol) in an argon atmosphere. Copper iodide (CuI, 50 mg, 0.264 mmol) was then added to the flask, followed by immediate addition of triethylamine (TEA, 0.14 mL, 0.989 mmol). The solution, which turned greenish, was stirred at 45° C. for overnight under argon atmosphere. The greenish solution was filtered to remove solid and 0.1 N HCl acid (24 mL) was added to the filtrate. THF in the mixture was then evaporated by rotary-evaporation and the remaining aqueous solution (24 mL) became cloudy. 2 mM HCl acid (26 mL) was added into the aqueous mixture to dissolve the insoluble material and clarify the solution. The solution was then loaded onto a column (2 cm i.d.) packed with Dowex® M4195 media (24 gm) over silica gel 60 (16 gm), which was equilibrated in 2 mM HCl, to remove copper ion. The column was eluted with 2 mM HCl until no POZ-Tiagabine conjugate was retained on the column. To remove the low molecular weight free tiagabine and unreacted 4-(3-Azidopropanamido)phenyl Tiagabine Ester, the collected eluent (205 mL) was loaded onto a column packed with Amberlite IR-120 (48 gm) resin, and then eluted with 2 mM HCl acid. The eluent (320 mL) was collected and NaCl (16 gm) was added to it to make a brine solution with 5% salt. The solution was extracted with DCM (3 times×100 mL). Following phase separation each time, the DCM phases were collected, pooled, and dried over anhydrous sodium sulfate (100 gm) for one hour. The mixture was filtered through a glass frit to remove sodium sulfate. The filtrate was concentrated to 30 mL by rotary evaporation, and then precipitated in to 400 mL of diethyl ether. The precipitate was collected when the mixture was filtered through a glass frit, and then dried in vacuum, to yield 1.2 gm of white powder.

HPLC analysis indicated that POZ-Tiagabine conjugate did not contain free Tiagabine, or 4-(3-Azidopropanamido)

phenyl Tiagabine Ester. NMR analysis in deuterated chloroform showed the relevant peaks at 7.607 ppm (d, ill resolved, 2nH, phenyl); 7.548 ppm (m, ill resolved, nH, =CH—N); 7.245 ppm (d, nH, —S—CH=CH—); 7.091 ppm (d, nH, —S—CH=CH—); 6.942 ppm (d, ill resolved, 2H, phenyl); 6.874 ppm (d, nH, —S—CH=CH—); 6.767 ppm (d, nH, —S—CH=CH—); 5.970 ppm (t, nH, =CHCH$_2$—); 4.705 ppm (t, ill resolved, 2nH, —C(=O)CH$_2$CH$_2$CH$_2$—); 3.457 ppm, 2.401 ppm and 1.118 ppm (polymer backbone).

Example 21—Coupling of 4-Arm PEG-acetylene (10K) to Azidopropyl Tiagabine

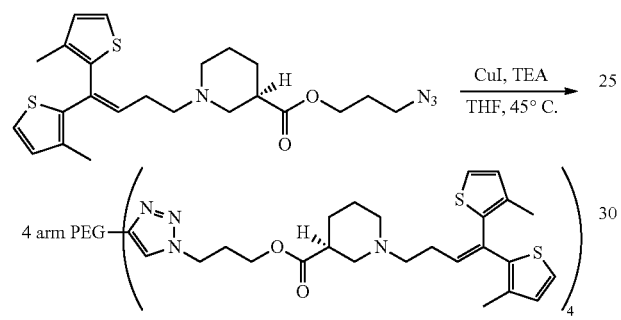

4arm PEG-Alkyne 10K (1.59 gm, 0.144 mmol from Creative PEGWorks) was dissolved in 25 mL of THF in a 100 mL RB flask with 3-Azidopropyl-Tiagabine Ester·HCl salt (338.7 mg, 0.635 mmol). The solution was protected under Ar, and heated to 45° C. to dissolve. CuI (44.2 mg, 0.231 mmol) was then added to the flask, followed by immediate addition of TEA (120.6 µL, 0.866 mmol). The solution was stirred at 45° C. for overnight under argon atmosphere. The solution was filtered to remove, solid. 0.1 N HCl (20 mL) was added into the filtrate. THF in the mixture was then evaporated by rotary-evaporator. The remaining aqueous solution (20 mL) was then loaded to a column (2 cm i.d.) packed with Dowex® M4195 media (20 gm), which was equilibrated in 2 mM HCl, to remove copper ion. The column was eluted with 2 mM HCl until no PEG-Tiagabine conjugate was retained on the column. To remove low molecular weight tiagabine related species (tiagabine and 3-azidopropyl tiagabine ester), the collected eluate was then applied to a column packed with Amberlite IR-120 (41 gm) resin, followed by elution with 2 mM HCl until PEG-Tiagabine conjugate completely eluted. NaCl (11 gm) was added to the collected eluate (220 mL) to make 5% brine. The solution was extracted with DCM (3×100 mL). Following phase separation, the DCM phases were pooled, and dried over anhydrous sodium, sulfate (100 gm) for one hour. The mixture was filtered through a glass frit to remove sodium sulfate. The filtrate was concentrated to 3 mL by rotary evaporation, and then precipitated in diethyl ether (200 mL). The precipitate was collected when the mixture was filtered through a glass fit, and then dried in vacuum, which yield 1.4 gm of white powder. NMR analysis in deuterated chloroform showed the relevant peaks at 7.62 ppm (s, 4H, =CH—N), -); 7.259 ppm (d, 4H, —S—CH=CH—); 7.096 ppm (d, 4H, —S—CH=CH—); 6.883 ppm (d, 4H, —S—CH=CH—); 6.772 ppm (d, 4H, —S—CH=CH—); 5.967 ppm (t, 4H, =CHCH$_2$—); 4.440 ppm (t, ill resolved, 8H, —C(=O)CH$_2$CH$_2$CH$_2$—); 3.64 ppm (PEG backbone). Average number of Tiagabine molecule on each 4arm-PEG was 3.2.

Example 22—Preparation of H-[(Carbamate-Ropinirole)$_{10}$(EOZ)$_{190}$]—COOH 20K by Attachment of Ropinirole 3-azidocarbamate to Polyoxazoline 10 Pendent Acid 20K

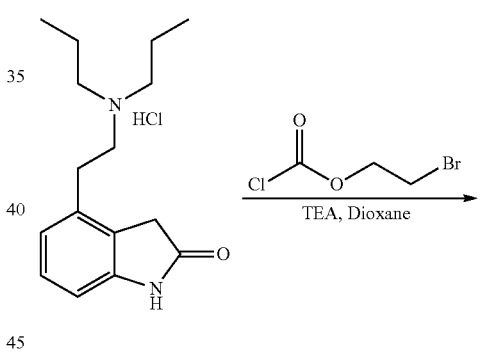

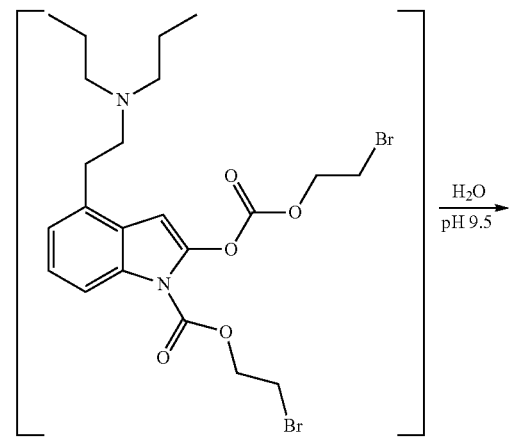

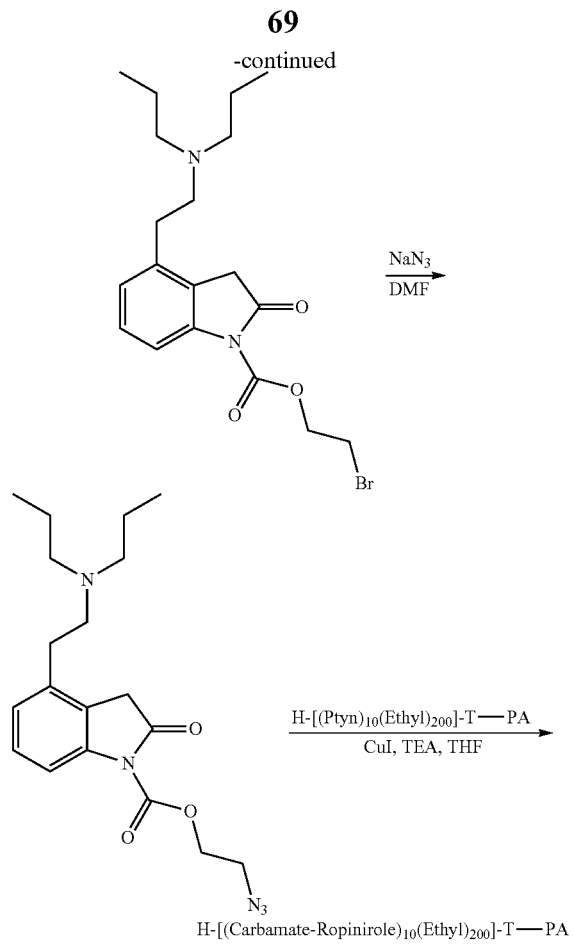

Bromoethyl-N-ropinirolylcarbamate:

To a solution of ropinirole hydrochloride (0.558 g, 1.88 mmol) in Dioxane (38 ml) was added triethylamine (2.10 ml, 15.1 mmol). After stirring for 5 minutes, 2-bromoethyl chloroformate (1.61 ml, 15.1 mmol) was added slowly and the mixture was allowed to stir overnight at room temperature. Water (40 mL) was added to give a mixture with pH of 9.5. After stirring overnight, the mixture was stirred with dichloromethane (40 mL) and brine solution (10 mL) for 10 minutes. Two layers were separated and the top layer was extracted with dichloromethane (40 mL). The combined organic phases were dried over $Na_2SO_4$, filtered, and concentrated to give dark red colored thick oil. Further purification was performed by silica gel column chromatography eluting with dichloromethane/EtOAc (starting from 9:1, 4:1, and then 100% EtOAc) to give the desired N-acylated product, bromoethyl-N-ropinirolylcarbamate, as dark red colored oil (0.170 g, 22.01% yield).). $^1$H NMR (Varian, 500 MHz, 10 mg/mL DMSO-d6, δ): 0.83 (t, J=7.5 Hz, 6H, —$CH_2CH_2CH_3$), 1.39 (m, 4H, —$CH_2CH_2CH_3$), 2.39 (t, J=7.5 Hz, 4H, —$CH_2CH_2CH_3$), 2.62 (m, 4H, $Pr_2NCH_2CH_2$—Ar), 3.80 (s, 2H, —$CH_2C$(=O)—), 3.80 (t, J=5.5 Hz, 2H, —$OCH_2CH_2Br$), 4.65 (t, 2H, —$OCH_2CH_2Br$), 7.04 (d, J=8.0 Hz, 1H, Ar H), 7.25 (t, J=8.0 Hz, 1H, Ar H), 7.63 (d, J=8.0 Hz, 1H, Ar H). Azidoethyl-N-ropinirolylcarbamate: To a solution of bromoethyl-N-ropinirolylcarbamate (0.170 g, 0.414 mmol) in DMF (2 ml) was added sodium azide (0.027 g, 0.414 mmol) to give a clear yellow solution. After stirring overnight at room temperature, the mixture was quenched with 1 mL of 0.1N HCl and then diluted with 2 mL of water. All the volatiles were removed using a rotary evaporator and the aqueous solution was extracted twice with dichloromethane (3 mL each). The combined organic phases were dried over $Na_2SO_4$, filtered, and concentrated to give azidoethyl-N-ropinirolylcarbamate (0.12 g, 78% yield) as thick yellow oil. $^1$H NMR (Varian, 500 MHz, 10 mg/mL DMSO-$d_6$, δ): 0.93 (t, J=Hz, 6H, —$CH_2CH_2CH_3$), 1.70 (m, 4H, —$CH_2CH_2CH_3$), 2.99 (m, J=Hz, 4H, $Pr_2NCH_2CH_2$—Ar), 3.07 (m, 4H, —$CH_2CH_2CH_3$), 3.22 (m, 4H, $Pr_2NCH_2CH_2$—Ar), 3.92 (s, 2H, —$CH_2C$(=O)—), 3.98 (t, 2H, —$OCH_2CH_2N_3$), 4.48 (t, 2H, —$OCH_2CH_2Br$), 7.14 (d, J=7.5 Hz, 1H, Ar H), 7.33 (t, J=8.0 Hz, 1H, Ar H), 7.69 (d, J=8.0 Hz, 1H, Ar H).

H-[(Carbamate-Ropinirole)$_{10}$(EOZ)$_{190}$]—COOH 20K:

Azidoethyl-N-ropinirolylcarbamate hydrochloride (0.12 g, 0.293 mmol) was dissolved in THF (15 ml). H-[(Ptyn)$_{10}$(Ethyl)$_{200}$]-T-PA (0.488 g, 0.024 mmol) was added and the mixture was stirred to dissolve completely. CuI (0.019 g, 0.098 mmol) and triethylamine (0.014 ml, 0.098 mmol) were added to give a clear red solution.

After stirring for 16 hours at 45° C., the mixture was quenched with 2 mL of 0.1 N HCl to give a solution with pH of 3. All the volatiles were removed and the residue was redissolved in methanol. The resulting mixture was passed through Dowex and amberlite IR-120 column using methanol as an eluent. After removing methanol, the resulting aqueous solution was extracted twice with dichloromethane (5 mL each). The organic solution was dried over $Na_2SO_4$, filtered, concentrated down to 10 mL, and precipitated by adding into 70 mL of diethyl ether. The precipitate was filtered and dried in vacuo to give H-[(Carbamate-Ropinirole)$_{10}$(Ethyl)$_{200}$]-T-PA (0.50 g, 86% yield) as, a pale yellow powder. In addition to the usual polymer backbone peaks, $^1$H NMR (Varian, 500 MHz, 10 mg/mL DMSO-$d_6$, δ) shows the polymer chain contained an average of 6.4 units of rotigotine with major ropinirole peaks at 0.97 (m, 6H, —$CH_2CH_2CH_3$), 4.62 (m, 2H, —$OCH_2CH_2Br$ and m, 2H, —$OCH_2CH_2$-triazole ring), 7.19-7.39 (br m, 3H, Ar H), and 7.91 (m, 1H, triazole H).

Example 23—Synthesis of Polyethylene Glycol Dendrimer (26K)

The syntheses of the PEG dendrimer has two steps, first the building of the PEG dendron blocks and second the convergence of the blocks to create the dendrimer structure.

i. Preparation of Dendron Building Block:

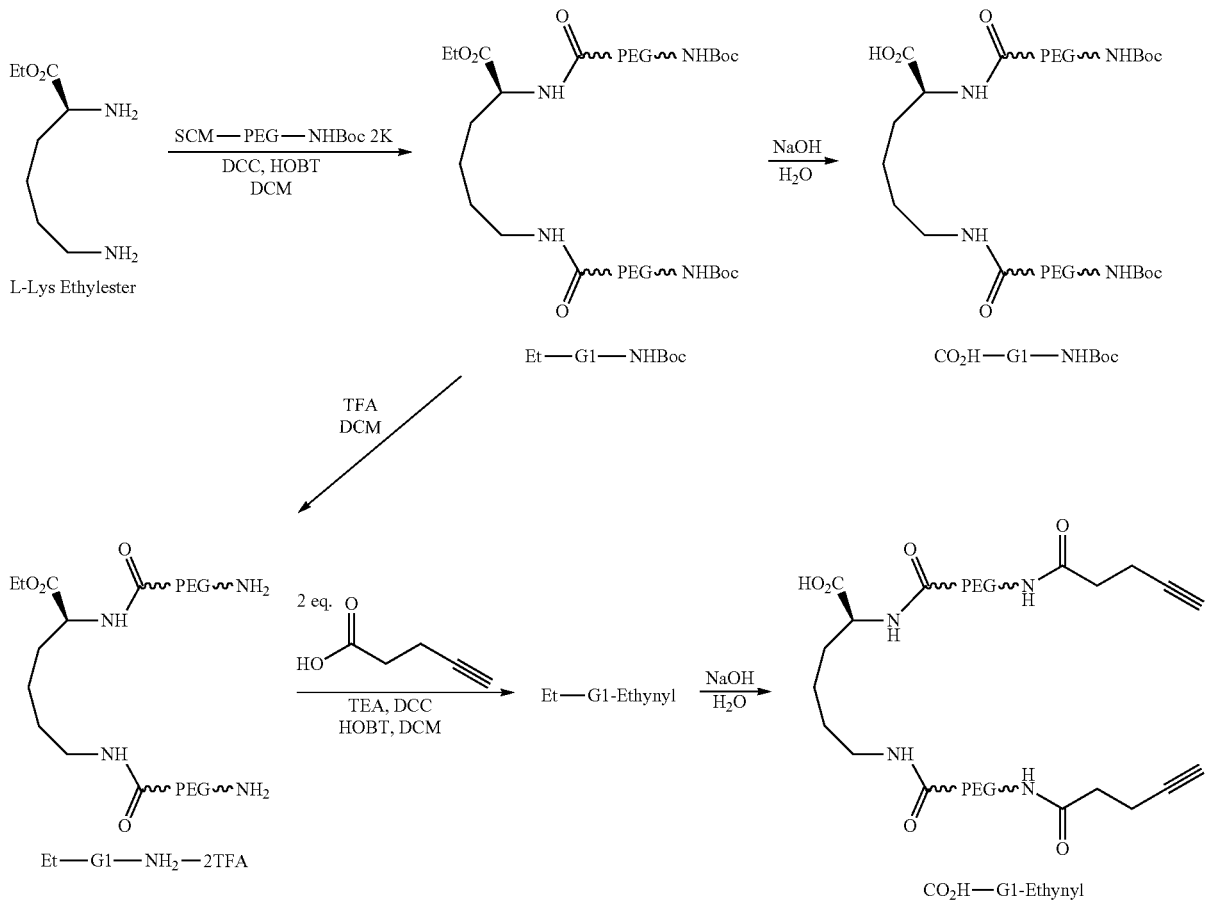

Et-G1-NHBoc.

L-lysine ethyl ester dihydrochloride (0.253 g, 1.025 mmol) and SCM-PEG-NHBoc 2K (4.71 g, 2.36 mmol) were dissolve in dichloromethane (170 ml). After addition of TEA (0.714 ml, 5.12 mmol), the mixture was stirred overnight at room temperature. The reaction mixture was quenched with 51 mL of 0.1N HCl solution and stirred with of NaCl (5.1 g).

Two layers were separated and the aqueous phase was extracted with dichloromethane (50 mL). The combined organic phases were dried over $Na_2SO_4$, filtered, concentrated using a rotary evaporator, and dried in vacuo give a crude as a waxy solid. The crude was redissolved in water and passed through an Amberlite column and then an ion-exchange column using both DEAE Sepharose FF and SP Sepharose FF. The resulting aqueous solution was charged with NaCl (15% w/v) and extracted with dichloromethane. The combined organic phases were dried over anhydrous $Na_2SO_4$, filtered, concentrated using a rotary evaporator, and dried in vacuo to provide Et-G1-NHBoc (3.4 g, 84% yield). $^1$H NMR (Varian, 500 MHz, 10 mg/mL $CDCl_3$) showed the usual backbone peak at 3.64 ppm (m, 4H, —$(OCH_2CH_2)_n$—) and other major peaks at 1.28 ppm (t, 3H, —$OCH_2CH_3$), 1.44 ppm (s, 18H, —NHBoc), 4.01 ppm (m, 4H two protons for each PEG, —NHC(=O)$CH_2$— ($OCH_2CH_2)_n$—), 4.32 ppm (q, 2H, —$OCH_2CH_3$), 4.59 ppm (q, 1H, —CH($CO_2$EONH—).

$CO_2$H-G1-NHBoc.

Et-G1-NHBoc (0.975 g, 0.247 mmol) was dissolved in water (6.2 ml) and stirred overnight with 0.1 N NaOH (5 ml, 0.5 mmol). The mixture was acidified by adding 0.5 mL of 1N HCl, charged with 1.8 g of NaCl (15% w/v), and then stirred with 10 mL of DCM. The two layers were separated and the aqueous phase was extracted with 8 mL of DCM. The combined organic phases were dried over $Na_2SO_4$, filtered, concentrated, and dried in vacuo to give $CO_2$H-G1-NHBoc (0.928 g, 96% yield) as a pale yellow waxy powder. The completion of the hydrolysis was confirmed by $^1$H NMR (Varian, 500 MHz, 10 mg/mL $CDCl_3$) revealed the disappearance of ester proton peaks, shown at 1.28 and 4.32 ppm (—$OCH_2CH_3$)

Et-G1-$NH_2$.2TFA.

Et-G1-NHBoc (2.42 g, 0.613 mmol) was dissolved in dichloromethane (15.33 ml) and stirred with TFA (2.36 ml, 30.7 mmol) for 1 hour at room temperature. Most of the volatiles were removed using a rotary evaporator to give ~4.5 g of thick red extract. The crude was stirred with 30 mL of diethyl ether to give a sticky powdery material and slightly cloudy solution. After decanting the solution, the residue was stirred with 30 mL of diethyl ether. After decanting the solution, the pale white powder (waxy) was dried over night in vacuo. The crude was redissolved in 25 mL of dichloromethane and then washed with brine (20 mL), dried over $Na_2SO_4$, filtered, concentrated using a rotary evaporator, and dried in vacuo to give Et-G1-$NH_2$·2TFA (2.10 g, 86% yield). The completion of the deprotection was confirmed by the disappearance of -Boc group proton peak, shown at 1.44 ppm (s, 18H, —NHBoc).

$CO_2H$-G1-Ethynyl.

HOBT (0.209 g, 1.362 mmol) was dried by azeotrope using acetonitrile. To the residue was added a solution of 4-pentynoic acid (0.125 g, 1.277 mmol) in dichloromethane (20 ml). DCC (0.264 g, 1.277 mmol) was added and the mixture was stirred for 10 minutes to give a cloudy solution. A solution of Et-G1-$NH_2$·2TFA (1.69 g, 0.426 mmol) with TEA (0.356 ml, 2.55 mmol) in dichloromethane (20 ml) was added. After stirring for 18 hours, the reaction mixture was filtered using a syringe filter and quenched with 0.1N HCl. All the organic volatiles were removed using a rotary evaporator and passed through an Amberlite column and then an ion-exchange column using DEAE Sepharose FF. The resulting aqueous solution was charged with NaCl (15% w/v) and extracted with dichloromethane. The organic phase was dried over anhydrous $Na_2SO_4$, filtered, concentrated using a rotary evaporator, and dried in vacuo to provide Et-G1-Ethynyl.

Hydrolysis of Et-G1-Ethynyl.

The ethyl ester product was dissolved in water and pH of the solution was adjusted to 13 using 0.5 N NaOH. After stirring overnight, the mixture was acidified to pH of 3 and purified by an Amberlite column and an ion-exchange column using DEAE Sepharose FF to give 1.14 g (69% yield) of $CO_2H$-G1-Ethynyl as the desired product. $^1H$ NMR (Varian, 500 MHz, 10 mg/mL $CDCl_3$) showed the usual backbone peak at 3.64 ppm (m, 4H, —$(OCH_2CH_2)_n$—) and other major peaks at 2.03 (m, 2H, —$CH_2CH_2CCH$), 2.42 (t, 4H, —$CH_2CH_2CCH$), 2.53 (t, 4H, —$CH_2CH_2CCH$), 3.98-4.16 ppm (m, 4H two protons for each PEG, —NHC(=O)$CH_2$—$(OCH_2CH_2)_n$—), 4.62 ppm (q, 1H, —$CH(CO_2Et)$NH—).

ii. Construction of Dendrimer via Convergent Pathway

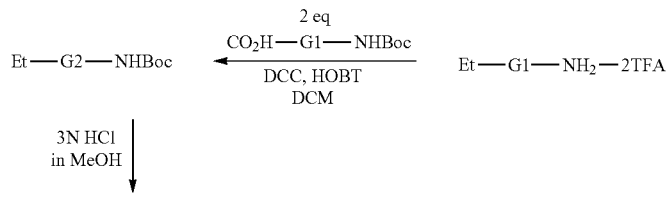

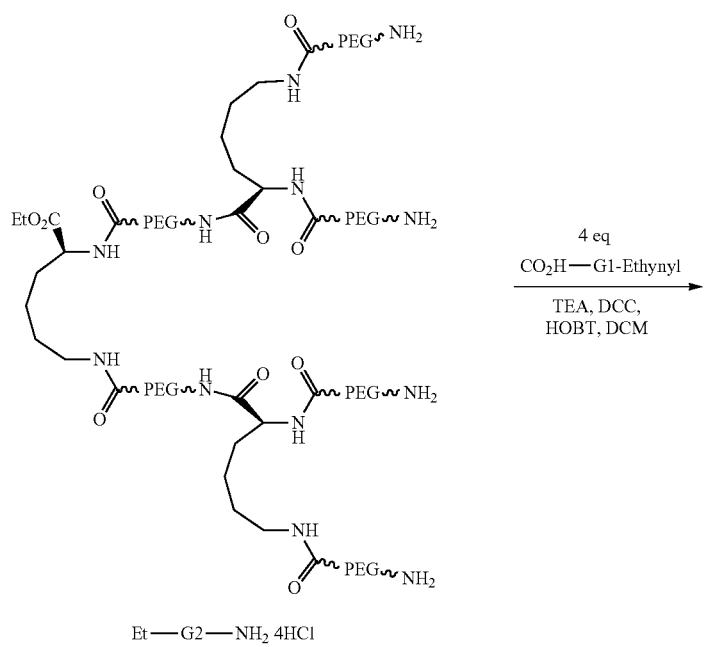

-continued

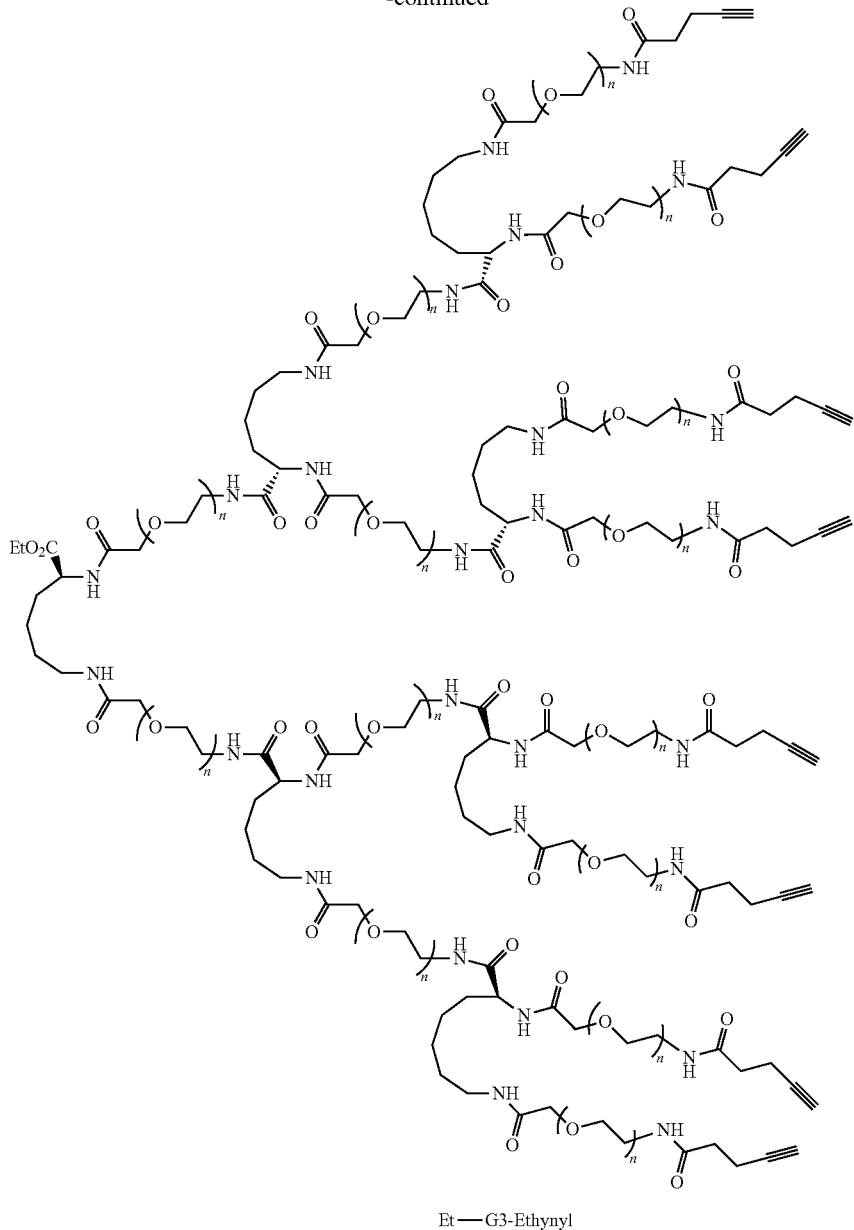

Et—G3-Ethynyl

Et-G2-NHBoc.

HOBT (0.035 g, 0.227 mmol) was dried by azeotrope using acetonitrile (20 mL). To the residue was added a solution of $CO_2H$-G1-NHBoc (0.890 g, 0.227 mmol) in dichloromethane (15 ml). DCC (0.047 g, 0.227 mmol) was added and the mixture was stirred for 3 hours. After addition of Et-G1-$NH_2$.2TFA (0.410 g, 0.103 mmol) and TEA (0.086 ml, 0.620 mmol), the reaction mixture was stirred overnight at room temperature. The mixture was filtered using a syringe filter and quenched with 0.1N HCl. All the organic volatiles were removed using a rotary evaporator. The resulting aqueous solution was passed through an Amberlite column and then an ion-exchange column using both DEAE Sepharose FF and SP Sepharose FF. The resulting aqueous solution was charged with NaCl (15% w/v) and extracted with dichloromethane. The combined organic phases were dried over anhydrous $Na_2SO_4$, filtered, concentrated using a rotary evaporator, and dried in vacuo to provide Et-G2-NHBoc (0.879 g, 74% yield). Ion-exchange analysis on both DEAE and SP column revealed all neutral species. $^1$H NMR (Varian, 500 MHz, 10 mg/mL $CDCl_3$) showed the usual backbone peak at 3.64 ppm (m, 4H, —$(OCH_2CH_2)_n$—) and other major peaks at 1.28 ppm (m, 3H, —$OCH_2CH_3$), 1.44 ppm (s, 36H, —NHBoc), 3.98-4.04 ppm (m, 12H two protons for each PEG, —NHC(=O)$CH_2$—(OCH$_2$CH$_2$)$_n$—), 4.19 ppm (m, 2H, —$OCH_2CH_3$), 4.59 ppm (q, 1H, —CH($CO_2$Et)NH—).

Et-G2-$NH_2$.4HCl.

Et-G2-NHBoc (0.877 g, 0.076 mmol) was stirred with 20 mL of Methanolic HCl (5 ml, 15.20 mmol) for 1 hour at room temperature. All the volatiles were removed by rotavap. The residue was redissolved in 30 mL of dichloromethane and washed with 25 mL of brine solution. The organic solution was dried over $Na_2SO_4$, filtered, concentrated, and dried in vacuo to give Et-G2-NH$_2$·HCl (0.883 g, quantitative yield). $^1$H NMR (Varian, 500 MHz, 10 mg/mL CDCl$_3$) showed the usual backbone peak at 3.64 ppm (m, 4H, —(OCH$_2$CH$_2$)$_n$—) and other major peaks at 1.28 ppm (m, 3H, —OCH$_2$CH$_3$), 3.94-4.04 ppm (m, 12H two protons for each PEG, —NHC(=O)CH$_2$—(OCH$_2$CH$_2$)$_n$—), 4.17 ppm (m, 2H, —OCH$_2$CH$_3$). The completion of the deprotection was confirmed by the disappearance of -Boc group proton peak, shown at 1.44 ppm (s, 36H, —NHBoc).

Et-G3-Ethynyl.

HOBT (0.051 g, 0.332 mmol) was dried by azeotrope using 30 mL of acetonitrile. To the residue was added a solution of CO$_2$H-G1-Ethynyl (1.133 g, 0.292 mmol) in dichloromethane (33 ml). DCC (0.060 g, 0.292 mmol) was added and the mixture was stirred for 2 hours at room temperature to give a cloudy solution. After addition of Et-G2-NH2 HCl (0.75 g, 0.066 mmol) and TEA (0.074 ml, 0.532 mmol), the mixture was stirred for 16 hours at room temperature. The mixture was quenched with 6 mL of 0.1 N HCl. All the organic volatiles were removed using a rotary evaporator and the remaining aqueous solution was diluted with 15 mL of water. The resulting aqueous solution was passed through an Amberlite column and then an ion-exchange column using both DEAE Sepharose FF and SP Sepharose FF to remove excess acid dendron species and amino species due to the incompletion of the reaction. The resulting aqueous solution was charged with NaCl (15% w/v) and extracted with dichloromethane. The combined organic phases were dried over anhydrous Na$_2$SO$_4$, filtered, concentrated using a rotary evaporator, and dried in vacuo to provide pale yellow solids. Further purification was performed by stirring with 30 mL of diethyl ether for 30 minutes, filtering on a glass frit, and drying to give Et-G3-Ethynyl (1.221 g, 69% yield) as pale yellow crystalline. Ion-exchange analysis on both DEAE and SP column revealed all neutral species. $^1$H NMR (Varian, 500 MHz, 10 mg/mL CDCl$_3$) showed the usual backbone peak at 3.64 ppm (m, 4H, —(OCH$_2$CH$_2$)$_n$—) and other major peaks at 1.28 ppm (m, 3H, —OCH$_2$CH$_3$), 2.03 (m, 2H, —CH$_2$CH$_2$CCH), 2.43 (t, 16H, —CH$_2$CH$_2$CCH), 2.53 (t, 16H, —CH$_2$CH$_2$CCH), 3.98-4.03 ppm (m, 28H two protons for each PEG, —NHC(=O)CH$_2$—(OCH$_2$CH$_2$)$_n$—), 4.17 ppm (m, 2H, —OCH$_2$CH$_3$), 4.40 ppm (q, 6H, —CH(CO—)NH—). 4.62 ppm (q, 1H, —CH(CO$_2$Et)-NH—).

Example 24—PEG Et-G3-Ethynyl Dendrimer 26K Attached to Rotigotine 3-azidopropionate

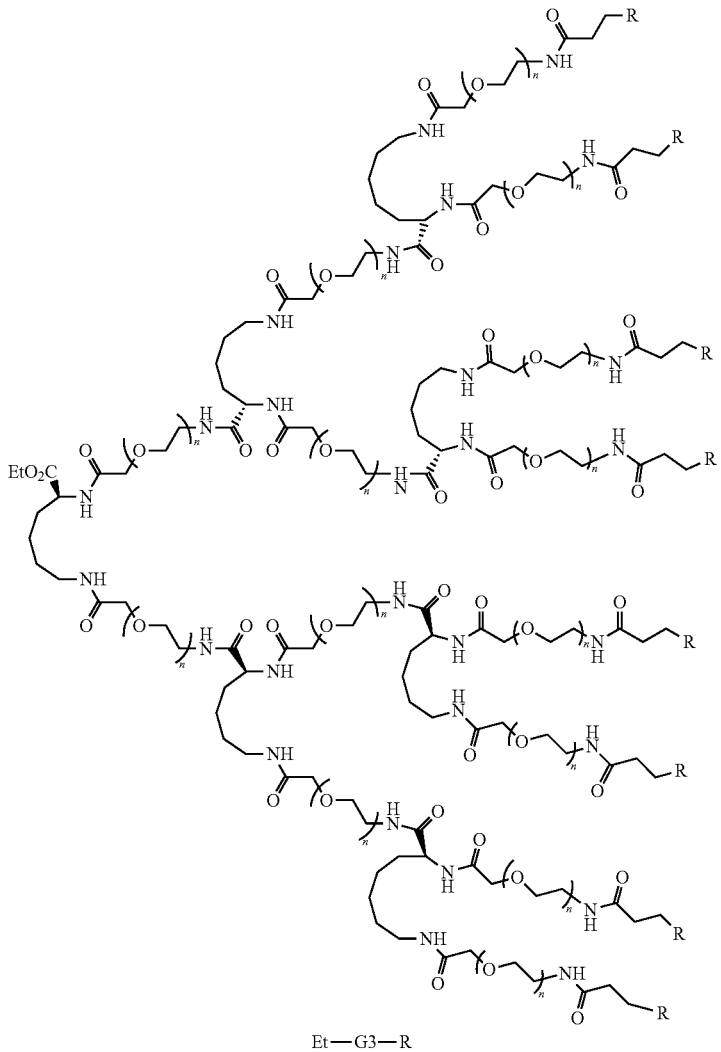

Et—G3—R

-continued

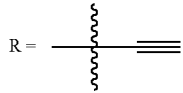

Et—G3-Ethynyl

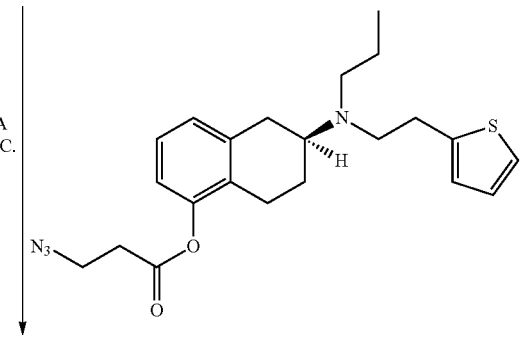

CuI, TEA
THF, 50° C.

Et—G3—Pr-Rotig

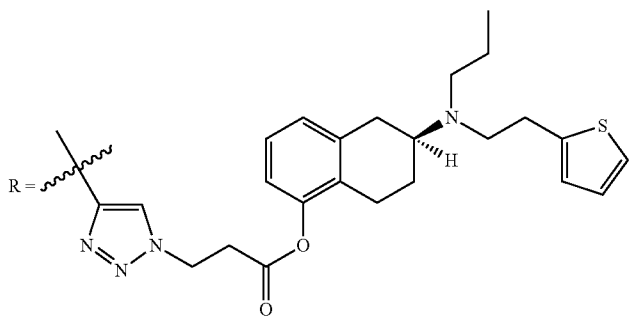

Rotigotine 3-azido propionate (0.192 g, 0.365 mmol) and Et-G3-Ethynyl (1.077 g, 0.041 mmol) were dissolved in THF (27.0 ml). triethylamine (0.090 ml, 0.648 mmol) and CuI (0.123 g, 0.648 mmol) were added and the mixture was stirred for 40 hours at 50° C. After cooling down to room temperature, the mixture was stirred with 12 mL of 0.1N HCl solution. After removing THF using a rotary evaporator, the resulting aqueous solution was diluted with 10 mL of water and passed through Amberlite (IR-120H) column (50 mL) and Dowex® M4195 column (50 mL) using 0.01% HCl solution as an eluent. The collected aqueous solution was stirred with 70 mL of dichloromethane using 22 g of NaCl (15 w/v % of water amount). Two layers were separated and the aqueous phase was stirred with 70 mL dichloromethane. The combined organic phases were dried over $Na_2SO_4$, filtered, concentrated, precipitated by adding into diethyl ether, filtered, and dried in vacuo. The resulting waxy solid was stirred with diethyl ether (20 mL) for 1 hour, filtered, and dried to give 0.997 g (82% yield) of the desired product, Et-G3-Rotig HCl, as pale yellow powder. $^1$H NMR (Varian, 500 MHz, 10 mg/mL $CDCl_3$) showed the usual PEG peak at 3.64 ppm (m, 4H, —$(OCH_2CH_2)_n$—) and other major peaks at 1.28 ppm (m, 3H, —$OCH_2CH_3$), 3.97-4.03 ppm (m, 28H two protons for each PEG, —NHC(=O)$CH_2$—($OCH_2CH_2)_n$—), 4.17 ppm (m, 2H, —$OCH_2CH_3$), 4.41 ppm (q, 6H, —CH(CO)NH—), and 4.62 ppm (q, 1H, —CH($CO_2$Et)NH—). Rotigotinyl peaks revealed at 1.04 ppm (t, 3H, —$CH_2CH_2CH_3$), 4.73 ppm (m, 2H, triazole-$CH_2CH_2$C(=O)ORotig), 6.89-7.20 ppm (m, 6H, aromatic and thiophenyl H), 7.70 (br s, 1H, triazole H). Number of rotigotine molecules on the dendrimer was determined as 5.6 by both $^1$H NMR and reverse phase HPLC analysis. 'Click' reaction was monitored by the disappearance of the termini peaks showed at 2.03 (m, 2H, —$CH_2CH_2$CCH) and 2.43 (t, 16H, —$CH_2CH_2$CCH), and by the appearance of triazole proton peak at 7.70 ppm.

Example 25—Synthesis of mPEG-co-polyamido G2 Ethynyl Dendrimer (20K)
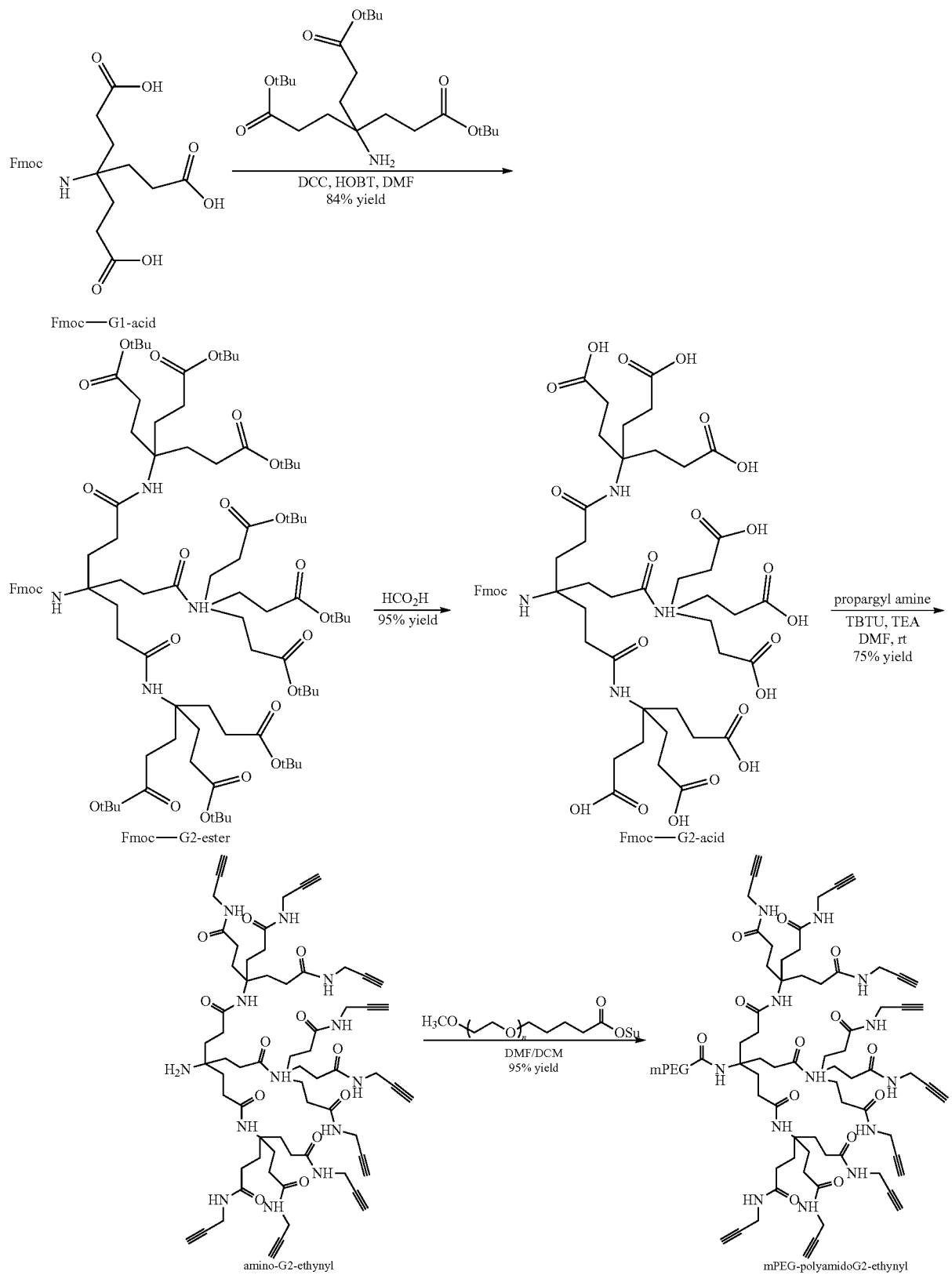

Fmoc-G2-ester:

A 25 mL of round bottom flask was charged with 1-HOBT hydrate (0.342 g, 2.24 mmol), dried by azeotrope using 15 mL of acetonitrile. After adding DMF (8 ml), Fmoc-G1-acid (0.3 g, 0.639 mmol) and DCC (0.461 g, 2.24 mmol) were added. After stirring for 1 h 30 minutes, the mixture became cloudy and amino-G1-ester (0.929 g, 2.24 mmol) was added. The resulting pale yellow precipitated solution was allowed to stir for 16 hours at room temperature. The mixture was filtered and the filtrate was concentrated in vacuo. The residue was dissolved in dichloromethane (20 mL) and washed with a saturated aqueous solution of NaHCO$_3$ twice (10 mL each) and then with brine. The organic phase was dried over Na$_2$SO$_4$, filtered, and concentrated using a rotary evaporator. The crude was purified by silica gel column chromatography eluting with a solvent mixture of EtOAc/hexanes (2:3 and then 1:1) to give 0.89 g of the desired product Fmoc-G2-ester in 84% yield. $^1$H NMR (Varian, 500 MHz, 10 mg/mL CDCl$_3$, δ): 1.41 (s, 81H, —COOC(CH$_3$)$_3$), 1.96 (m, 24H, —NHC(CH$_2$CH$_2$CO—)$_3$), 2.20 (m, 24H, —NHC(CH$_2$CH$_2$CO—)$_3$), 4.20 (t, J=6.5 Hz, 1H, CHCH$_2$OC(=O)NH—), 4.30 (d, J=6.5 Hz, 2H, CHCH$_2$OC(=O)NH—), 6.03 (br s, 3H, —CH$_2$C(=O)NH—), 6.48 (br s, 1H, —CH$_2$OC(=O)NH—), 7.32 (t, J=7.5 Hz, 2H, Ar H), 7.39 (t, J=7.5 Hz, 2H, Ar H), 7.66 (d, J=7.5 Hz, 2H, Ar H), 7.76 (d, J=7.5 Hz, 2H, Ar H).

Fmoc-G2-acid:

Fmoc-G2-ester (0.89 g, 0.535 mmol) was dissolved in HCOOH (5.4 ml). After stirring for 16 hours, all the volatiles were removed using a rotary evaporator to give a thick oily material. The residue was stirred with diethyl ether, filtered, and dried to give a white powder (0.587 g, 95% yield). $^1$H NMR (Varian, 500 MHz, 10 mg/mL CD$_3$OD, δ): 1.91 (m, 24H, —NHC(CH$_2$CH$_2$CO—)$_3$), 2.28 (m, 24H, —NHC(CH$_2$CH$_2$CO—)$_3$), 4.23 (t, J=6.5 Hz, 1H, CHCH$_2$OC(=O)NH—), 4.36 (d, J=6.5 Hz, 2H, CHCH$_2$OC(=O)NH—), 6.84 (br s, 1H, —CH$_2$OC(=O)NH—), 7.33 (t, J=7.0 Hz, 2H, Ar H), 7.40 (t, J=7.0 Hz, 2H, Ar H), 7.70 (d, J=7.0 Hz, 2H, Ar H), 7.80 (d, J=7.0 Hz, 2H, Ar H). The completion of hydrolysis was confirmed by the disappearance of tert-butyl group peak showing at 1.41 ppm.

amino-G2-ethynyl:

Propargyl amine (0.415 g, 7.54 mmol), clear yellow oil, was weighed in a 100 mL round bottom flask and then diluted with DMF (38 ml). Fmoc-G2-ester (0.436 g, 0.377 mmol) was added to give a crowded solution. TBTU (1.45 g, 4.52 mmol) was added to give a clear yellow solution. After addition of TEA (1.26 ml, 9.05 mmol), the reaction mixture was allowed to stir for 4 days at room temperature. All the volatiles were removed in vacuo and the residue was stirred with 40 mL of dichloromethane to give a cloudy solution. The resulting mixture was stirred with brine solution (25 mL) resulting in two layers separation with a yellow sticky precipitate. Both organic and aqueous solutions were decanted and the residual yellow sticky material was dissolved in methanol. The recovered solution in methanol was concentrated and dried in vacuo to give 0.358 g of the desired amino-G2-ethynyl as pale yellow powder in 75% yield. $^1$H NMR (Varian, 500 MHz, 10 mg/mL CD$_3$OD, δ): 1.70 (br t, 6H, NH$_2$C(CH$_2$CH$_2$CO—)$_3$), 2.00 (m, 18H, —NHC(CH$_2$CH$_2$CO—)'$_3$), 2.21 (m, 24H, —C(CH$_2$CH$_2$CO—)$_3$), 2.60 (s, 9H, —NHCH$_2$CCH), 3.96 (d, J=2.0 Hz, 2H, —NHCH$_2$CCH). The completion of Fmoc group deprotection was confirmed by the disappearance of Fmoc group peaks.

mPEG-co-polyamido-G2-ethynyl.

mPEG-SVA 20K (0.429 g, 0.021 mmol) and amino-G2-ethynyl (0.0404 g, 0.032 mmol) were dissolved in 6 mL of 1:1 DMF/dichloromethane. After addition of TEA (0.012 ml, 0.085 mmol), the mixture was stirred for 18 hours at room temperature. All the volatiles were removed in vacuo at 40° C. and the residue was redissolved in 4 mL of DCM to give a milky solution. Upon the addition of IPA (12 mL), the solution became clear. Dichloromethane was removed using a rotavap to give a solution with white precipitates. After stirring for 10 minute at room temperature, the white precipitates were filtered, washed with IPA, and dried in vacuo to give 0.432 g (95% yield) of mPEG-polyamido-G2-ethynyl, block copolymer of PEG and polyamido dendrimer. $^1$H NMR (Varian, 500 MHz, 10 mg/mL CD$_3$OD, δ): 1.70 (m, 2H, mPEG-CH$_2$CH$_2$CH$_2$CH$_2$C(=O)—), 1.82 (m, 2H, mPEG-CH$_2$CH$_2$CH$_2$CH$_2$C(=O)—), 1.94 (br t, 6H, —NHC(CH$_2$CH$_2$CO—)$_3$), 2.01 (m, 18H, —NHC(CH$_2$CH$_2$CO—)$_3$), 2.21 (m, 18H, —C(CH$_2$CH$_2$CO—)$_3$), 2.38 (m, 6H, —C(CH$_2$CH$_2$CO—)$_3$), 2.62 (s, 9H, —NHCH$_2$CCH), 3.37 (s, 3H, CH$_3$O—), 3.64 (m, PEG backbone, CH$_3$O(CH$_2$CH$_2$O)$_n$CH$_2$—), 3.97 (br s, 2H, —NHCH$_2$CCH).

Example 26—PEG-Polyamido Dendrimer Attached to Rotigotine 3-azidopropionate

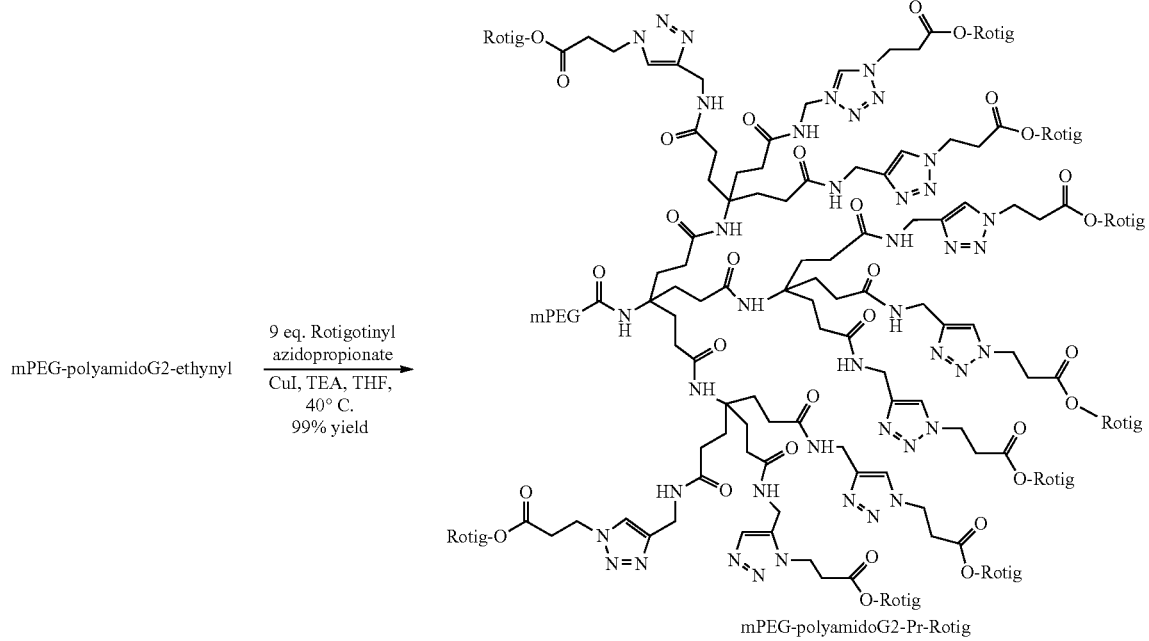

mPEG-polyamidoG2-ethynyl → 9 eq. Rotigotinyl azidopropionate / CuI, TEA, THF, 40° C. / 99% yield mPEG-polyamidoG2-Pr-Rotig Rotigotine 3-azidopropionate·HCl (0.085 g, 0.189 mmol) was dissolved in THF (12 ml). mPEG-polyamidoG2-ethynyl derndrimer (0.426 g, 0.020 mmol) was added and the mixture was stirred to dissolve completely. CuI (0.014 g, 0.072 mmol) and triethylamine (0.039 ml, 0.278 mmol) were added and the mixture was stirred for 16 hours at 45° C. After cooling down to room temperature, the mixture was quenched with 10 mL of 0.1N HCl solution. All the organic volatiles were removed using a rotary evaporator. The resulting aqueous solution was diluted with 10 mL of methanol and then passed through Dowex® M4195 column (15 mL) followed by methanol washing. After removing methanol using a rotary evaporator, the resulting aqueous solution was stirred with dichloromethane (20 mL each) twice using 1 g of NaCl. The combined organic phases were dried over $Na_2SO_4$, filtered, concentrated, and precipitated by adding into diethyl ether. The precipitated solution was filtered, and dried to give 0.47 g (quantitative yield) of the desired product, mPEG-polyamidoG2-Pr-Rotig, as a pale yellow crystalline material. Besides the copolymer backbone peaks, $^1$H NMR (Varian, 500 MHz, 10 mg/mL $CD_3OD$, δ) showed major rotigotinyl peaks, due to the completion of 'click' reactions, at 1.05 ppm (d, 27H, Rotigotinyl —$CH_2CH_2CH_3$), 4.40 ppm (m, 18H, —$N_{triazole}CH_2CH_2C(=O)$O-Rotig), 4.70 ppm (m, 18H, —C(=O)NHCH$_2$—C$_{triazole}$—), and 7.94 ppm (s, 9H, triazole H).

Example 27—Synthesis of Oxidized Polydextran (20K)

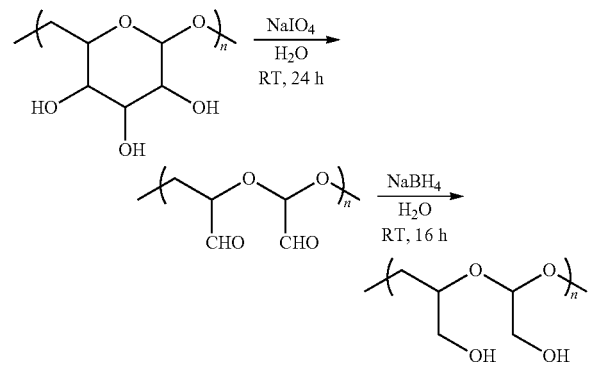

Polyal (Oxidized Dextran) Synthesis:

5.58 g of sodium periodate (26 mmole) was dissolved in 30 mL of DI-$H_2O$ in a 100 mL one-neck round-bottom flask. The flask was covered with aluminum foil. In a 20 mL vial, 2.0 g of dextran (0.13 mmole, $M_n$: 15,340 g/mole, $M_p$: 22,630 g/mole, PD: 2.11) was dissolved in 15 mL of DI-$H_2O$ and this solution was slowly added into the round-bottom flask. The vial was rinsed with 15 mL of DI-$H_2O$ and the rinse solution was also added into the round-bottom flask. The clear colorless solution was stirred at room temperature for 24 h. At the end of this time, the aqueous solution was transferred into two Slide-A-Lyzer 2K dialysis cassettes and dialysis was conducted in water overnight. This aqueous solution (~60 mL) was used in the next step.

Polyalcohol Synthesis from Polyal:

1.134 g of sodium borohydride (30 mmole) was dissolved in 10 mL of DI-$H_2O$ in a 100 mL one-neck round-bottom flask. The aqueous solution from the previous step (BD-29-8) was then added slowly into the round-bottom flask. The solution was stirred for 18 h. The pH of the solution was adjusted to 6 using 3M HCl and the solution was again dialyzed using three 10K MWCO dialysis cassettes and for two days. The aqueous solution was concentrated down to 5 mL and then lyophilized for two days to give 1.56 g of the polyalcohol in 94% yield.

$^1$H NMR (DMSO-d6, δ, ppm, TMS): 3.35 (2H, —OCH$_2$CH(CH$_2$OH)O—), 3.48 (2H, —OCH(CH$_2$OH)O—), 3.58-3.70 (2H, —OCH$_2$CH(CH$_2$OH)O—), 3.64 (1H, —OCH$_2$CH(CH$_2$OH)O—), 4.62 (2H, —OCH$_2$CH(CH$_2$OH)OCH(CH$_2$OH)O—), 4.70 (1H, —OCH(CH$_2$OH)O—). $^{13}$C NMR (DMSO-d6, δ, ppm, TMS): 64.56 (—OCH$_2$CH(CH$_2$OH)O—), 65.10 (—OCH(CH$_2$OH)O—), 68.96 (—OCH$_2$CH(CH$_2$OH)O—), 79.88 (—OCH$_2$CH(CH$_2$OH)O—), 105.86 (—OCH(CH$_2$OH)O—). GFC: $M_n$: 11,100 g/mole, $M_p$: 19,270 g/mole, PD: 2.41

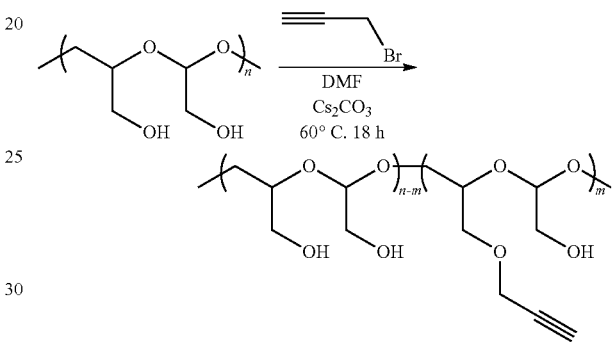

Polyalcohol Propargyl Bromide Reaction:

840.0 mg of polyalcohol (5×10$^{-5}$ mole, $M_n$: 11,100 g/mole, $M_p$: 19,270, PD: 2.4) was dissolved in 10 mL of dimethylformamide in a 25 mL round-bottom flask. 5 mL of toluene was then added into the round-bottom flask. Toluene was rotovapped down at 50° C. at 40 mbar using a rotary evaporator. 407.5 mg of cesium carbonate (1.25×10$^{-3}$ mole) was then added into the round-bottom flask. The mixture was stirred for 3 h under Argon at 60° C. 234.0 mg of propargyl bromide solution (80% solution in toluene, 187.5 mg of propargyl bromide, 1.25×10$^{-3}$ mole) was added into the round-bottom flask. The cloudy solution was stirred at 60° C. for 34 h under Argon. At the end of this time, the yellow cloudy solution was cooled down to room temperature, filtered through a 30 mL frit, and the filtrate was concentrated down to dryness. The polymer was redissolved in 15 mL of DI-$H_2O$ and washed with dichloromethane twice (2×45 mL). The dichloromethane phase was washed with 15 mL of DI-$H_2O$. Aqueous phases were separated, combined and rotovapped down to remove any residual dichloromethane. The aqueous solution was then dialyzed using a 2K MWCO dialysis cassette overnight. The water was removed and the polymer was dried under high vacuum to give 730.0 mg of the final product.

$^1$H NMR (DMSO-d6, δ, ppm, TMS): 3.35 (2H, —OCH$_2$CH(CH$_2$OH)O—), 3.48 (2H, —OCH(CH$_2$OH)O—), 3.58-3.70 (2H, —OCH$_2$CH(CH$_2$OH)O—), 3.64 (1H, —OCH$_2$CH(CH$_2$OH)O—), 4.18 (4H, —OCH$_2$CH(CH$_2$OCH$_2$C≡CH)OCH(CH$_2$OCH$_2$CCH)O—), 4.62 (2H, —OCH$_2$CH(CH$_2$OH)OCH(CH$_2$OH)O—), 4.70 (1H, —OCH(CH$_2$OH)O—). From NMR data, the average value of 'n' is 78 and of 'm' is 5.

Example 28—Oxidized Polydextran (20K) Attachment to 3-azidopropyl Rotigotine

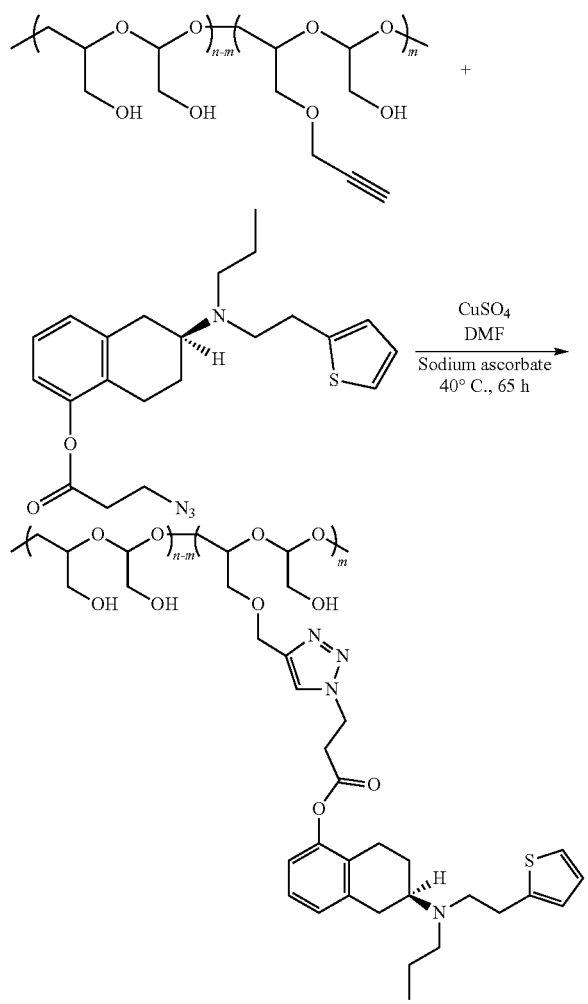

Three hundred and forty two milligrams (342.0 mg) of 3-azidopropionyl rotigotine.TFA ($6.5 \times 10^{-4}$ mole) was weighed in a 100 mL round-bottom flask and 835.0 mg of oxidized dextran with acetylene pendents ($6.5 \times 10^{-5}$ mole; average 'n' value of 89, 'm' value of 6) and was added into the flask. Eighty milliliters (80 mL) of dimethylformamide was then added into the flask to completely dissolve the polymer. 64.5 mg of copper sulfate ($2.6 \times 10^4$ mole) and 103.0 mg of sodium ascorbate ($5.2 \times 10^{-4}$ mole) were then added into the round-bottom flask. The round-bottom flask was closed with a rubber septum and the solution was stirred at 40° C. under Argon overnight. More copper sulfate (258.0 mg, $1.04 \times 10^{-3}$ mole) and sodium ascorbate (412.0 mg, $2.08 \times 10^{-3}$ mole) were added into the RBF and the solution was stirred overnight at 40° C. More copper sulfate (322.5 mg, $1.3 \times 10^{-3}$ mole) and sodium ascorbate (515.0 mg, $2.6 \times 10^{-3}$ mole) were added into the RBF and the solution was stirred overnight at 40° C. At the end of this time; the solution was cooled down to room temperature, filtered through a coarse fit, and rotovapped down to dryness. The residue was redissolved in 60 mL of DMF, filtered, concentrated down to 10 mL and precipitated into diethyl ether (200 mL). The solvents were decanted and the polymer was dried under high vacuum overnight to give 362.0 mg of the final product. $^1$H NMR (DMSO-d6, δ, ppm, TMS): 0.86 (3H, —NCH$_2$CH$_2$CH$_3$); 1.4-3.6 (total of 17H, aliphatic CH and CH$_2$ peaks of rotigotine); 3.36 (2H, —OCH$_2$CH(CH$_2$OH)O—), 3.47 (2H, —OCH(CH$_2$OH)O—), 3.57-3.70 (2H, —OCH$_2$CH(CH$_2$OH)O—), 3.64 (1H, —OCH$_2$CH(CH$_2$OH)O, 4.62 (2H, —OCH$_2$CH(CH$_2$OH)OCH(CH$_2$OH)O—), 4.70 (1H, —OCH(CH$_2$OH)O—); 6.80-7.29 (6H, —CH peaks of 1,2,3,4-tetrahydronaphtalene and —CH peaks of 2-thiophene); 8.14 (1H, —CH peak of triazole).

Example 29—Hydrolysis of Active Drug Molecules (Rotigotine, Etoposide, Irinotecan, Tiagabine) from their Polymer Conjugated Forms The cleavage of rotigotine, etoposide, irinotecan and tiagabine from the different types of linkers attached to the backbones of polyoxazoline, polyethylene glycol, modified dextran and PEG dendrimer polymers was examined in rat plasma. Four milliliters of rat plasma was placed in a test tube, and then spiked with approximately 16 mg of each polymer drug conjugate dissolved in 400 µL of a 5% dextrose solution. The test tubes were placed in a 37° C. water bath and allowed to incubate for approximately 48-72 hours. At regular time intervals, a 100 µL aliquot of plasma was taken and placed in a 1.5 mL centrifuge tube, neutralized with 5 µL of dilute acid solution (3M HCl), and treated with approximately 500 µL of acetonitrile to precipitate the plasma proteins and dissolve the released drug. The tube was centrifuged at 14,000 rpm for 5 minutes. The supernatant was removed, diluted in 0.1% TFA in water, filtered, placed in a HPLC vial, and assayed by reverse phase chromatography using a Zorbax C8 300SB, 5µ, 4.6×150 mm column fixed to an Agilent 1100/1200 chromatogarphy system fitted with a variable UV detector set at a wavelength to accommodate for the λmax of each drug. The mobile phase was 0.1% TFA in water (A) and 0.1% TFA in acetonitrile (B) eluting a rate of 1 mL/min. A standard curve was created by spiking a known concentration of drug in plasma and extracting and assaying the free drug as described above. The amount of drug in each aliquot was calculated from the standard curve above and a plot of the concentration of drug released versus time was generated. The half-life of each polymer drug conjugate was calculated and reported in Tables 1-3.

TABLE 1

Effect of linker and polymer on rate of release of rotigotine from rotigotine esters (polymer-triazine-alkyl-CO—O-Rotigotine) in plasma, pH 7.4, 37° C.

| Polymer* | Alkyl Linker | % Drug Loading | Half-Life |
|---|---|---|---|
| POZ | —CH$_2$— | 14.2 | 2.4 ± 0.28 hours (for n = 2) |
| POZ | —CH$_2$(CH$_3$)— | 9.6 | 7.1 hours |
| POZ | —CH$_2$CH$_2$— | 13.0 | 11.9 ± 4.2 hours (for n = 6) |
| POZ | —CH$_2$CH$_2$CH$_2$— | 12.4 | 5.0 hours |
| PEG | —CH$_2$CH$_2$— | 5.2 | 8 minutes |
| PEG Dendrimer | —CH$_2$CH$_2$— | 5.4 | 11 minutes |
| Modified Dextran | —CH$_2$CH$_2$— | 2.3 | <2 minutes |

*POZ is MW 20,000, acid terminus, 10 triazine pendents. PEG is four arm, MW 20,000, four triazine terminae. See text for structures.

TABLE 2

Effect of drug on rate of release of drug from POZ-triazine-$CH_2$—CO—O-Drug in plasma, pH 7.4, 37° C.

| Drug | % Drug Loading | Half-Life (hours) |
|---|---|---|
| Etoposide | 18.2 | 3.9 |
| Irinotecan | 16.5 | 6.5 |
| Rotigotine | 13.7 | 2.4 |
| Tiagabine | 14.5 | 80.6 |

POZ is MW 20,000, acid terminus, 10 triazine pendents.

TABLE 3

Effect of molecular weight and number of pendents on cleavage rate of POZ-triazine-$CH_2$—CO—O-Irinotecan in 50 mM sodium phosphate, pH 7.4, 37° C.

| Pendents | MW | Half-Life (hours) |
|---|---|---|
| 10 | 20K | 8.6 |
| 20 | 20K | 8.3 |
| 20 | 30K | 9.4 |
| 20 | 40K | 7.6 |

The results shown in Table 1 demonstrate that the length of the linker influences the rate of release of the agent, in this case rotigotine, from the polyoxazoline conjugate. The results show that as the length or size of the azidoalkyl acid linker increases, the rate of release of rotigotine from the polyoxazoline conjugate decreases. Table 2 shows that the nature of the agent also impacts the rate of release of the agent from the polymer. Table 3 shows that the molecular weight and the number of pendants groups do not significantly affect the rate of release when of irinotecan from polyoxazoline. Taken together, the results show that the release of an agent from a polyoxazoline conjugate can be tuned to release desired amounts of the agent over time.

TABLE 4

Effect of linker and polymer on rate of release of tiagabine from tiagabine esters (Polymer-triazine-linker-O—CO-tiagabine) in plasma, pH 7.4, 37° C.

| Polymer* | Linker | % Drug Loading | Half-Life (days) |
|---|---|---|---|
| POZ | —$CH_2$—$CH_2$— | 14.7 | 4.6 |
| POZ | —$CH_2$—$CH_2CH_2$— | 13.8 | 3.8 |
| POZ | —$(CH_2CH_2O)_3$— | 14.2 | 2.8 |
| POZ | —$CH_2$—$CH_2$—CO—NH—$(C_6H_4)$— | 11.3 | 6.9 |
| PEG | —$CH_2$—$CH_2CH_2$— | 10.4 | 0.5 |

*POZ is MW 20,000, acid terminus, 10 triazine pendents. PEG is four arm, MW 10,000, four triazine terminae. See text for structures.

The release of tiagabine from a 20K polyoxazoline and 10K polyethylene glycol using three different types of linkers was also determined. The types of linkers tested were the alkyl linker, a polyethylene glycol linker and an aromatic amide linker for the polyoxazoline conjugates and the alkyl linker for the polyethylene glycol conjugate. Table 4 summarizes the drug loading % and approximate release half-lives (days). The results show that the more hydrophilic PEG polymer shows a faster drug release profile consistent with the results shown in Table 1.

While not being bound by any particular theory, it is hypothesized that the surprisingly slow hydrolysis rate of the compounds illustrated in Tables 1, 2 and 4 may result from the folding of the polymer to provide a water-poor environment for the bound drug and its associated releasable linker. In contrast, the relatively rapid hydrolysis of the POZ conjugate containing a ethylene oxide units as a linker may be explained by the assumption that the ethylene oxide units of the oligo(ethylene oxide) linker bring water into the neighborhood of the cleavable moiety. It is known from independent studies that there are 2-4 water molecules associated with each ethylene oxide unit of poly(ethylene oxide) (also known as PEG). In other words, the bound drug and its associated releasable linker reside in a water-rich environment rather than a water-poor environment as is the case in the other conjugates studied.

An alternative explanation is that one of the oxygen atoms of the ethylene oxide units could act to give a "neighboring group participation" effect. Neighboring group participation is a well-known theory to explain the ability of neighboring atoms to act as internal nucleophiles and speed up the cleavage of groups such as esters.

Example 30—Comparative Viscosity of Different Polymer Conjugates

The viscosity of each polymer drug conjugated sample was measured on a Brookfield LVDV-II Cone and Plate viscometer fitted with a temperature controlled jacketed plate. The polymer sample (0.5 mL of a 10, 20, 30 and 40% w/w solution in water) was placed on the center of the plate, which was attached to the main drive of the instrument. The cone (CPE-40) was rotated at different rates (rpm) and the viscosity (mPas) was recorded each time at 25° C. The table below shows a comparison of viscosity readings for each sample tested. The results show that POZ conjugates of the present disclosure have low viscosity that allow for ease of administration through a narrow bore needle.

TABLE 5

Viscosity of Polymer Conjugates of rotigotine, measured at 25° C.

| Polymer | Concentration | Drug Content | Viscosity (mPas) | Syringeability through 28G needle (150 g pressure) |
|---|---|---|---|---|
| POZ - Rotigotine 20K | 30% | 40 mg/mL | 64.8 | Yes |
| PEG - Rotigotine 10K | 52% | 50 mg/mL | 120.7 | Yes |
| PEG - Rotigotine 20K | 50% | 25 mg/mL | 217.5 | No |

TABLE 5-continued

Viscosity of Polymer Conjugates of rotigotine, measured at 25° C.

| Polymer | Concentration | Drug Content | Viscosity (mPas) | Syringeability through 28G needle (150 g pressure) |
|---|---|---|---|---|
| PEG Dendrimer - Rotigotine 20K | 50% | 27 mg/mL | 142.3 | Yes |
| Modified Dextran - Rotigotine 20K | 50% | 23 mg/mL | 160.0 | Yes |
| POZ - tiagabine 20K | 40% | 55.2 mg/mL | 200.6 | Yes |
| PEG - tiagabine 10K | 40% | 41.6 mg/mL | 73.0 | Yes |

Example 31—Pharmacokinetics of Rotigotine in Rat After Intravenous and Subcutaneous Administration of H-[(Acetyl-Rotigotine)$_{10}$(EOZ)$_{190}$]—COOH 20K and H-[(Propionyl-Rotigotine)$_{10}$(EOZ)$_{190}$]—COOH 20K In order to study the pharmacokinetics of the POZ conjugates described herein, in vivo studies were conducted with male Sprague-Dawley rats. Twenty-seven male cannulated Sprague-Dawley rats (300-350 g) were divided into nine groups of 3 animals per group. Groups I-II received a single subcutaneous (SC) dose (right flank) of POZ acetyl rotigotine (as described in Example 6) at equivalent doses of 1.6 and 6.4 mg/kg. Groups III-IV received a single subcutaneous (SC) dose (right flank) of POZ propyl rotigotine (as described in Example 7) at equivalent doses of 1.6 and 6.4 mg/kg. Group V received a single subcutaneous (SC) dose (right flank) of rotigotine hydrochloride at an equivalent dose of 0.5 mg/kg. Groups VI-VII received a single intravenous (IV) dose (lateral tail vein) of POZ acetyl rotigotine (as described in Example 6) at equivalent doses of 0.5 and 2.0 mg/kg. Groups VIII-IX received a single intravenous (IV) dose (lateral tail vein) of POZ propyl rotigotine (as described in Example 7) at equivalent doses of 0.5 and 2.0 mg/kg. The test articles were dissolved in 5% dextrose injection and filtered prior to each injection. Serial blood samples were obtained from each intravenously dosed animal through the cannulated catheter, at time intervals of end of injection, 12, 24, 48, 96 and 168 hours. The time intervals for the subcutaneously dosed animals were 6, 12, 24, 48, 96 and 168 hours. The blood was processed to collect the plasma which was stored at −70° C. before analysis. The plasma samples were extracted with acetonitrile using d3-rotigotine as an internal standard and the analytes in the extract were assayed by chromatographic analysis on LC/MS-MS system using a C-18 reverse phase column with 0.9 um silica coreshell (Accucore™, Thermo Scientific, 30×2.1 mm ID and 2.6 micron particle size). The mobile phase was ammonium formate 10 mM pH3.0 (solvent A); and 90% acetonitrile, 10% methanol, and 0.1% formic acid (solvent B), eluting at 0.6 mL/min.

The plasma concentration of rotigotine (ng/mL) after intravenous and subcutaneous injection is shown in FIGS. 2 and 3, respectively. These results suggest that POZ conjugates of rotigotine, whether dosed intravenously or subcutaneously, will reduce the clearance rate of rotigotine from the blood when compared to the parent molecule alone. The terminal plasma half-life (VA) for rotigotine, POZ acetyl rotigotine and POZ propyl rotigotine was 2.8, 16 and 60 h, respectively. However, there is a striking difference in the PK profiles when the POZ-conjugates POZ acetyl rotigotine and POZ propyl rotigotine when compared IV vs SC. POZ-conjugates delivered IV are generally cleared in a bi-phasic pattern with little difference between POZ acetyl rotigotine and POZ propyl rotigotine. However, when the two are compared following SC administration there is a marked difference. POZ acetyl rotigotine has essentially the same PK profile when delivered either SC or IV. POZ propyl rotigotine has a markedly prolonged PK profile that is near "zero order" kinetics. The size and length of the linker plays a role in the release of the agent, in this case rotigotine, and the levels measured in rat plasma from day 1 to day 7 are higher for the propyl linker than the acetyl linker. The initial plasma concentrations of rotigotine during the first 12 hours are lower for POZ propyl rotigotine when compared to the POZ acetyl rotigotine compound. At 12 hours, the $C_{max}$ values of plasma rotigotine were 6 ng/mL for POZ propyl rotigotine versus for 48 ng/mL for the POZ acetyl rotigotine when dosed SC at the dose of 1.6 mg/kg. This suggests that controlled delivery of an agent can be "tuned" to release the agent with a desired release profile without an initial burst effect based on the nature of the releasable linker, the size of the POZ polymer, the route of administration (e.g. subcutaneous) or a combination of the foregoing.

Example 32—Pharmacokinetics of Rotigotine in Monkey After Subcutaneous Administration of H-[(α-Methyl-Acetyl-Rotigotine)$_{10}$(EOZ)$_{190}$]—COOH 20K and H-[(Propionyl-Rotigotine)$_{10}$(EOZ)$_{190}$]—COOH 20K The pharmacokinetics of the POZ conjugates of rotigotine was measured in normal, treatment-naïve female macaques. Animals were randomly assigned into four treatment groups, each N=3. Animals received one subcutaneous dose of either POZ alpha methyl acetyl rotigotine (as described in Example 8) or POZ propyl rotigotine (as described in Example 7) at doses of either 1.5 mg/kg or 4.5 mg/kg (based on rotigotine equivalents). The test articles were dissolved in 5% dextrose injection and filtered prior to each injection. Serial venous blood samples were obtained from each animal prior to administration of experimental agents on Day 1 and subsequently at 15 min, 30 min, 1 h, 2 h, 4 h, 6 h, 8 h, 24 h, 48 h, 96 h, 192 h, 240 h and 336 h. The blood was processed to collect the plasma which was stored at −70° C. before analysis. These plasma samples were processed and assayed by chromatographic analysis on LC/MS-MS system as described in Example 31.

The plasma concentration of rotigotine (ng/mL) after subcutaneous injection is shown in FIG. 4. These results show that POZ conjugates of rotigotine will reduce the clearance rate of rotigotine from the blood. The average terminal plasma half-life (t½) of rotigotine from POZ alpha methyl acetyl rotigotine and POZ propionyl rotigotine was 9 and 60 h, respectively. Once again, the POZ propyl rotigotine has a markedly prolonged PK profile that is near "zero order" kinetics. The initial plasma concentrations of rotigotine during the first 12 hours are lower for POZ propyl rotigotine when compared to the POZ alpha methyl acetyl rotigotine compound. From 4 to 192 hours, the average $C_{ss}$ value of plasma rotigotine was between 1 and 6 ng/mL for POZ propyl rotigotine at the 1.5 mg/kg dose.

Example 33—Efficacy of H-[(Acetyl-Rotigotine)$_{10}$(EOZ)$_{190}$]—COOH 20K and H-[(Propionyl-Rotigotine)$_{10}$(EOZ)$_{190}$]—COOH 20K in the 6-OHDA Rat Model Following Subcutaneous Administration In order to study the efficacy of the POZ conjugates described herein, in vivo studies were conducted with female Sprague-Dawley rats. Female Sprague-Dawley rats (275-350 g) were used in the study. Each animal underwent stereotaxic surgery and received a unilateral lesion of the right nigrostriatal pathway via injection of 12.5 µg of 6-hydroxydopamine (6-OHDA) into a single site in the medial forebrain bundle. Rats were monitored over two weeks and underwent behavioral assessment (on day −7) via the cylinder test. Animals lacking overt behavioral asymmetry (>85% ipsilateral forelimb use) were excluded from the study. The rats were them randomly assigned to one of six treatment groups (each N=8). The groups were as follows: vehicle control (Group A); rotigotine hydrochloride 0.5 mg/kg (Group B); rotigotine hydrochloride 3 mg/kg (Group C); H-[(Acetyl-Rotigotine)$_{10}$(EOZ)$_{190}$]—COOH 20K (as described in Example 6) 1.6 mg/kg (Group D); H-[(Propionyl-Rotigotine)$_{10}$(EOZ)$_{190}$]—COOH 20K (as described in Example 7) 1.6 mg/kg (Group E); and H-[(Propionyl-Rotigotine)$_{10}$(EOZ)$_{190}$]—COOH 20K (as described in Example 7) 6.4 mg/kg (Group F). The rats received a single subcutaneous dose (2 mL/kg) of vehicle (5% dextrose) or test compound dissolved in 5% dextrose.

The results are presented in Table 6. All treatments show positive rotational behaviors (contraversive turns) on day 1 of dosing. Only POZ propyl rotigotine shows activity on day 5, with marked and continuous contraversive rotations at the high dose of 6.4 mg/kg. This favorable response is due to the high and sustained rotigotine drug levels in blood on day 5, which was observed in the pharmacokinetic study (Example 32).

Each group of animals (A-F as described above) were independently assessed rat for rotational behavior and forelimb symmetry on day 1, day 2, day 5 and day 9. In the rotational test, the animals were placed in an automated rotometer apparatus (MedAssociates, USA) and the net number of rotations contraversive to the lesion were recorded over a period of 6 hours on each day. In the forelimb symmetry test, the rats are placed in a clear glass cylinder without top (15 cm diameter×45 cm tall). The number of times each paw touches the side of the cylinder during an individual rear is recorded over a 10 minute observation on each day. The first limb in any rear to touch the wall is scored a single point. If both limbs contact within 0.4 s of each other, then this is scored as a 'both'. All subsequent exploratory movements about the wall using that limb are scored independently until the other limb contacts the wall with weight support. Alternating stepping motions involving both paws one after the other receive a single score for both. The net number of contralateral touches are calculated and considered a favorable response.

The results are presented in Table 7. All treatments show positive ipsiversive forelimb use on day 1 of dosing. Only POZ propyl rotigotine shows activity on day 5, with marked and continuous ipsiversive forelimb use at the both doses of 1.6 and 6.4 mg/kg. This favorable response is due to the high and sustained rotigotine drug levels in blood on day 5, which was observed in the pharmacokinetic study (Example 32).

The following table 6 summarizes the results of the rotational test:

TABLE 6

| Compound | Dose (mg/kg) | Net number of contraversive turns/6 h period (Average ± SEM; n = 8) | |
|---|---|---|---|
| | | Day 1 | Day 5 |
| Vehicle | 0 | −56 ± 20 | −25 ± 11 |
| Rotigotine | 0.5 | 983 ± 405 | −49 ± 9 |
| Rotigotine | 3.0 | 1570 ± 312* | −39 ± 15 |
| POZ Acetyl Rotigotine 20K | 1.6 | 872 ± 232 | −14 ± 14 |
| POZ Propionyl Rotigotine 20K | 1.6 | 1408 ± 286* | 68 ± 60 |
| POZ Propionyl Rotigotine 20K | 6.4 | 1272 ± 405* | 5142 ± 777** |

*/**represents P < 0.01 or P < 0.001 cf. vehicle (1-way ANOVA with Dunnett's post-hoc test).

The following table 7 summarizes the results of the forelimb asymmetry test:

TABLE 7

| Compound | Dose (mg/kg) | Net ipsiversive forelimb use as a percentage of total forelimb use (Average ± SEM; n = 8) | |
|---|---|---|---|
| | | Day 2 | Day 5 |
| Vehicle | 0 | 88 ± 7% | 85 ± 6% |
| Rotigotine | 0.5 | 60 ± 13% | 94 ± 6% |
| Rotigotine | 3.0 | 9 ± 13%* | 85 ± 8% |
| POZ Acetyl Rotigotine 20K | 1.6 | 50 ± 13% | 85 ± 10% |
| POZ Propyl Rotigotine 20K | 1.6 | 0 ± 14%** | 31 ± 13%* |
| POZ Propyl Rotigotine 20K | 6.4 | −2 ± 26%** | −6 ± 16%** |

*/**represents P < 0.01 or P < 0.001 cf. vehicle (1-way ANOVA with Dunnett's post-hoc test).

What is claimed:

1. A method for treating a disease or condition selected from the group consisting of restless leg syndrome and Parkinson's disease in a subject in need thereof, the method comprising the step of administering to the subject a poly(oxazoline) polymer conjugate comprising a water soluble poly(oxazoline) polymer and an agent, wherein a release profile of the agent is selectable based on the selection of the poly(oxazoline) polymer conjugate, the poly(oxazoline) polymer conjugate having the structure:

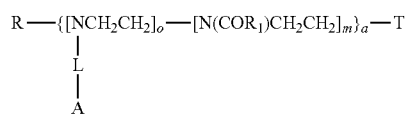

wherein
L is

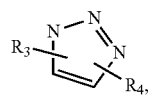

$R_3$ forms a linkage with the poly(oxazoline) polymer;
$R_4$ is —$CH_2$—C(O)—O—, —CH($CH_3$)—C(O)—O—, —$CH_2$—$CH_2$—C(O)—O—, —$CH_2$—$CH_2$—$CH_2$—C (O)—O—, —CH₂—O—C(O)—, —CH(CH₃)—O—C(O)—, —CH₂—CH₂—O—C(O)— or —CH₂—CH₂—CH₂—O—C(O)—;

R is an initiating group;

R₁ is a non-reactive group;

A is rotigotine, pramipexole, quinagolide, fenoldopam, apomorphine, 5-OH-DPAT, ropinirole, pergolide, cabergoline, bromocriptine, theophylline, istradefylline, preladenant trihexyphenidyl, biperidin, hyoscyamine, selegiline, rasagiline, tolcapone or entacapone;

a is ran which indicates a random copolymer or block which indicates a block copolymer;

o is from 1-50;

m is from 1-1000; and

T is a terminating group, wherein the release profile is dependent on the selection of R₄.

2. The method of claim 1, wherein R₃ is —C(O)—(CH₂)₃ and R₄ is —CH₂—C(O)—O—, —CH₂—CH₂—C(O)—O—, —CH(CH₃)—C(O)—O— or —CH₂—CH₂—CH₂—C(O)—O—.

3. The method of claim 1, wherein L has the structure

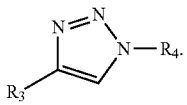

4. The method of claim 1, wherein T is —Z—B-Q wherein

Z is S, O, or N;

B is an optional linking group; and

Q is a terminal portion of a terminating nucleophile.

5. The method of claim 1, wherein R is hydrogen, alkyl or substituted alkyl.

6. The method of claim 1, wherein the agent is rotigotine.

7. The method of claim 1, wherein the polymer conjugate is administered alone or as a part of a pharmaceutical composition.

8. The method of claim 1, wherein the polymer conjugate is administered in a therapeutically effective amount.

9. The method of claim 1, wherein the polymer conjugate is administered by subcutaneous administration.

10. The method of claim 6, wherein the release profile provides a controllable delivery of the rotigotine over a period of days.

11. The method of claim 6, wherein the release profile provides a controllable delivery of the rotigotine over a period of weeks.

12. The method of claim 1, wherein R₃ is —C(O)—(CH₂)₃— and R₄ is —CH₂—CH₂—C(O)—O—.

13. The method of claim 1, wherein R₃ is —C(O)—(CH₂)₃— and R₄ is —CH(CH₃)—C(O)—O—.

14. The method of claim 1, wherein R₃ is —C(O)—(CH₂)₃— and R₄ is —CH₂—C(O)—O—.

15. The method of claim 1, wherein R₁ is —CH₃ or —CH₂CH₃.

16. The method of claim 1, wherein T is —S—CH₂CH₂—COOH.

17. The method of claim 1, wherein R₃ is —C(O)—(CH₂)₃—, R₄ is —CH₂—CH₂—C(O)—O—, CH(CH₃)—C(O)—O—, or —CH₂—C(O)—O—, and the disease or condition is Parkinson's disease.

18. The method of claim 17, wherein the agent is rotigotine, pramipexole, apomorphine, ropinirole, trihexyphenidyl, seligiline, rasagiline, tolcapone or entacapone.

19. The method of claim 18, wherein T is —S—CH₂CH₂—COOH.

20. The method of claim 19, wherein R₁ is —CH₃ or —CH₂CH₃.

* * * * *